US010059708B2

(12) United States Patent
Shilatifard et al.

(10) Patent No.: US 10,059,708 B2
(45) Date of Patent: Aug. 28, 2018

(54) THERAPEUTIC TARGETING OF THE INTERLEUKIN 1 RECEPTOR-ASSOCIATED KINASE 4 (IRAK4) IN LEUKEMIAS CHARACTERIZED BY REARRANGEMENTS IN THE MIXED LINEAGE LEUKEMIA GENE (MLL-R)

(71) Applicant: Northwestern University, Evanston, IL (US)

(72) Inventors: Ali Shilatifard, Chicago, IL (US); Kaiwei Liang, Chicago, IL (US); Edwin Richard Smith, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/497,783

(22) Filed: Apr. 26, 2017

(65) Prior Publication Data

US 2017/0305901 A1 Oct. 26, 2017

Related U.S. Application Data

(60) Provisional application No. 62/327,761, filed on Apr. 26, 2016.

(51) Int. Cl.
*C07D 471/04* (2006.01)
*C07D 233/88* (2006.01)

(52) U.S. Cl.
CPC ......... *C07D 471/04* (2013.01); *C07D 233/88* (2013.01)

(58) Field of Classification Search
None
See application file for complete search history.

(56) References Cited

PUBLICATIONS

Zips et al., in vivo, 2005, 19, 1-8.*
Wang et al., Somatic Mutations of the Mixed-Lineage Leukemia 3 (MLL3) Gene in Primary Breast Cancers, Pathology & Oncology Research, Jun. 2011, vol. 17, Issue 2, pp. 429-433.*
Sikora Current Science 2001, 81(5), 549-554.*
Schmutzler et al. European Journal of Endocrinology 2000, 143, 15-24.*
Armstrong, S.A., Staunton, J.E., Silverman, L.B., Pieters, R., den Boer, M.L., Minden, M.D., Sallan, S.E., Lander, E.S., Golub, T.R., and Korsmeyer, S.J. (2002). MLL translocations specify a distinct gene expression profile that distinguishes a unique leukemia. Nat. Genet. 30, 41-47.
Borkin, D., He, S., Miao, Fl, Kempinska, K., Pollock, J., Chase, J., Purohit, T., Malik, B., Zhao, T., Wang, J., et al. (2015). Pharmacologic inhibition of the Menin-MLL interaction blocks progression of MLL leukemia in vivo. Cancer Cell 27, 589-602.
Cao, F., Townsend, E.G., Karatas, H., Xu, J., Li, L., Lee, S., Liu, L., Chen, Y., Ouillette, P., Zhu, J., et al. (2014). Targeting MLL1 H3K4 methyltransferase activity in mixed-lineage leukemia. Mol. Cell 53, 247-261.
Dawson, M.A., Prinjha, R.K., Dittmann, A., Giotopoulos, G., Bantscheff, M., Chan, W.I., Robson, S.C., Chung, C.W., Hopf, C., Savitski, M.M., et al. (2011). Inhibition of BET recruitment to chromatin as an effective treatment for MLL-fusion leukaemia. Nature 478, 529-533.
Fong, C.Y., Gilan, O., Lam, E.Y., Rubin, A.F., Ftouni, S., Tyler, D., Stanley, K., Sinha, D., Yeh, P., Morison, J., et al. (2015). BET inhibitor resistance emerges from leukaemia stem cells. Nature 525, 538-542.
Gan, T., Jude, C.D., Zaffuto, K., and Ernst, P. (2010). Developmentally induced MII1 loss reveals defects in postnatal haematopoiesis. Leukemia 24, 1732-1741.
Guenther, M.G., Lawton, L.N., Rozovskaia, T., Frampton, G.M., Levine, S.S., Volkert, T.L., Croce, C.M., Nakamura, T., Canaani, E., and Young, R.A. (2008). Aberrant chromatin at genes encoding stem cell regulators in human mixed-lineage leukemia. Genes Dev. 22, 3403-3408.
Hanson, R.D., Hess, J.L., Yu, B.D., Ernst, P., van Lohuizen, M., Berns, A., van der Lugt, N.M., Shashikant, C.S., Ruddle, F.H., Seto, M., and Korsmeyer, S.J. (1999). Mammalian Trithorax and polycomb-group homologues are antagonistic regulators of homeotic development. Proc. Natl. Acad. Sci. USA 96, 14372-14377.
Jones, W.D., Dafou, D., McEntagart, M., Woollard, W.J., Elmslie, F.V., Holder-Espinasse, M., Irving, M., Saggar, A.K., Smithson, S., Trembath, R.C., et al. (2012). De novo mutations in MLL cause Wiedemann-Steiner syndrome. Am. J. Hum. Genet. 91, 358-364.
Jude, C.D., Gilmer, L., Xu, D., Artinger, E., Fisher, J.K., and Ernst, P. (2007). Unique and independent roles for MLL in adult hematopoietic stem cells and progenitors. Cell Stem Cell 1, 324-337.
Kim, D. Pertea, G., Trapnell, C., Pimentel, H., Kelley, R., and Salzberg, S.L. (2013). TopHat2: accurate alignment of transcriptomes in the presence of insertions, deletions and gene fusions. Genome Biol. 14, R36.
Kuo, H.P., Wang, Z., Lee, D.F., Iwasaki, M., Duque-Afonso, J., Wong, S.H., Lin, C.H., Figueroa, M.E., Su, J., Lemischka, I.R., and Cleary, M.L. (2013). Epigenetic roles of MLL oncoproteins are dependent on Nf-kB. Cancer Cell 24, 423-437.
Langmead, B., Trapnell, C., Pop, M., and Salzberg, S.L. (2009). Ultrafast and memory-efficient alignment of short DNA sequences to the human genome. Genome Biol. 10, R25.
Li, B.E., and Ernst, P. (2014). Two decades of leukemia oncoprotein epistasis: the MLL1 paradigm for epigenetic deregulation in leukemia. Exp. Hematol. 42, 995-1012.

(Continued)

*Primary Examiner* — Svetlana M Ivanova
(74) *Attorney, Agent, or Firm* — Andrus Intellectual Property Law, LLP

(57) ABSTRACT

Disclosed are methods for treating cancers associated with rearrangements in the mixed lineage leukemia gene (MLL-r), including MLL-r leukemia. The methods typically include administering a therapeutic amount of one or more therapeutic agents that inhibit the biological activity of one or more members of the interleukin-1 signaling pathway such inhibitors of interleukin-1 receptor-associated kinase 4 (IRAK4).

16 Claims, 61 Drawing Sheets

(56) References Cited

PUBLICATIONS

Li, Z., Younger, K., Gartenhaus, R., Joseph, A.M., Hu, F., Baer, M.R., Brown, P., and Davila, E. (2015). Inhibition of IRAK1/4 sensitizes T cell acute lymphoblastic leukemia to chemotherapies. J. Clin. Invest. 125, 1081-1097.
Liang, K., Gao, X., Gilmore, J.M., Florens, L., Washburn, M.P., Smith, E., and Shilatifard, A. (2015a). Characterization of human cyclin-dependent kinase 12 (CDK12) and CDK13 complexes in C-terminal domain phosphorylation, gene transcription, and RNA processing. Mol. Cell. Biol. 35, 928-938.
Liang, K., Woodfin, A.R., Slaughter, B.D., Unruh, J.R., Box, A.C., Rickels, R.A., Gao, X., Haug, J.S., Jaspersen, S.L., and Shilatifard, A. (2015b). Mitotic transcriptional activation: clearance of actively engaged Pol II via transcriptional elongation control in mitosis. Mol. Cell 60, 435-445.
Lin, C., Smith, E.R., Takahashi, H., Lai, K.C., Martin-Brown, S., Florens, L., Washburn, M.P., Conaway, J.W., Conaway, R.C., and Shilatifard, A. (2010). AFF4, a component of the ELL/P-TEFb elongation complex and a shared subunit of MLL chimeras, can link transcription elongation to leukemia. Mol. Cell 37, 429-437.
Liu, Y., Cheng, H., Gao, S., Lu, X., He, F., Hu, L., Hou, D., Lou, Z., Li, Y., Zhang, H., et al. (2014). Reprogramming of MLL-AF9 leukemia cells into pluripotent stem cells. Leukemia 28, 1071-1080.
Lu, T., Jackson, M.W., Singhi, A.D., Kandel, E.S., Yang, M., Zhang, Y., Gudkov, A.V., and Stark, G.R. (2009). Validation-based insertional mutagenesis identifies lysine demethylase FBXL11 as a negative regulator of NFkappaB. Proc. Natl. Acad. Sci. USA 106, 16339-16344.
Mashtalir, N., Daou, S., Barbour, H., Sen, N.N., Gagnon, J., Hammond-Martel, I., Dar, H.H., Therrien, M., and Affar, B. (2014). Autodeubiquitination protects the tumor suppressor BAP1 from cytoplasmic sequestration mediated by the atypical ubiquitin ligase UBE2O. Mol. Cell 54, 392-406.
McMahon, K.A., Hiew, S.Y., Hadjur, S., Veiga-Fernandes, H., Menzel, U., Price, A.J., Kioussis, D., Williams, O., and Brady, H.J. (2007). Mll has a critical role in fetal and adult hematopoietic stem cell self-renewal. Cell Stem Cell 1, 338-345.
Meyer, C., Hofmann, J., Burmeister, T., Groger, D., Park, T.S., Emerenciano, M., Pombo de Oliveira, M., Renneville, A., Villarese, P., Macintyre, E., et al. (2013). The MLL recombinome of acute leukemias in 2013. Leukemia 27, 2165-2176.
Mi, H., Muruganujan, A., Casagrande, J.T., and Thomas, P.D. (2013). Largescale gene function analysis with the PANTHER classification system. Nat. Protoc. 8, 1551-1566.
Miller, T., Krogan, N.J., Dover, J., Erdjument-Bromage, H., Tempst, P., Johnston, M., Greenblatt, J.F., and Shilatifard, A. (2001). COMPASS: a complex of proteins associated with a trithorax-related SET domain protein. Proc. Natl. Acad. Sci. USA 98, 12902-12907.
Milne, T.A., Kim, J., Wang, G.G., Stadler, S.C., Basrur, V., Whitcomb, S.J., Wang, Z., Ruthenburg, A.J., Elenitoba-Johnson, K.S., Roeder, R.G., and Allis, C.D. (2010). Multiple interactions recruit MLL1 and MLL1 fusion proteins to the HOXA9 locus in leukemogenesis. Mol. Cell 38, 853-863.
Mishra, B.P., Zaffuto, K.M., Artinger, E.L., Org, T., Mikkola, H.K., Cheng, C., Djabali, M., and Ernst, P. (2014). The histone methyltransferase activity of MLL1 is dispensable for hematopoiesis and leukemogenesis. Cell Rep. 7, 1239-1247.
Mohan, M., Herz, H.M., Takahashi, Y.H., Lin, C., Lai, K.C., Zhang, Y., Washburn, M.P., Florens, L., and Shilatifard, A. (2010a). Linking H3K79 trimethylation to Wnt signaling through a novel Dot1-containing complex (DotCom). Genes Dev. 24, 574-589.
Mohan, M., Lin, C., Guest, E., and Shilatifard, A. (2010b). Licensed to elongate: a molecular mechanism for MLL-based leukaemogenesis. Nat. Rev. Cancer 10, 721-728.
Nguyen, A.T., Taranova, O., He, J., and Zhang, Y. (2011). DOT1L, the H3K79 methyltransferase, is required for MLL-AF9-mediated leukemogenesis. Blood 117, 6912-6922.
Okuda, H., Kawaguchi, M., Kanai, A., Matsui, H., Kawamura, T., Inaba, T., Kitabayashi, I., and Yokoyama, A. (2014). MLL fusion proteins link transcriptional coactivators to previously active CpG-rich promoters. Nucleic Acids Res. 42, 4241-4256.
Pigneux, A., Labopin, M., Maertens, J., Cordonnier, C., Volin, L., Socie', G., Blaise, D., Craddock, C., Milpied, N., Bacher, U., et al.; Acute Leukemia Working Party EBMT (2015). Outcome of allogeneic hematopoietic stem-cell transplantation for adult patients with AML and 11q23/MLL rearrangement (MLL-r AML). Leukemia 29, 2375-2381.
Powers, J.P., Li, S., Jaen, J.C., Liu, J., Walker, N.P., Wang, Z., and Wesche, H. (2006). Discovery and initial SAR of inhibitors of interleukin-1 receptor-associated kinase-4. Bioorg. Med. Chem. Lett. 16, 2842-2845.
Rathert, P., Roth, M., Neumann, T., Muerdter, F., Roe, J.S., Muhar, M., Deswal, S., Cerny-Reiterer, S., Peter, B., Jude, J., et al. (2015). Transcriptional plasticity promotes primary and acquired resistance to BET inhibition. Nature 525, 543-547.
Rhyasen, G.W., Bolanos, L., Fang, J., Jerez, A., Wunderlich, M., Rigolino, C., Mathews, L., Ferrer, M., Southall, N., Guha, R., et al. (2013). Targeting IRAK1 as a therapeutic approach for myelodysplastic syndrome. Cancer Cell 24, 90-104.
Robinson, M.D., McCarthy, D.J., and Smyth, G.K. (2010). edgeR: a Bioconductor package for differential expression analysis of digital gene expression data. Bioinformatics 26, 139-140.
Shen, L., Shao, N., Liu, X., and Nestler, E. (2014). ngs.plot: Quick mining and visualization of next-generation sequencing data by integrating genomic databases. BMC Genomics 15, 284.
Shilatifard, A. (2012). The COMPASS family of histone H3K4 methylases: mechanisms of regulation in development and disease pathogenesis. Annu. Rev. Biochem. 81, 65-95.
Singer, A. (2015). Epizyme announces second quarter 2015 financial results and provides corporate update. https://www.sec.gov/Archives/edgar/data/1571498/000119312515279839/d23584dex991.htm.
Smith, E., Lin, C., and Shilatifard, A. (2011). The super elongation complex (SEC) and MLL in development and disease. Genes Dev. 25, 661-672.
Thiel, A.T., Blessington, P., Zou, T., Feather, D., Wu, X., Yan, J., Zhang, H., Liu, Z., Ernst, P., Koretzky, G.A., and Hua, X. (2010). MLL-AF9-induced leukemogenesis requires coexpression of the wild-type Mll allele. Cancer Cell 17, 148-159.
Tomizawa, D., Koh, K., Sato, T., Kinukawa, N., Morimoto, A., Isoyama, K., Kosaka, Y., Oda, T., Oda, M., Hayashi, Y., et al. (2007). Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group. Leukemia 21, 2258-2263.
Tripathi, S., Pohl, M.O., Zhou, Y., Rodriguez-Frandsen, A., Wang, G., Stein, D.A., Moulton, H.M., DeJesus, P., Che, J., Mulder, L.C., et al. (2015). Metaand orthogonal integration of influenza "OMICs" data defines a role for UBR4 in virus budding. Cell Host Microbe 18, 723-735.
Tumey, L.N., Boschelli, D.H., Bhagirath, N., Shim, J., Murphy, E.A., Goodwin, D., Bennett, E.M., Wang, M., Lin, L.L., Press, B., et al. (2014). Identification and optimization of indolo[2,3-c]quinoline inhibitors of IRAK4. Bioorg. Med. Chem. Lett. 24, 2066-2072.
Volk, A., Li, J., Xin, J., You, D., Zhang, J., Liu, X., Xiao, Y., Breslin, P., Li, Z., Wei, W., et al. (2014). Co-inhibition of NF-kB and JNK is synergistic in TNF-expressing human AML. J. Exp. Med. 211, 1093-1108.
Wang, P., Lin, C., Smith, E.R., Guo, H., Sanderson, B.W., Wu, M., Gogol, M., Alexander, T., Seidel, C., Wiedemann, L. M., et al. (2009). Global analysis of H3K4 methylation defines MLL family member targets and points to a role for MLL1-mediated H3K4 methylation in the regulation of transcriptional initiation by RNA polymerase II. Mol. Cell. Biol. 29, 6074-6085.
Wang, Q.F., Wu, G., Mi, S., He, F., Wu, J., Dong, J., Luo, R.T., Mattison, R., Kaberlein, J.J., Prabhakar, S., et al. (2011). MLL fusion proteins preferentially regulate a subset of wild-type MLL target genes in the leukemic genome. Blood 117, 6895-6905.
Whitman, S.P., Liu, S., Vukosavljevic, T., Rush, L.J., Yu, L., Liu, C., Klisovic, M.I., Maharry, K., Guimond, M., Strout, M.P., et al.

(56) References Cited

OTHER PUBLICATIONS (2005). The MLL partial tandem duplication: evidence for recessive gain-of-function in acute myeloid leukemia identifies a novel patient subgroup for molecular-targeted therapy. Blood 106, 345-352.

Yokoyama, A., Lin, M., Naresh, A., Kitabayashi, I., and Cleary, M.L. (2010). A higher-order complex containing AF4 and ENL family proteins with P-TEFb facilitates oncogenic and physiologic MLL-dependent transcription. Cancer Cell 17, 198-212.

Yokoyama, A., Ficara, F., Murphy, M.J., Meisel, C., Naresh, A., Kitabayashi, I., and Cleary, M.L. (2011). Proteolytically cleaved MLL subunits are susceptible to distinct degradation pathways. J. Cell Sci. 124, 2208-2219.

Yu, B.D., Hess, J.L., Horning, S.E., Brown, G.A., and Korsmeyer, S.J. (1995). Altered Hox expression and segmental identity in MII-mutant mice. Nature 378, 505-508.

Zhang, Y., Liu, T., Meyer, C.A., Eeckhoute, J., Johnson, D.S., Bernstein, B.E., Nusbaum, C., Myers, R.M., Brown, M., Li, W., and Liu, X.S. (2008). Modelbased analysis of ChIP-Seq (MACS). Genome Biol. 9, R137.

* cited by examiner

| | MLL | | | UBE2O | | |
|---|---|---|---|---|---|---|
| | Peptides | d_S | dNSAF | Peptides | d_S | dNSAF |
| MLL-Inter | 53 | 454 | 0.0042 | 16 | 63 | 0.0018 |
| MLL-CT | 33 | 658 | 0.0173 | X | X | X |
| Vector | X | X | X | X | X | X |

F

G

A
IRAK4 Inhibitor
Relative viable cells
1
0.5
0
DMSO
25 nM
50 nM
100 nM
250 nM
500 nM
1000 nM
NB-4
OCI-LY1
SU-DHL-5
SU-DHL-6
REH
U937
RL
(Non-MLL-r)
SEM (MLL-AFF1)
MM6 (MLL-AF9)
RS4;11 (MLL-AFF1)
MOLM-13 (MLL-AF9)
MV4-11 (MLL-AFF1)
ML2 (MLL-AF6 with wide-type MLL deletion)
B
MM6(MLL-AF9)
Viable cells (Million/ml)
7
6
5
4
3
2
1
0
DMSO
IRAK1/4 inhibitor (5 μM)
DAY 0
DAY 1
DAY 2
DAY 3
DAY 4
DAY 5
DAY 6
DAY 7
Viable cells (Million/ml)
1.6
1.4
1.2
1
0.8
0.6
0.4
0.2
0
DMSO
IRAK4 inhibitor (500 nM)
DAY0
DAY1
DAY2
DAY3

| Average dNSAF | Flag-MLL-NT | Flag-MLL-AF9 | Flag-MLL-AFF1 | Flag-MLL-ELL | Flag-MLL-ENL |
|---|---|---|---|---|---|
| MLL-NT | 0.05092 | X | X | X | X |
| MLL-AF9 | X | 0.05169 | X | X | X |
| MLL-AFF1 | X | X | 0.01244 | X | X |
| MLL-ELL | X | X | X | 0.07139 | X |
| MLL-ENL | X | X | X | X | 0.05455 |
| UBE2O | X | X | X | X | X |

MudPIT analysis of Halo-MLL Complexes

| dNSAF | Vector | Halo-MLL1 |
|---|---|---|
| MLL1 | 0 | 0.00749 |
| RBBP5 | 0 | 0.000113 |
| ASH2L | 0 | 0.0000969 |
| DPY30 | 0 | 0.00276 |
| WDR5 | 0 | 0.0009114 |
| HCFC1 | 0 | 0.0000374 |
| Menin | 0 | 0.000973 |
| CXXC1 | 0 | 0 |
| WDR82 | 0 | 0 |

E Enriched pathways in shRNA screening for MLL degradation

| Molecular Function | Fold Enrichment | P value |
|---|---|---|
| Interleukin-1 receptor activity | > 5 | 7.50E-03 |
| Cytokine receptor activity | > 5 | 1.53E-04 |

| Biological Process | Fold Enrichment | P value |
|---|---|---|
| Regulation of immune response | 2.46 | 3.59E-02 |
| Immune response | 2.43 | 1.38E-04 |

D
DMSO
IRAK1/4 Inhibitor
(10 μM for 24 hr)
rpm
HEK293
HOXA Cluster
Chr7:27,103,753
27,292,464
HOXC Cluster
Chr12:54,307,470
54,452,153
FOXC1
Chr6:1,599,843
1,620,251

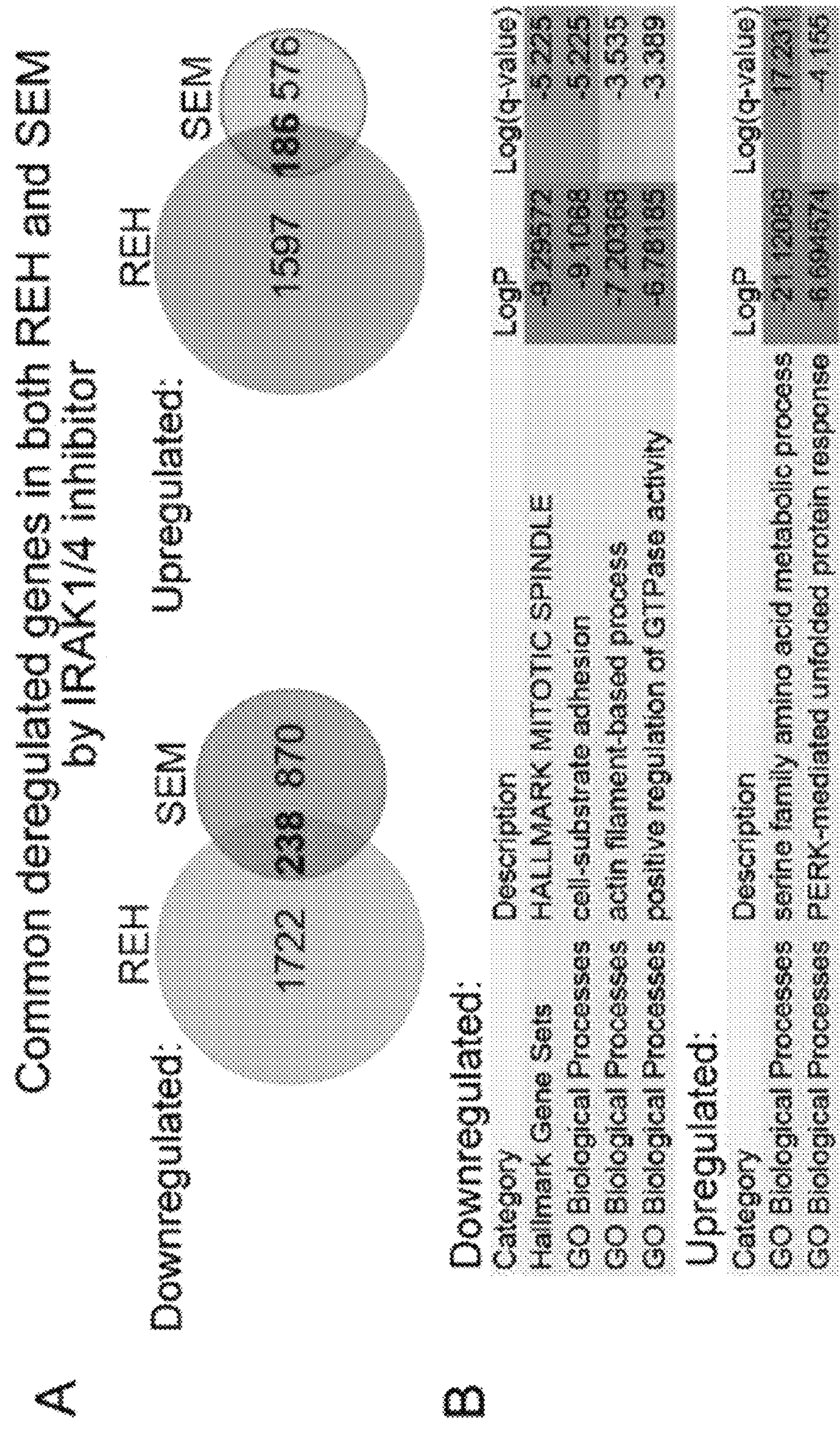
Figure 11
A
Common deregulated genes in both REH and SEM by IRAK1/4 inhibitor
Downregulated:
REH
SEM
1722
238
870
Upregulated:
REH
SEM
1597
186
576
B
Downregulated:
Category
Description
LogP
Log(q-value)
Hallmark Gene Sets
HALLMARK MITOTIC SPINDLE
-9.29572
-5.225
GO Biological Processes
cell-substrate adhesion
-9.1068
-5.225
GO Biological Processes
actin filament-based process
-7.20368
-3.535
GO Biological Processes
positive regulation of GTPase activity
-6.78185
-3.389
Upregulated:
Category
Description
LogP
Log(q-value)
GO Biological Processes
serine family amino acid metabolic process
-21.12089
-17.231
GO Biological Processes
PERK-mediated unfolded protein response
-6.694574
-4.155

Gene ontology of SEM-specific downregulated genes by both IRAK inhibitors

| Category | Term | Description | LogP | Log(q-value) |
|---|---|---|---|---|
| GO Biological Processes | GO:0001775 | cell activation | -12.85271 | -8.67015 |
| GO Biological Processes | GO:0007229 | integrin-mediated signaling pathway | -8.853644 | -5.425329 |
| GO Biological Processes | GO:0031589 | cell-substrate adhesion | -8.528502 | -5.410795 |
| GO Biological Processes | GO:0071363 | cellular response to growth factor stimulus | -8.264287 | -5.227858 |
| GO Biological Processes | GO:0008284 | positive regulation of cell proliferation | -7.611808 | -4.771673 |
| GO Biological Processes | GO:0002684 | positive regulation of immune system process | -7.374484 | -4.623291 |
| GO Biological Processes | GO:0030029 | actin filament-based process | -6.874054 | -4.182858 |
| KEGG Pathway | hsa05202 | transcriptional misregulation in cancer | -7.336477 | -4.601078 |
| Hallmark Gene Sets | M5890 | HALLMARK TNFA SIGNALING VIA NFKB | -8.573492 | -5.410795 |
| Hallmark Gene Sets | M5947 | HALLMARK IL2 STAT5 SIGNALING | -7.855786 | -4.795448 |

G
Vector
CMV
EF1
GFP
MLL NT1-1250
CMV
EF1
GFP
SEM cells
20X
H
SEM(MLL-AFF1)
Vector
MLL-NT
Viable cells (million/ml)
2.5
2
1.5
1
0.5
0
DAY0
DAY1
DAY2
DAY3

B

Common Upregulated Genes in SEM and MM6 Cells
(Adjusted p <0.01)

C

B

In Vitro IRAK4 kinase assay

A

B

THERAPEUTIC TARGETING OF THE INTERLEUKIN 1 RECEPTOR-ASSOCIATED KINASE 4 (IRAK4) IN LEUKEMIAS CHARACTERIZED BY REARRANGEMENTS IN THE MIXED LINEAGE LEUKEMIA GENE (MLL-R)

CROSS-REFERENCE TO RELATED PATENT APPLICATIONS

This application claims the benefit of priority under 35 U.S.C. § 119(e) to U.S. Provisional Application No. 62/327,761, filed on Apr. 26, 2016, the content of which is incorporated herein by reference in its entirety.

STATEMENT REGARDING FEDERALLY SPONSORED RESEARCH OR DEVELOPMENT

This invention was made with government support under RO1 CA150265 awarded by the National Institutes of Health. The government has certain rights in the invention.

BACKGROUND

The field of the invention relates to methods for treating cancers. In particular, the field of the invention relates to methods, compounds, and compositions for treating cancers characterized by rearrangements in the mixed lineage leukemia gene, otherwise referred to as "MLL-r cancers," including MLL-r leukemias. The methods, compounds, and compositions disclosed herein relate to the use of therapeutic agents that inhibit the biological activity of one or more members of the interleukin-1 signaling pathway, such as inhibitors of interleukin-1 receptor kinase 4 (IRAK4).

Rearrangements or translocations of the mixed lineage leukemia gene (MLL-r) have been shown to be associated with aggressive forms of leukemia. Cases of acute lymphoblastic leukemia (ALL) and acute myelogenous leukemia (AML) that are characterized by MLL-r are extremely aggressive and are predominantly seen in infants and in therapy-related leukemias. In contrast to other types of leukemias, the prognosis for MLL-r is dismal and despite advances in new therapies, cure rates have plateaued over the last several years. Therefore, new therapies are needed.

Chromosomal rearrangements involving translocations between one copy of 11q23 and another chromosome can generate oncogenic fusion proteins consisting of an n-terminal portion of MLL and c-terminal portion of the fusion partner. The normal in vivo function of MLL is as the enzymatic subunit of a COMPASS-like complex that methylates histone H3 on its fourth lysine. The chimeric protein lacks the c-terminal methyltransferase, but gains properties of the c-terminal fusion partner. Since many of the translocation partners are transcriptional activators, the aberrant recruitment of the translocation partner to normal MLL targets, which include oncogenes, drives leukemogenesis. Despite the chromosomal translocation, one wild-type copy of the MLL gene exists but the protein levels expressed from this allele are much lower than the MLL chimeric protein. Therefore, the present inventors hypothesized that a decrease in wild-type MLL protein observed in MLL-r may contribute to the development of leukemia.

Here, the inventors have shown that the wild-type MLL protein is decreased in MLL-r leukemia cells. Further, the inventors have shown that the interleukin-1 signaling pathway regulates the turnover of MLL protein. By administering inhibitors of the interleukin-1 signaling pathway to leukemia cells lines, including inhibitors of IRAK4, the inventors have determined that levels of wild-type MLL protein can be increased and growth of MLL-r leukemia cells can be inhibited. Furthermore, inhibitors of inhibitors of the interleukin-1 signaling pathway, including inhibitors of IRAK4, increased survival in a murine leukemia model. In addition to studying inhibitors of the interleukin-1 signaling pathway known in the art, the inventors also synthesized new inhibitors of IRAK4. By administering the new inhibitors of IRAK4 leukemia cells, the inventors have determined that levels of wild-type MLL protein can be increased and growth of MLL-r leukemia cells can be inhibited The inventors' results have implications for MLL-r leukemias as well as other types of cancers which are shown to be characterized by MLL-r.

SUMMARY

Disclosed are methods, compounds, and compositions for treating cancers characterized by rearrangements in the mixed lineage leukemia gene, otherwise referred to as "MLL-r cancers." The disclosed methods include, but are not limited to, treating MLL-r leukemia. The methods include administering a therapeutic amount of one or more therapeutic agents that inhibit the biological activity of one or more members of the interleukin-1 signaling pathway to a subject having a cancer characterized by MLL-r, including inhibitors of interleukin-1 receptor kinase 4 (IRAK4).

Therapeutic agents administered in the disclosed methods may inhibit the biological activity of one or more members of the interleukin-1 signaling pathway, which may include but are not limited to inhibitors of the interleukin-1 receptor-associated kinase (IRAK), such as inhibitors of IRAK1, IRAK2, IRAK3, and/or IRAK4 in particular. Therapeutic agents administered in the disclosed methods may inhibit the biological activity of other members of the interleukin-1 signaling pathway such as interleukin-1 ligand α (IL1α), interleukin 1 ligand β (ILβ), interleukin-1 receptor type 1 (IL1R1), interleukin-1 receptor accessory protein (IL1RAP), toll interacting protein (TOLLIP), myeloid differentiation primary response gene 88 (MYD88), tumor necrosis factor receptor-associated factor 6 (TRAF6), and any combination thereof.

The therapeutic agents may include, but are not limited to, small molecule inhibitors, peptide inhibitors, and/or nucleic acid molecules. The therapeutic agents may inhibit the expression and/or activity of the one or more members of the interleukin-1 signaling pathway.

Also disclosed herein are new compounds which may inhibit one or more members of the interleukin-1 signaling pathway, such as IRAK4. The compounds may be formulated as pharmaceutical compositions, for example for treating cancers characterized by rearrangements in the MLL-r gene such as MLL-r leukemia.

Genome browser tracks of MLL RNA are shown, with reads per million (rpm) indicated on the y axis. The SNPs N-terminal to the breakpoint of the MLL gene at chr11:118,317,907 (C>T) seen in SEM cells and at chr11:118,320,259 (A>C) in MM6 cells are shown below each track, with the number of sequencing reads from each allele indicated. (C and D) Identification of UBE2O as an MLL-Inter-specific-interacting protein. (C) Halo-tagged MLL internal region (MLL-Inter) and C-terminal region (MLL-CT), both of which are missing in the MLL chimeras, were transiently transfected into HEK293 cells. MudPIT analysis identified the UBE2O as the most abundant protein specifically interacting with MLL-Inter. Interaction between UBE2O and MLL-Inter was confirmed by co-immunoprecipitation (D). (E) Ectopic expression of UBE2O induces MLL degradation. HEK293 cells were transfected with increasing amounts of Myc-UBE2O expression plasmid; 24 hr later, cells were treated with DMSO or MG132 for 12 hr. (F) Depletion of UBE2O specifically stabilizes wild-type MLL, but not the MLL chimera MLL-AF9. UBE2O was depleted with two independent shRNAs in FLAGMLL-AF9 HEK293 cells; 4 days after infection, the MLL N320 and MLL-AF9 levels were determined with the D2M7U antibody. See also FIG. 8.

Figure 2:
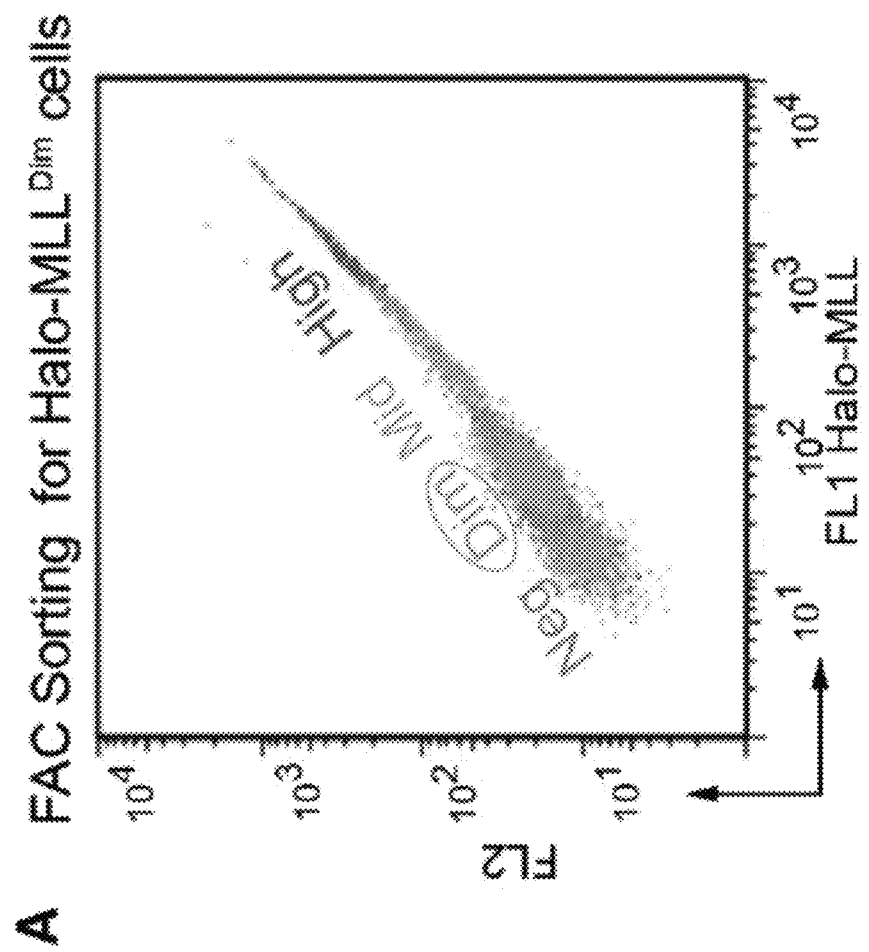
Figure 2:
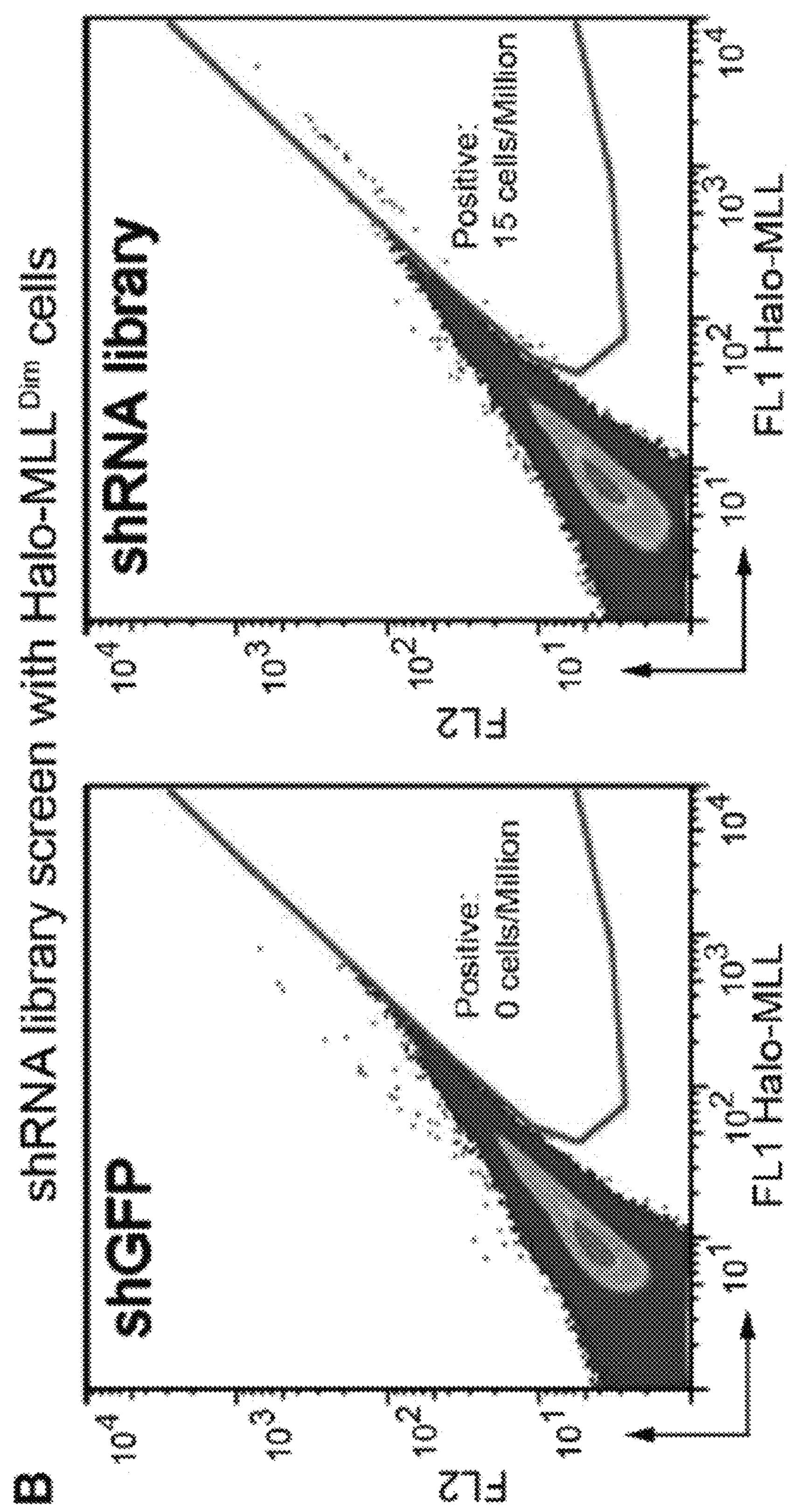
Figure 2:
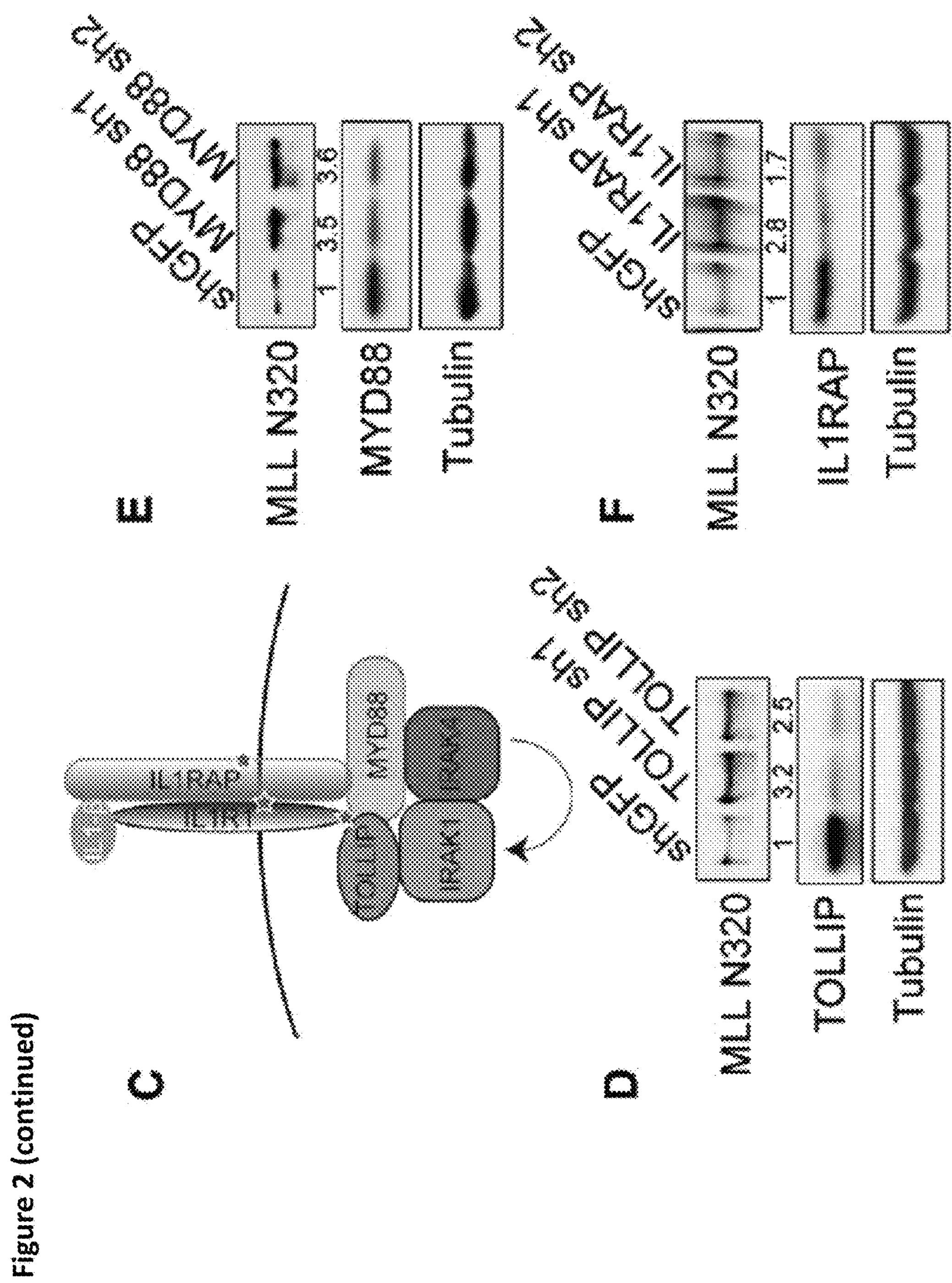
Figure 2:
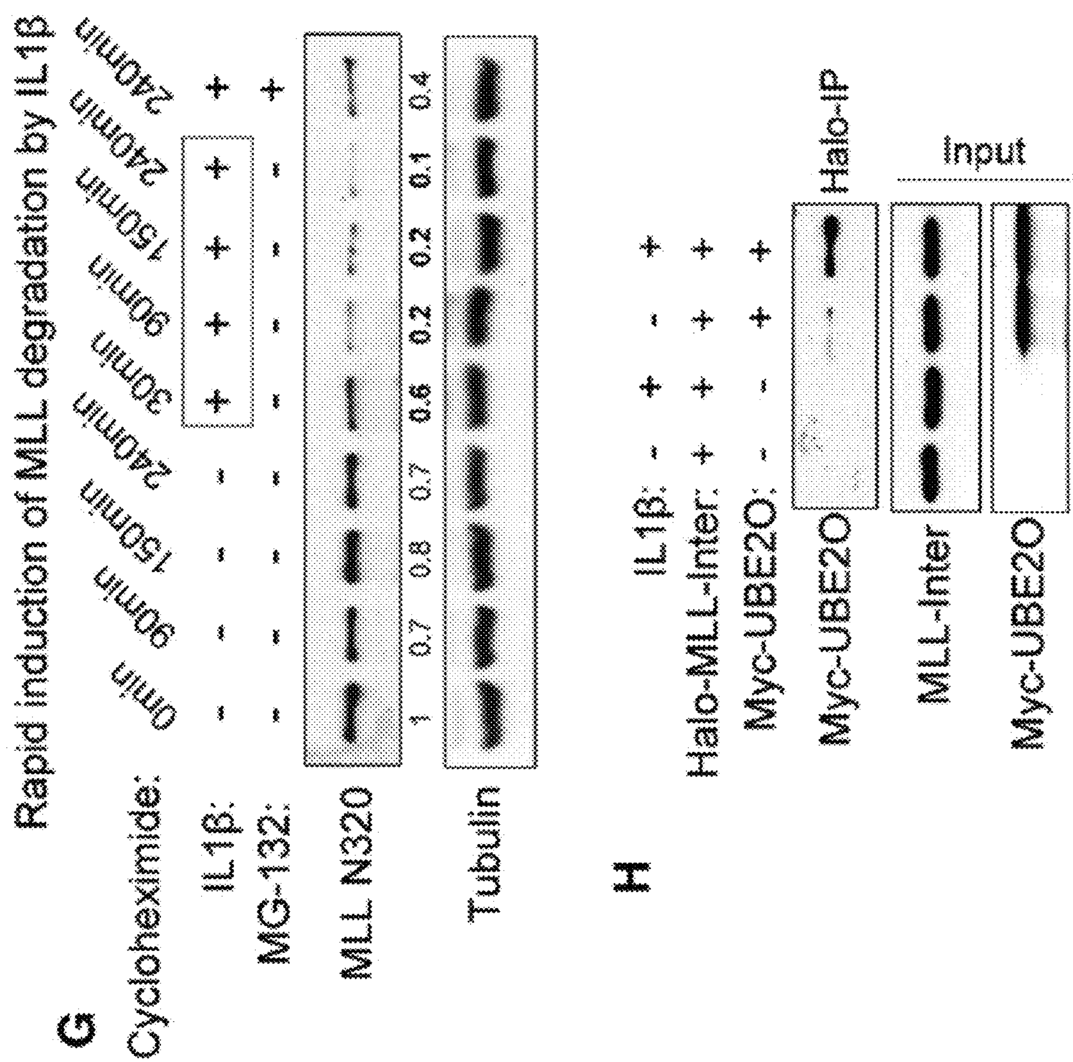
Figure 2:
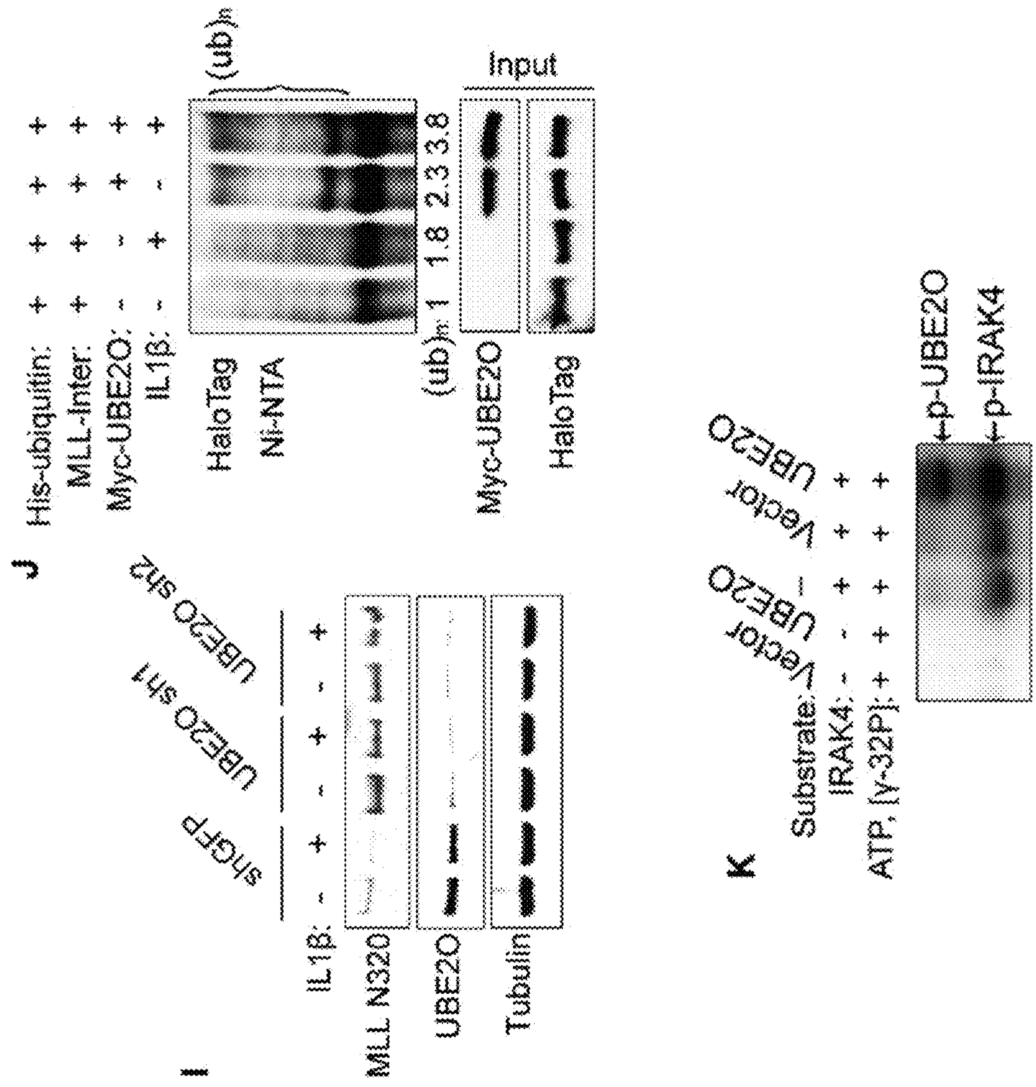

FIG. 2. Genome-wide shRNA Screen Identifies the IL-1 Pathway in Promoting MLL Degradation through an MLL-UBE2O Interaction (A) Stably transfected, randomly integrated Halo-MLL HEK293 cells were stained with HaloTag R110 ligand and sorted by flow cytometry to get the low-expressing (Halo-MLLDim) Halo-MLL cells. (B) Representative sort for shGFP and TRC lentiviral library-infected Halo-MLLDim cells. Halo-MLLDim cells were infected with lentiviral shRNA libraries or shGFP. Flow cytometry sorting was performed to obtain cells with increased Halo-MLL expression. Gating for cells with increased HaloTag R110 signal is indicated in pink. (C) Identification of the IL-1 pathway in the shRNA screen. Components of the IL-1 pathway, including IL1R1, IL1RAP, and TOLLIP, were represented in the 303 enriched genes and are indicated with a red star. (D-F) Knockdown of IL-1 pathway components TOLLIP (D), MYD88 (E), AND IL1RAP (F) increases endogenous MLL protein. Knockdown of IL-1 pathway components and changes in MLL N320 protein levels were determined by western blotting. Fold changes of MLL N320 protein relative to shGFP are indicated. Tubulin serves as a loading control. (G) IL-1b rapidly induces MLL N320 degradation in 293C6 cells, which have ectopically expressed IL-1 receptors IL1R and IL1RAP. 293C6 cells were stimulated with PBS or 50 ng/mL IL-1b for the indicated time. MG-132 was added prior to IL-1b induction. Fold changes relative to 0 min are indicated. (H) IL-1b increases MLL-UBE2O interaction. Halo-MLL-Inter and Myc-UBE2O plasmids were cotransfected into 293C6 cells; 24 hr later, these cells were stimulated with IL-1b for 30 min in the presence of MG-132 before MLL purification with HaloLink resin. Myc-UBE2O was detected with anti-Myc antibody and the inputs were blotted with anti-HaloTag and anti-Myc antibodies. (I) UBE2O depletion disrupts IL-1b-induced MLL degradation. After UBE2O depletion for 4 days, 293C6 cells were stimulated with 50 ng/mL IL-1b for 90 min. (J) IL-1b stimulates UBE2O-mediated MLL-Inter ubiquitination. His-tagged ubiquitin, Myc-UBE2O, and Halo-MLL-Inter plasmids were cotransfected into 293C6 as indicated; 24 hr later, these cells were stimulated with IL-1b for 45 min in the presence of MG-132. His-tagged ubiquitinated proteins were purified with Ni-NTA agarose and blotted with anti-HaloTag antibody. (K) IRAK4 directly phosphorylates UBE2O in vitro. 100 ng IRAK4 was incubated with eluates (purified from either vector or FLAG-UBE2O-transfected HEK293 cells) in the presence of g-32P ATP. The phosphorylated IRAK4 and UBE2O proteins were visualized by autoradiography. See also FIG. 9.

Figure 3:
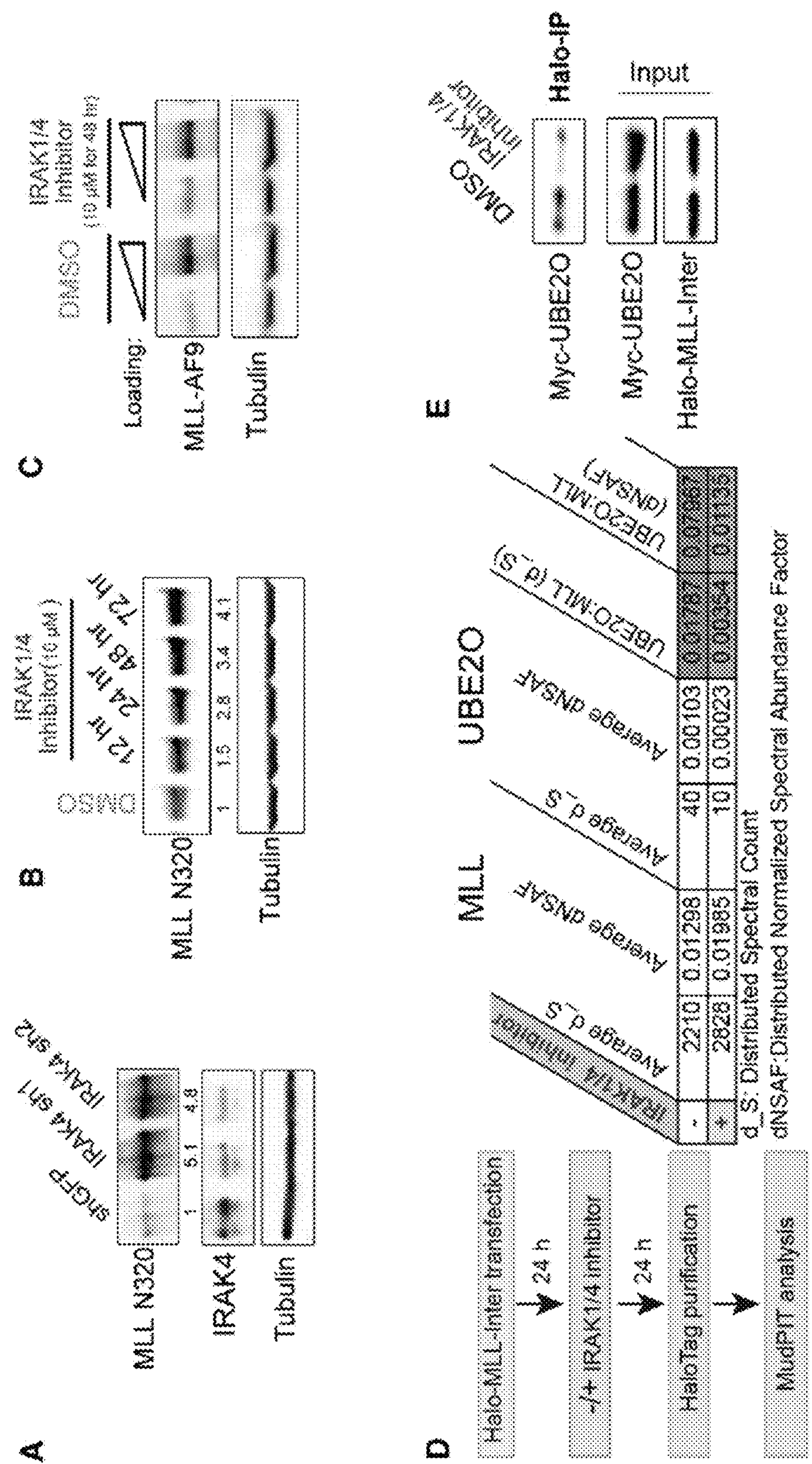
Figure 3:
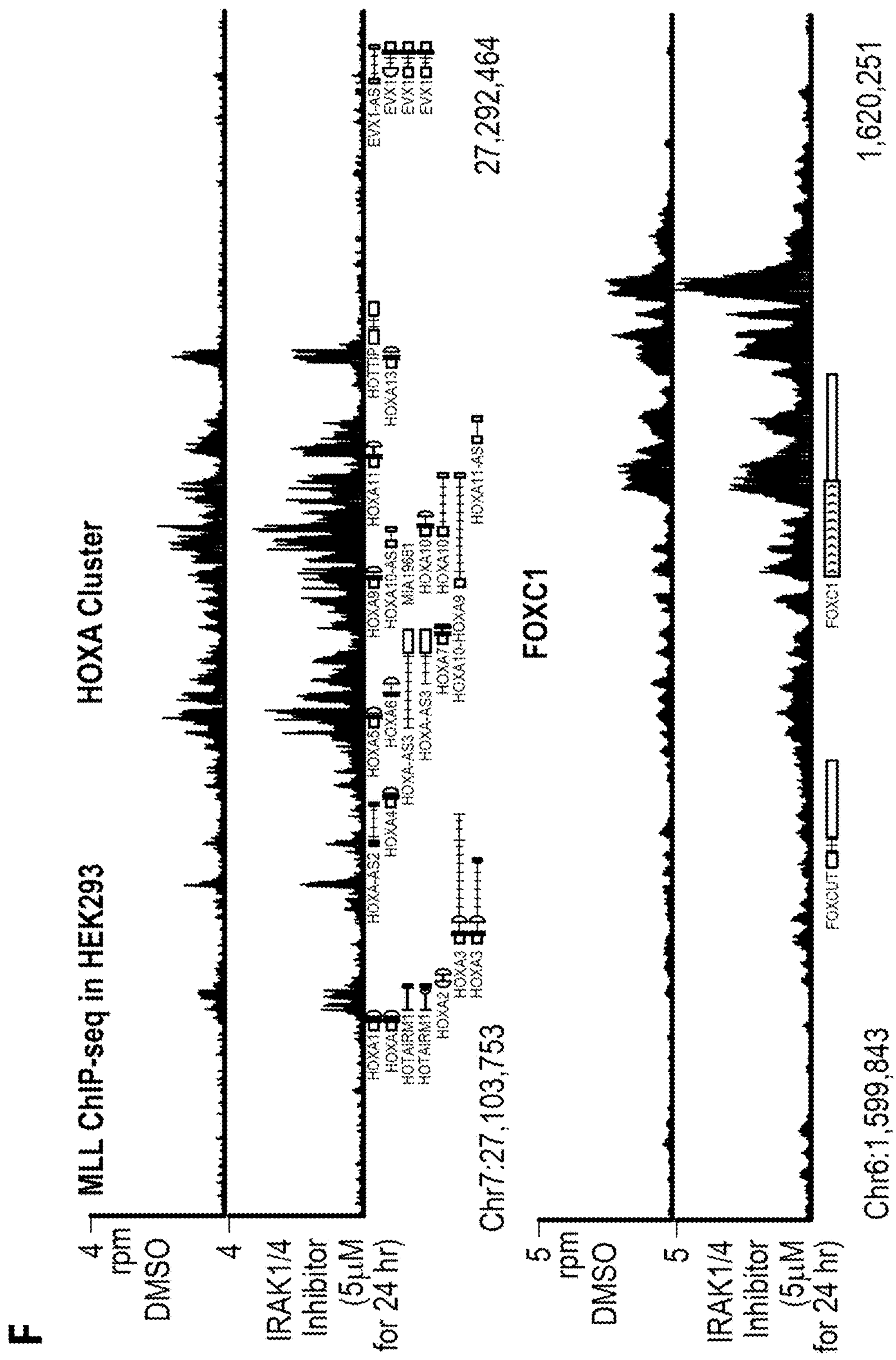
Figure 3:
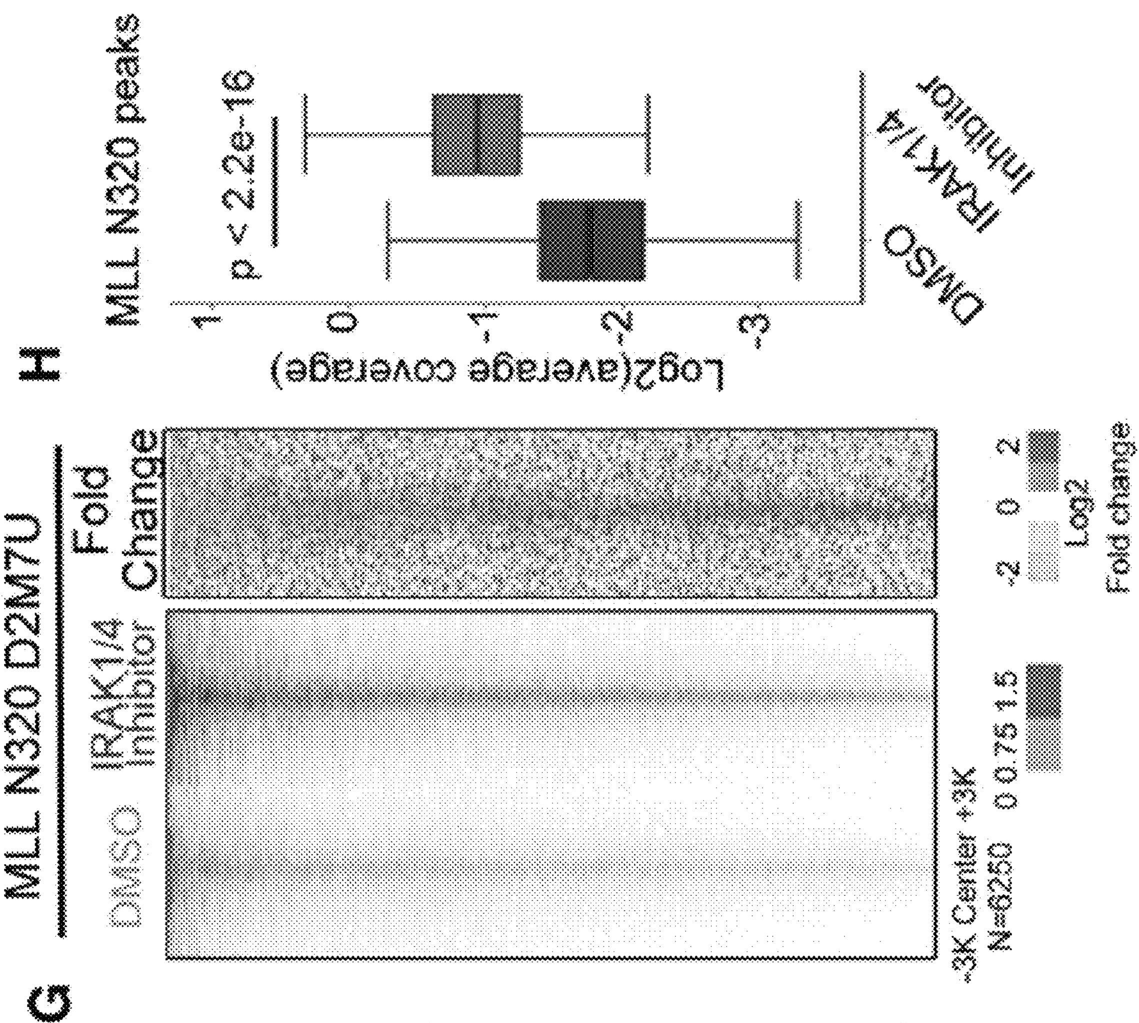

FIG. 3. IRAK Inhibition Stabilizes MLL Protein and Increases Genome-wide MLL Occupancy (A) IRAK4 knockdown leads to increased levels of endogenous MLL protein in HEK293 cells. Fold changes of MLL N320 protein relative to shGFP are indicated. (B) IRAK1/4 inhibitor stabilizes endogenous MLL protein. HEK293 cells were treated with 10 mM IRAK1/4 inhibitor for the indicated times. Fold changes of MLL N320 protein relative to vehicle (DMSO) are indicated. (C) IRAK1/4 inhibitor has no obvious effect on MLL-AF9 stabilization. FLAG-MLL-AF9 HEK293 cells were treated with 10 mM IRAK1/4 inhibitor for 2 days and subjected to western blotting with the FLAG monoclonal antibody. (D and E) IRAK1/4 inhibitor decreases MLL-UBE2O interaction. (D) Halo-MLL-Inter-transfected HEK293 cells were treated with 10 mMIRAK1/4 inhibitor for 24 hr, purified with HaloLink resin, and subjected to MudPIT analysis. (E) Confirmation of the decreased interaction between MLL-Inter and UBE2O upon IRAK1/4 inhibition by coimmunoprecipitation. (F) Genome browser tracks of MLL-N320 D2M7U ChIP-seq at HOXA and FOXC1 loci after DMSO or IRAK1/4 inhibitor treatment for 24 hr. IRAK1/4 inhibitor increases MLL occupancy at HOXA and HOXC loci. (G) Heatmap analysis of MLL occupancy after IRAK1/4 inhibitor treatment in HEK293 cells. Each row represents a peak of MLL occupancy (n=6,250), with rows ordered by decreasing MLL occupancy in the inhibitor-treated condition. (H) MLL occupancy is significantly increased after IRAK1/4 inhibitor treatment. Boxplots depict the read coverage for all MLL peaks. The p value was calculated with the Wilcoxon signed-rank test. See also FIG. 10.

Figure 4:
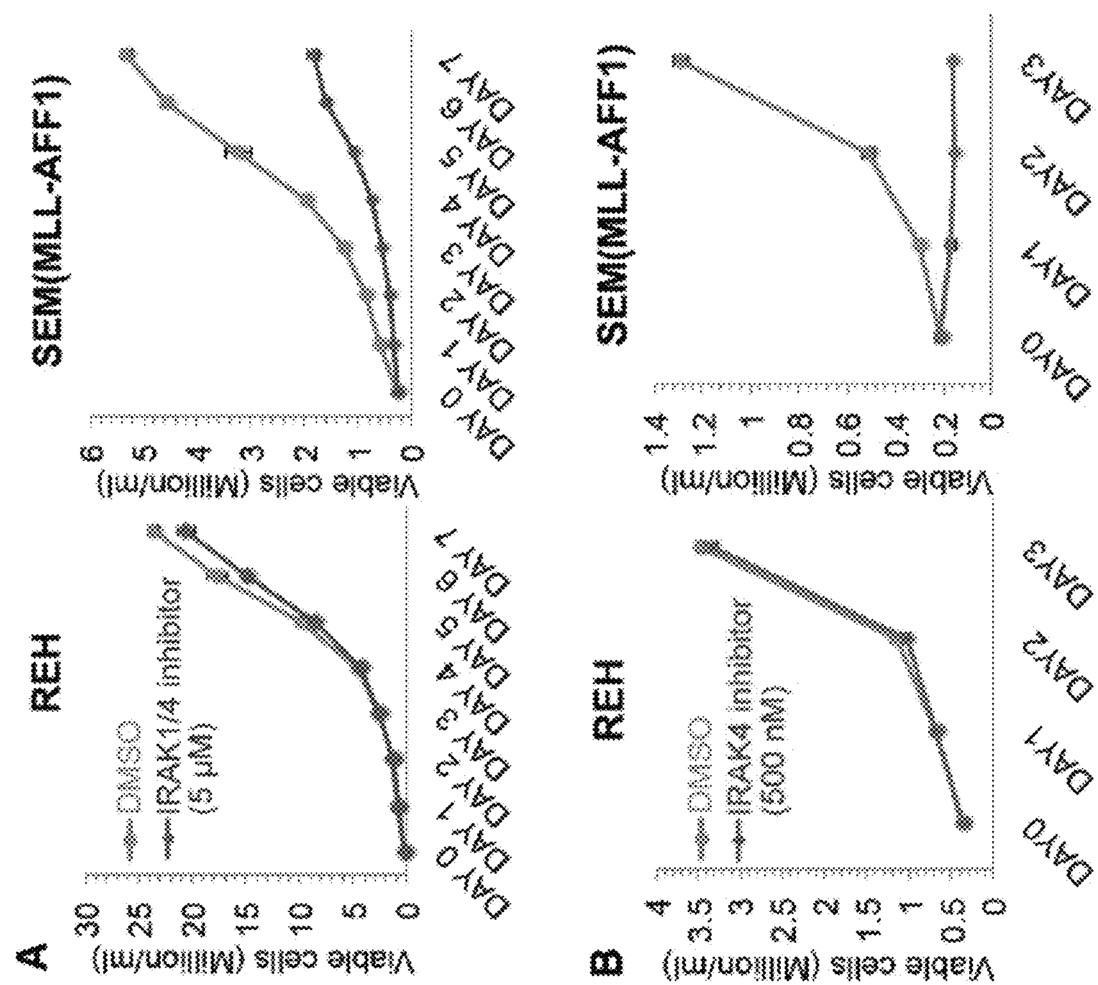
Figure 4:
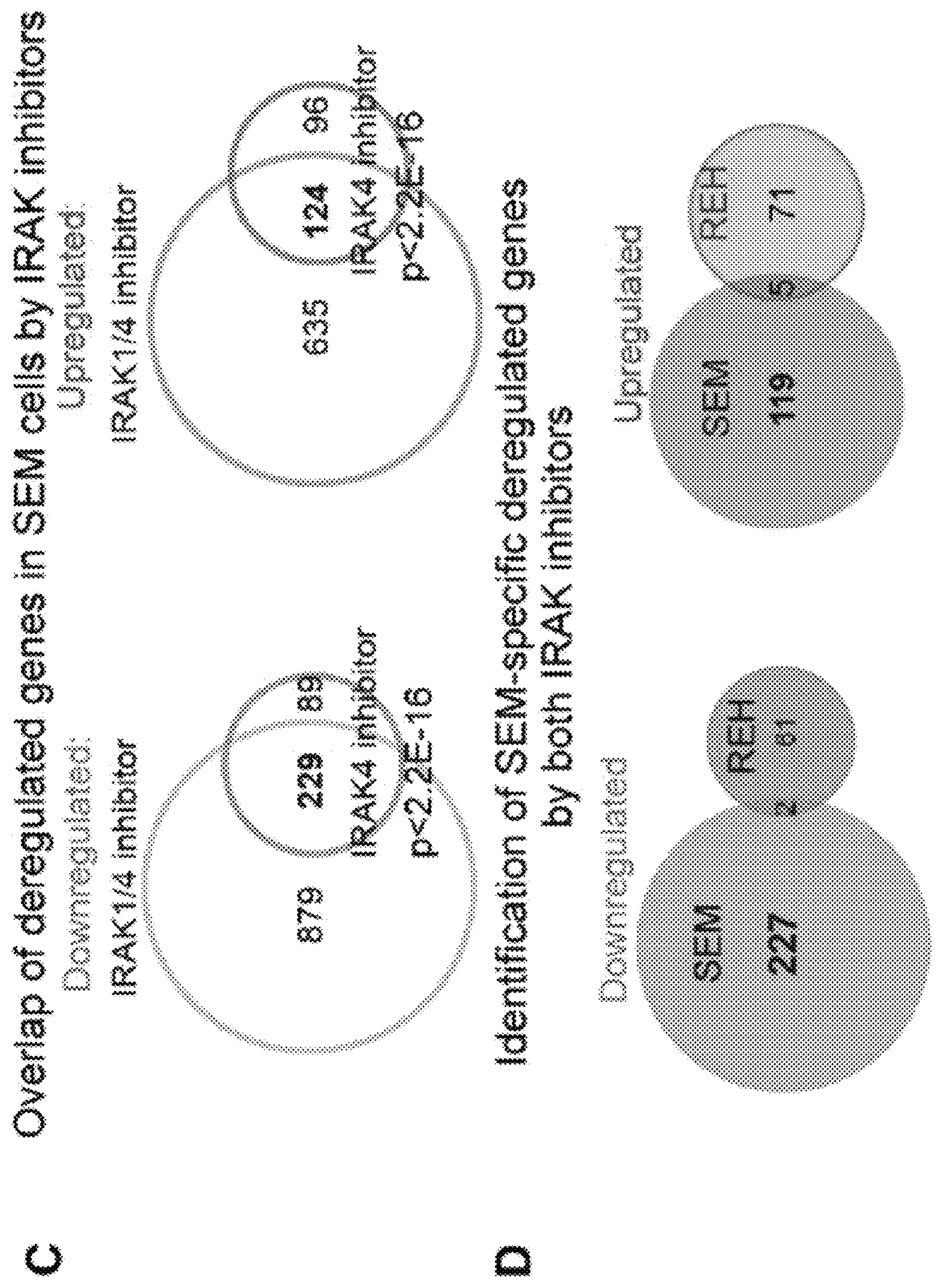
Figure 4:
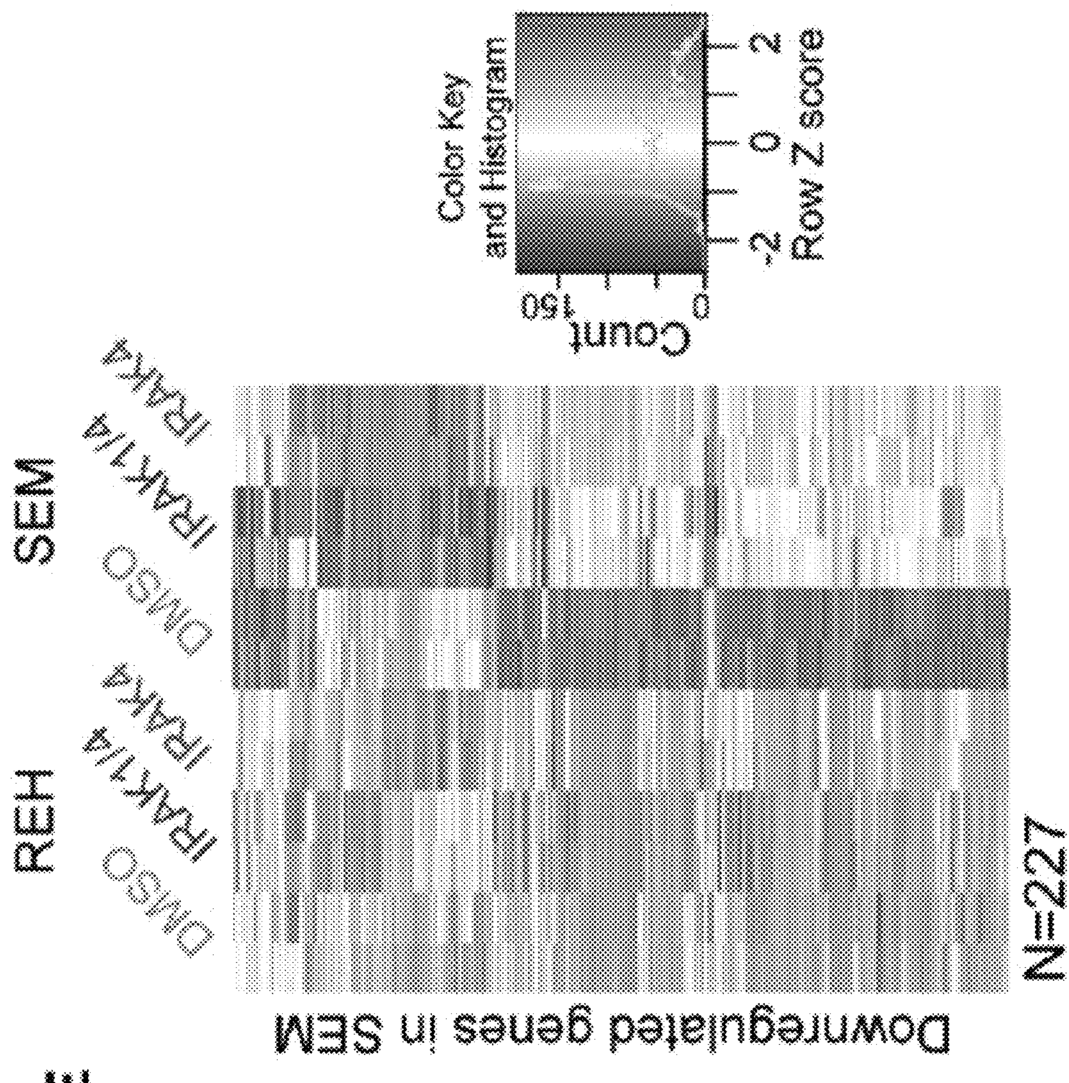
Figure 4:
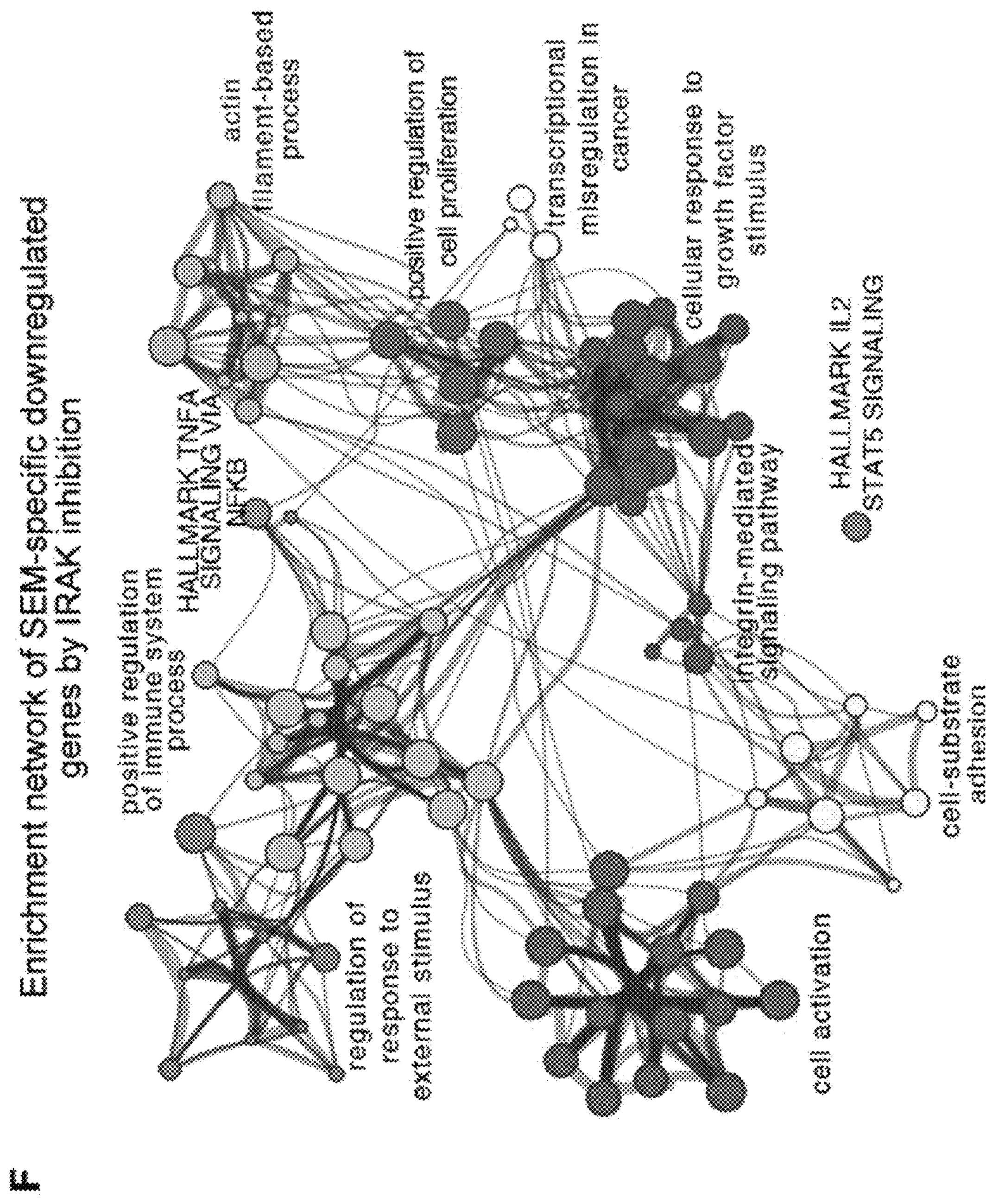
Figure 4:
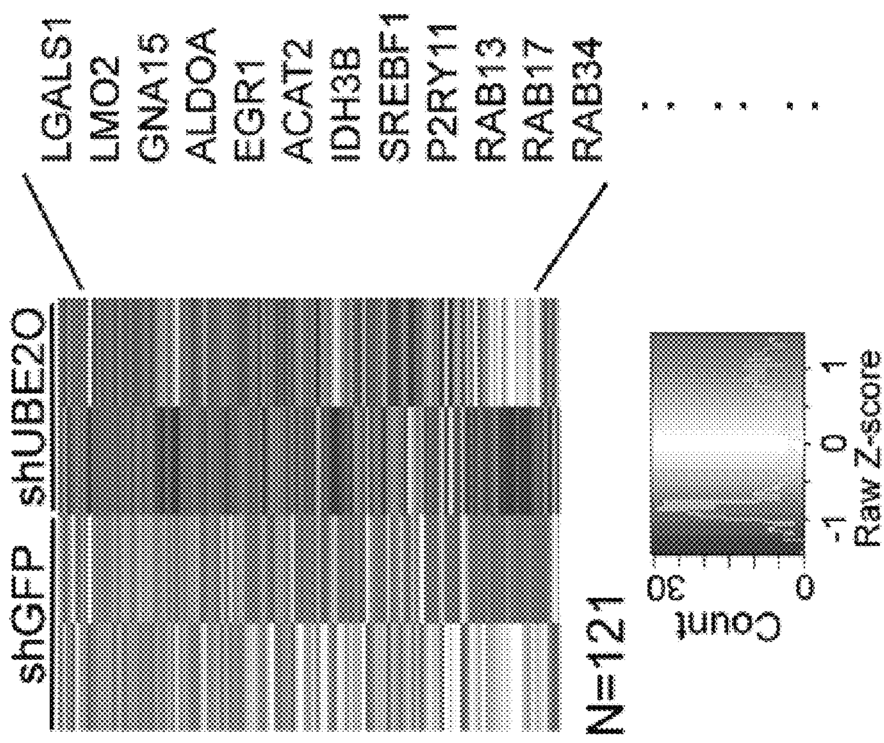

FIG. 4. Stabilization of MLL through IRAK Inhibition or UBE2O Depletion Impedes Cell Proliferation and Deregulates a Gene Regulatory Network in MLL Leukemia (A) IRAK1/4 inhibitor treatment results in slower growth of MLL leukemia SEM cells but has no effect on non-MLL leukemia REH cells. Viable cells were seeded at 0.2 million/mL, and they were monitored by trypan blue exclusion staining and counted using a Vi-CELL XR cell counter. Data are represented as mean±SD (n=3). (B) 500 nM IRAK4 inhibitor treatment blocks SEM cell growth, but not REH cell growth. Data are represented as mean±SD (n=3). (C) Venn diagram of deregulated genes in SEM cells by IRAK1/4 and IRAK4 inhibitors. 229 genes were downregulated and 124 genes were upregulated by both inhibitors. (D) Venn diagram of deregulated genes in SEM and REH cells by both inhibitors. Little overlap was observed between REH and SEM cells. (E) Hierarchical clustering of 227 genes specifically downregulated in SEM cells, but not REH cells, by both inhibitors. Heatmaps of Z score-normalized values are displayed. (F) Network enrichment analysis by Metascape (Tripathi et al., 2015) of the 227 genes downregulated only in SEM cells. Each cluster is represented by different colors and a circle node represents each enriched term. (G) UBE2O depletion and IRAK inhibition affect a common subset of genes in SEM cells. 121 of 227 genes downregulated by IRAK inhibition also are decreased after UBE2O knockdown. Some examples of common downregulated genes are indicated to the right. Heatmaps represent Z score-normalized values. See also FIG. 11.

Figure 5:
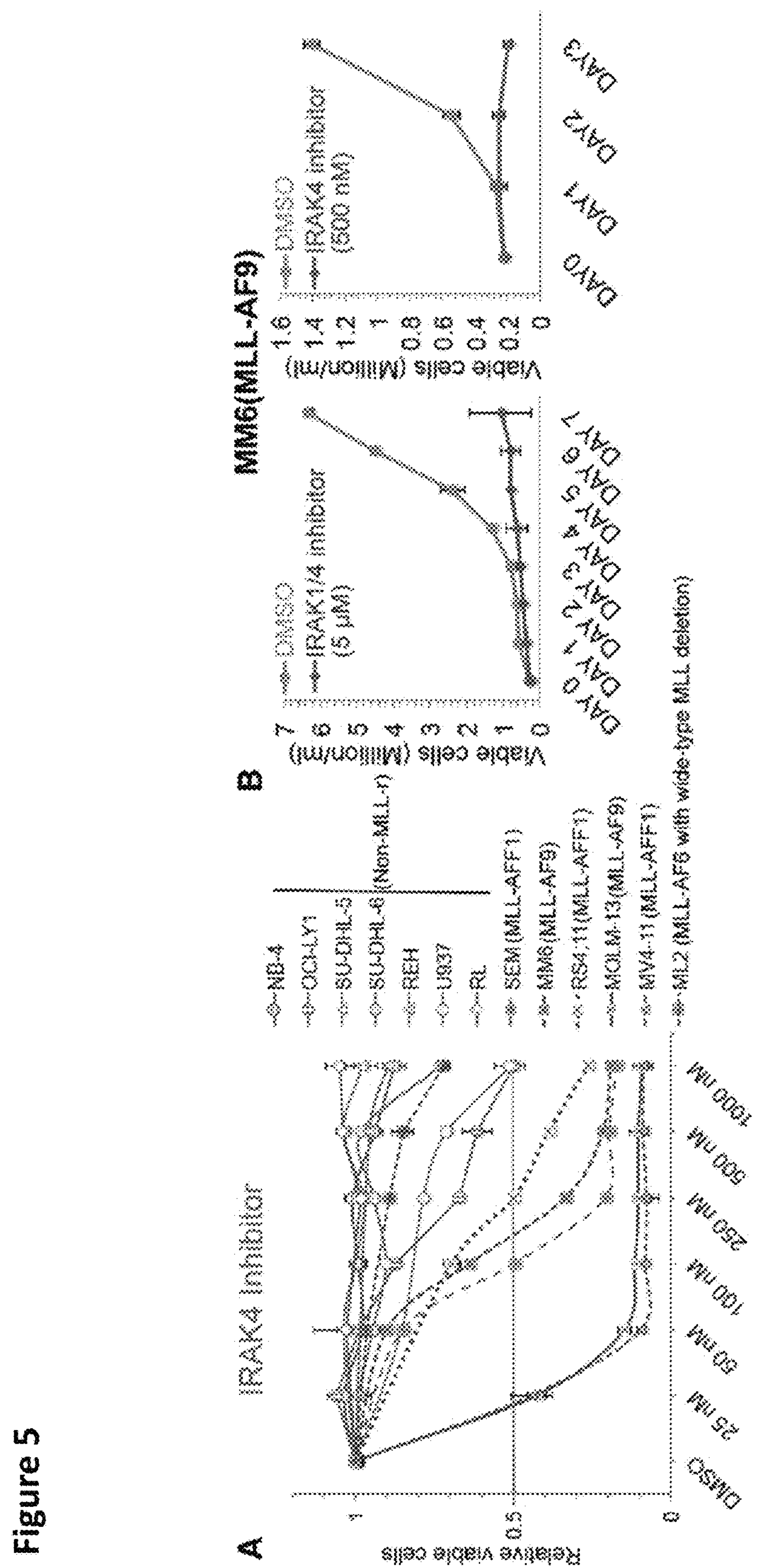
Figure 5:
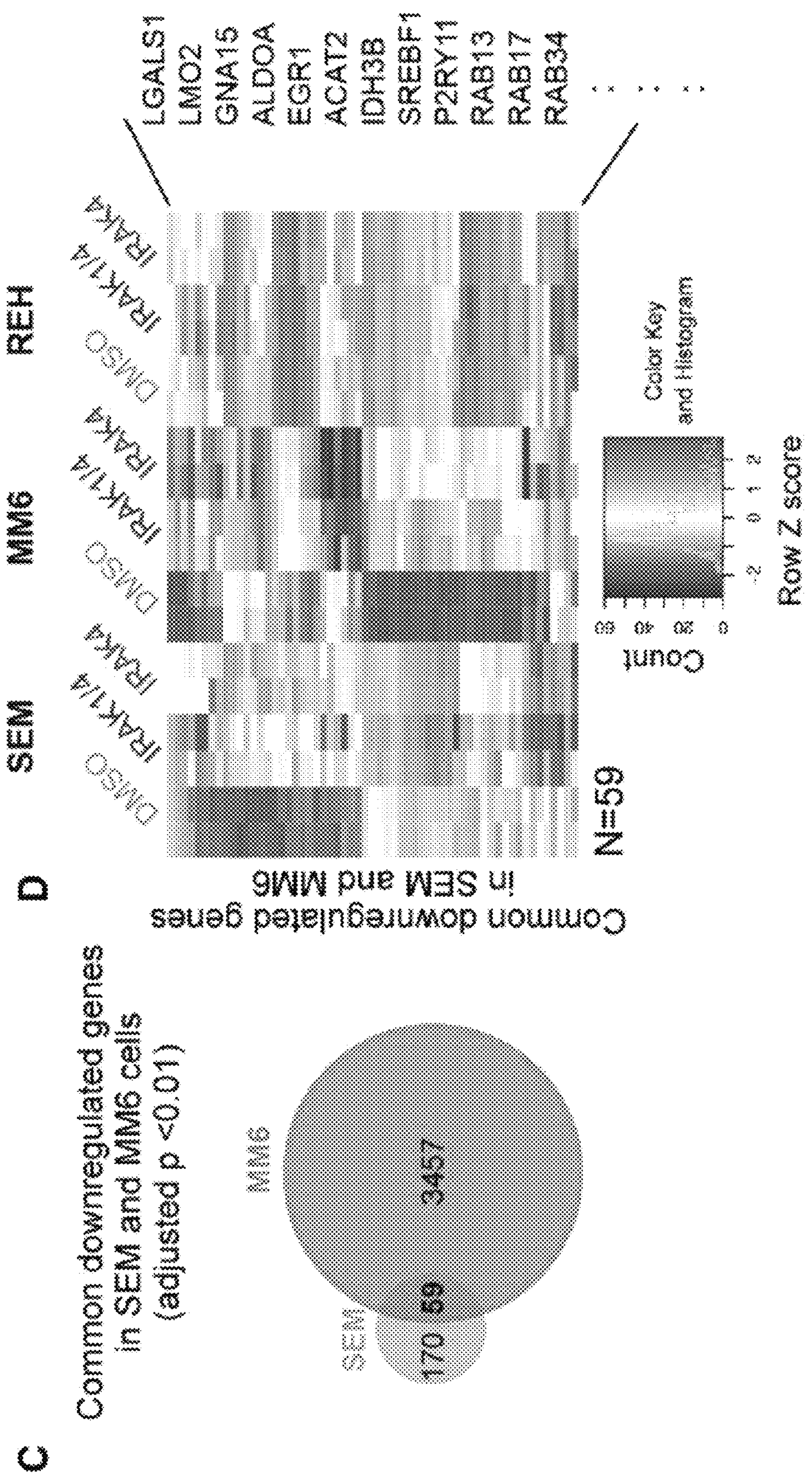
Figure 5:
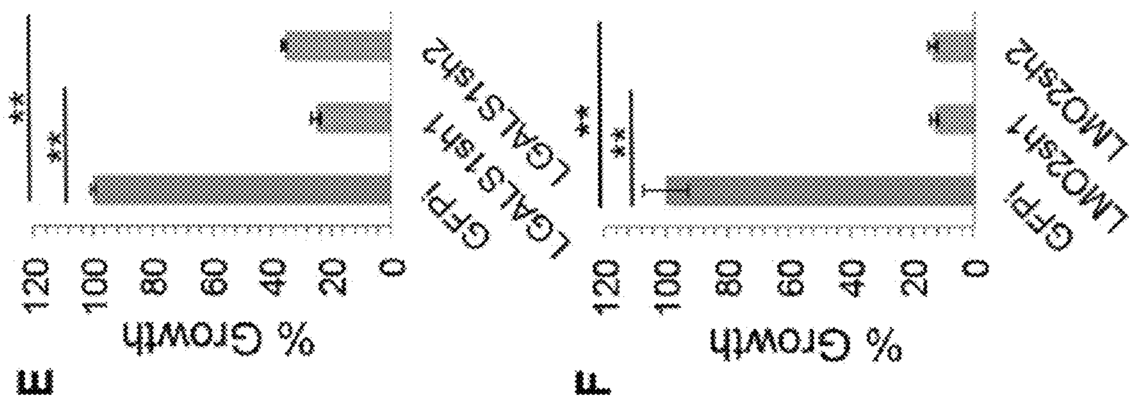

FIG. 5. Determinants of the Increased Sensitivity of MLL Leukemia Cells to IRAK Inhibition (A) IRAK4 inhibitor-specific inhibition of MLL leukemia cell proliferation. Multiple MLL leukemia and non-MLL leukemia or lymphoma cell lines were cultured with different doses of IRAK4 inhibitor for 3 days. Data are represented as mean±SD (n=3). (B) Cell growth of MLL-AF9-positive AML MM6 cells is inhibited by IRAK inhibition. Data are represented as mean±SD (n=3). (C) Venn diagram analysis identifies 59 common downregulated genes by both IRAK inhibitors in MLL-AFF1 SEM and MLL-AF9 MM6 cells. The p value was determined with the hypergeometric test. (D) Hierarchical clustering of the 59 common genes downregulated in SEM and MM6cells after IRAK inhibition. Some examples of common downregulated genes are indicated to the right. (E and F) Depletion of LGALS1 (E) and LMO2 (F) results in reduced growth of MM6 cells. MM6 cells were transduced with shGFP control (GFPi) or two different lentiviral shRNA constructs. After selection with puromycin for 4 days, viable cells were seeded at 0.2 million/mL and cultured for 3 more days before cell viability counting. Data represent the mean±SD (n=3; p<0.005, one-way ANOVA). See also FIG. 12**.

Figure 6:
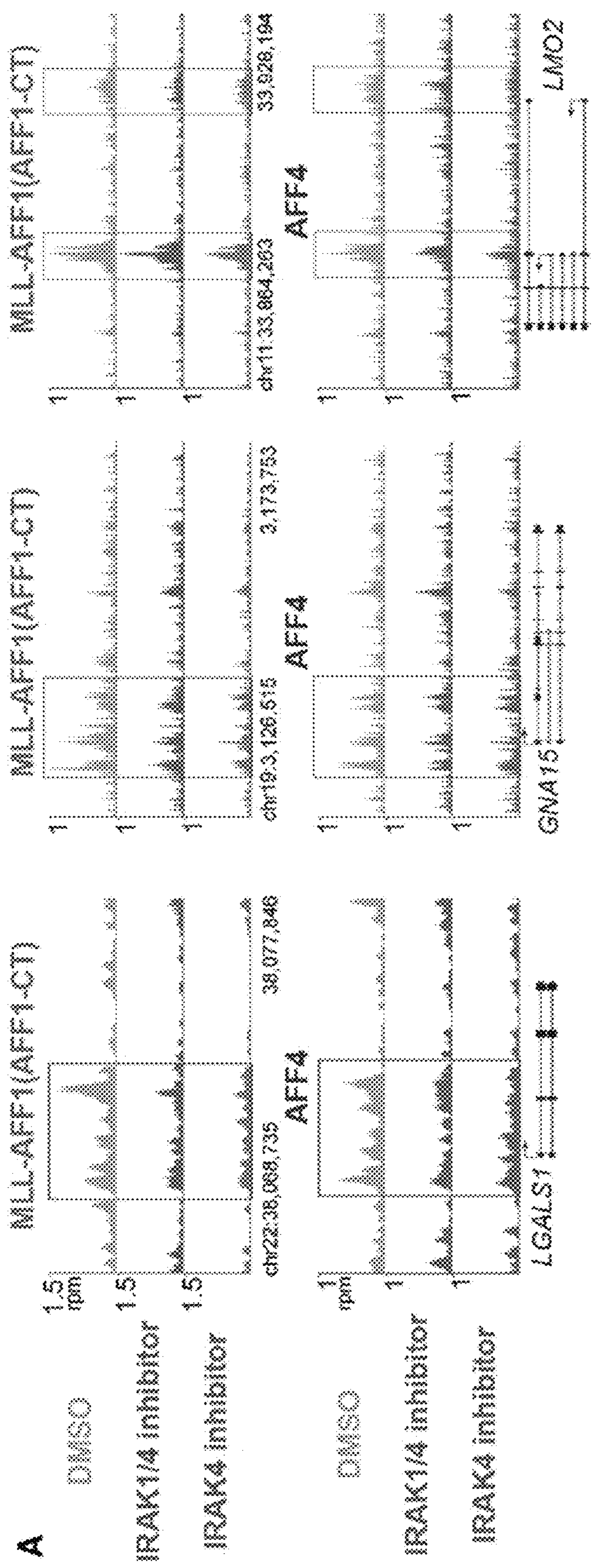
Figure 6:
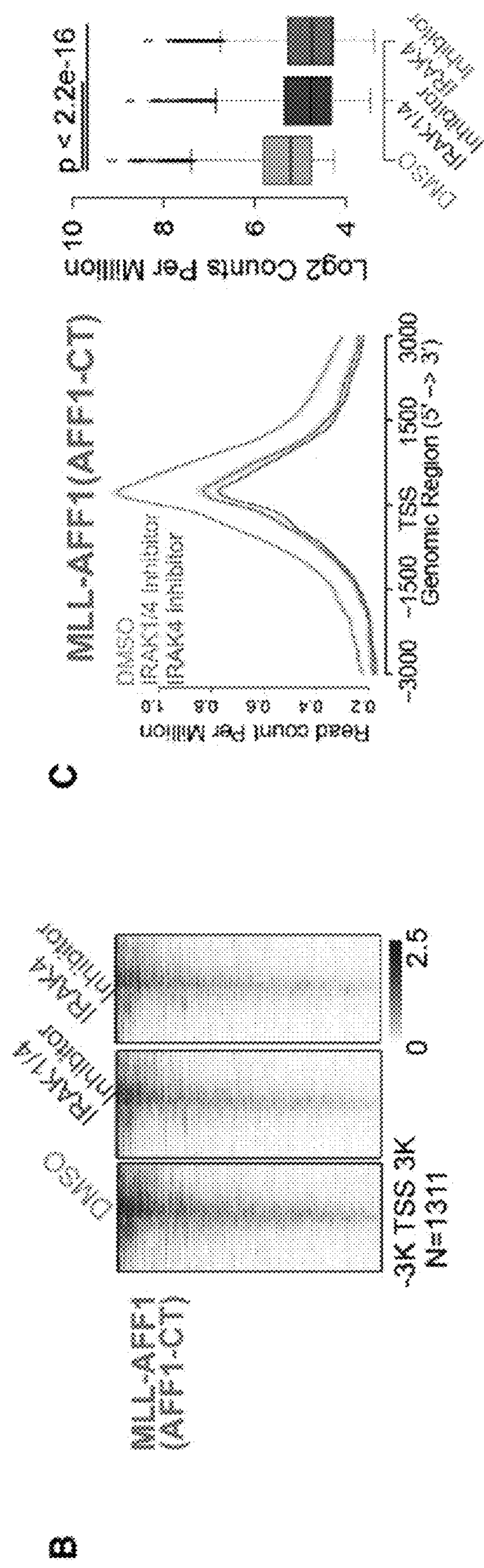
Figure 6:
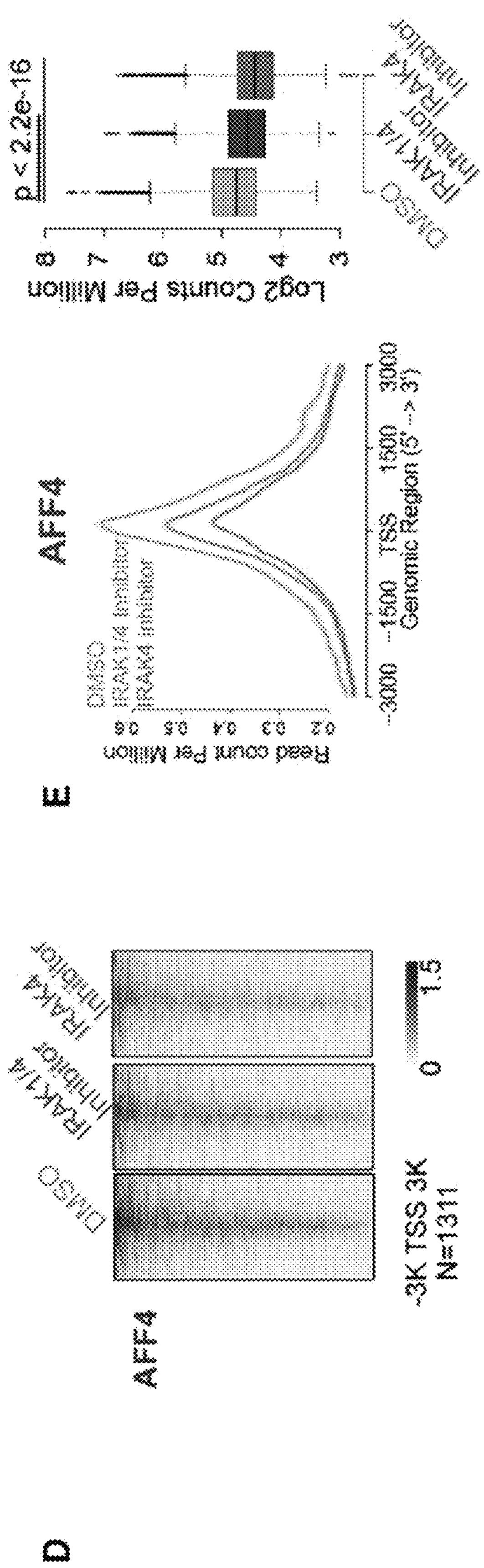
Figure 6:
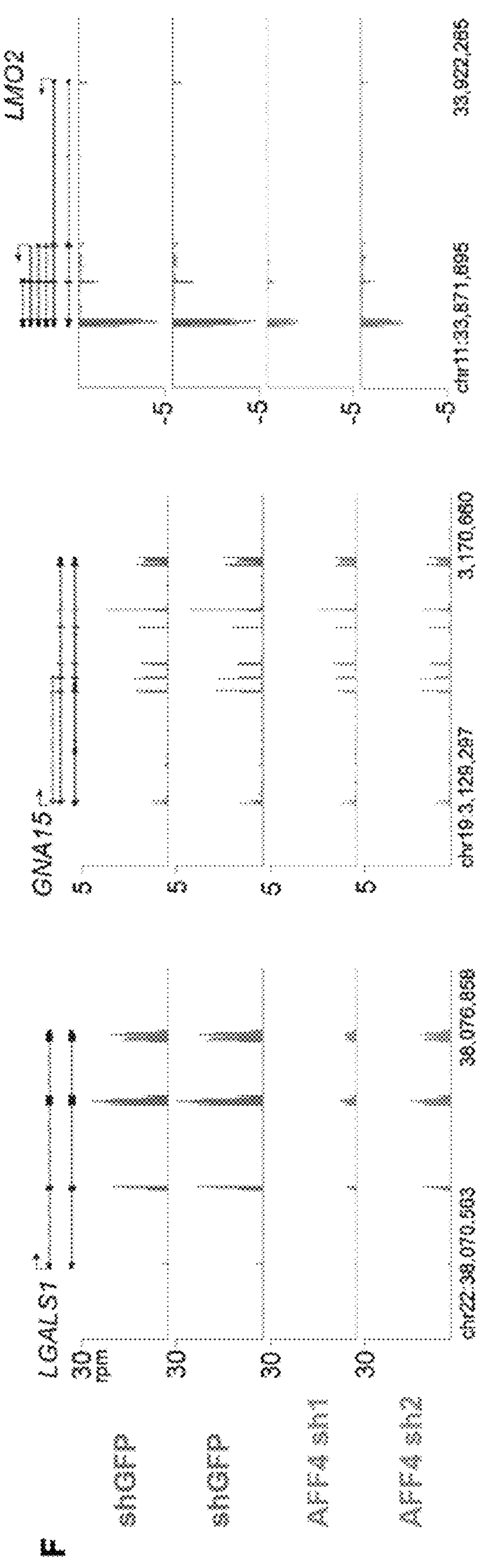

FIG. 6. IRAK Inhibition Displaces MLL Chimera and SEC Occupancy at a Subset of MLL Chimera and SEC Target Genes (A) IRAK inhibitors decrease MLL-AFF1 and SEC occupancy at the LGALS1, GNA15, and LMO2 genes in SEM cells. Genome browser views of MLL-AFF1 (AFF1-CT) and SEC component AFF4 occupancy at the LGALS1, GNA15, and LMO2 genes are shown. Red boxes indicate the promoter-proximal regions with decreased MLL-AFF1 and AFF4 occupancy. (B and C) We identified 1,311 promoter regions (±3 kb of the transcription start site [TSS]) in which MLL-AFF1 occupancy was altered by IRAK inhibitors. These regions are plotted as heatmaps (B) and metagene plots, and the Wilcoxon signed-rank test was used to show that MLL-AFF1 occupancy is significantly decreased after IRAK inhibition (C). (D and E) Heatmap (D), metagene, and statistical analysis (E) of AFF4 occupancy at the 1,311 promoter regions are shown. (F) RNA-seq genome browser track examples indicate that AFF4 knockdown reduces the expression of the LGALS1, GNA15, and LMO2 genes in SEM cells. See also FIG. 13.

Figure 7:
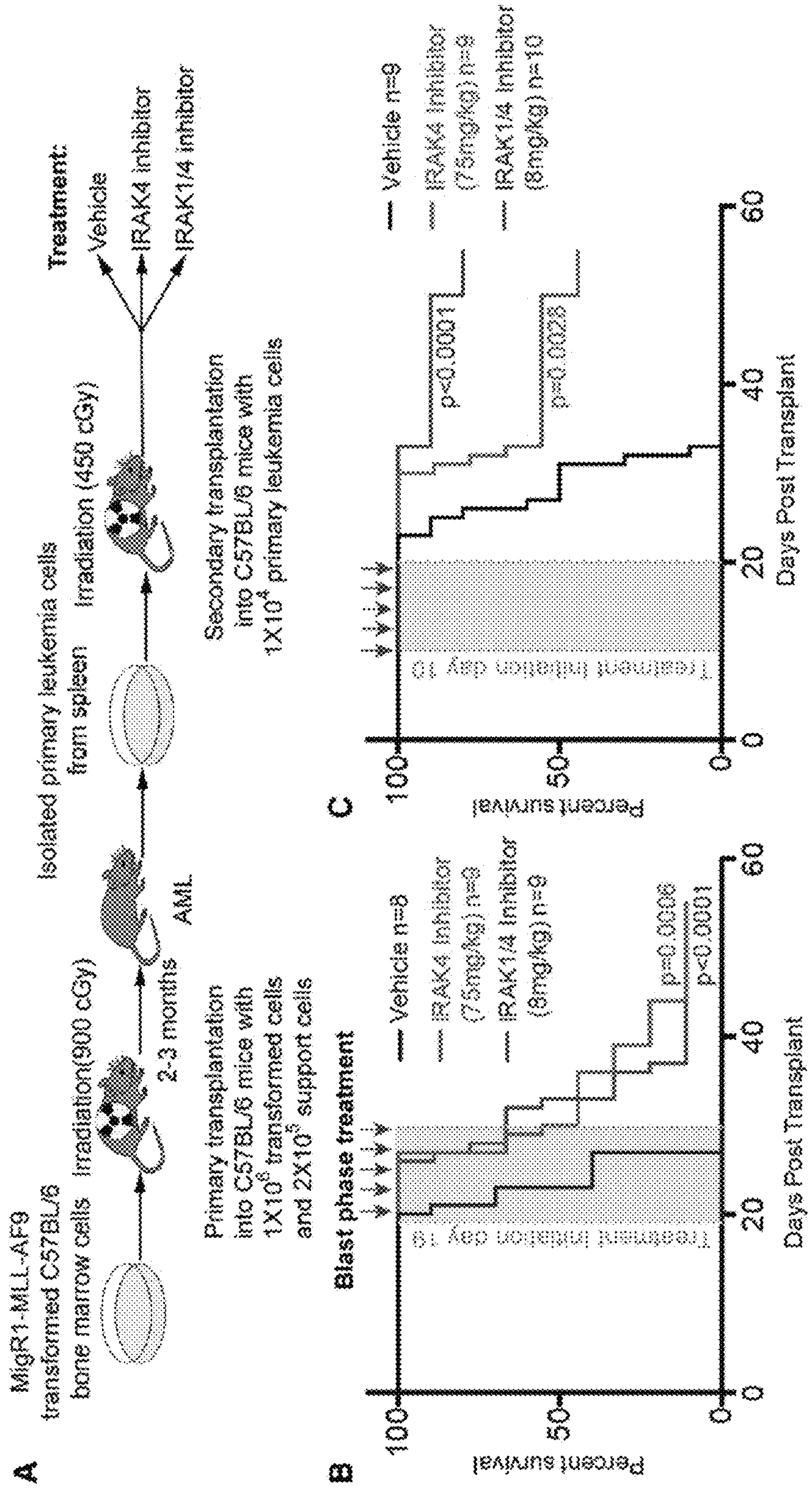
Figure 7:
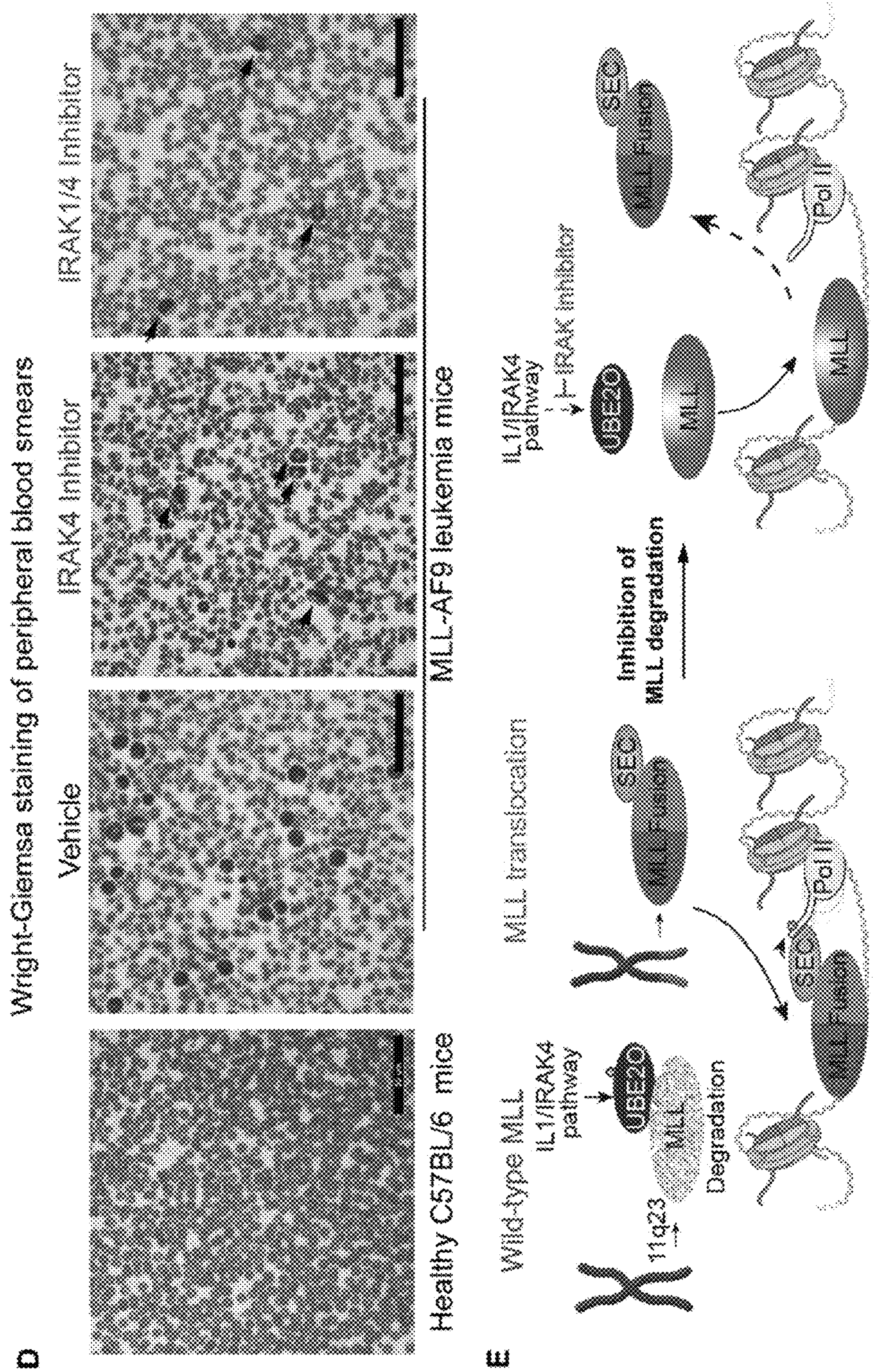

FIG. 7. IRAK Inhibition Substantially Delays Disease Progression and Improves Survival of MLL-AF9 Leukemia Mice (A) Schematic of the development of secondary murine MLL-AF9 leukemia. After transformation of MLL-AF9, c-Kit+ HSPCs were transplanted into lethally irradiated C57BL/6 mice with 1 3 106 transformed cells and 2 3 105 support cells. Leukemia cells from primary AML mice were isolated and transplanted into sublethally irradiated C57BL/6 mice. Drug treatments were started at day 10 or 19 after transplantation. (B) Kaplan-Meier survival curves of secondary transplanted C57BL/6 mice after vehicle and IRAK1/4 or IRAK4 inhibitor treatment at day 19 (blast phase). Vehicle or IRAK inhibitors were administered every other day by intraperitoneal injection for a total of five treatments. Leukemia was confirmed at the endpoint for each transplant mouse. The number (n) indicates the number of mice in each group. The p values were calculated using the log rank test. (C) Kaplan-Meier survival curves of vehicle- and IRAK1/4 or IRAK4 inhibitor-treated C57BL/6 mice transplanted with 1 3 104 primary MLL-AF9 leukemia cells. 10 days after transplantation, vehicle or IRAK inhibitors were administered every other day by intraperitoneal injection for a total of five treatments. The p values were calculated using the log rank test. (D) Wright-Giemsa staining of peripheral blood smears from vehicle- and IRAK inhibitor-treated leukemic mice at the endpoint. Arrows indicate partially differentiated MLL-AF9 blast cells after IRAK inhibition.

Figure 1:
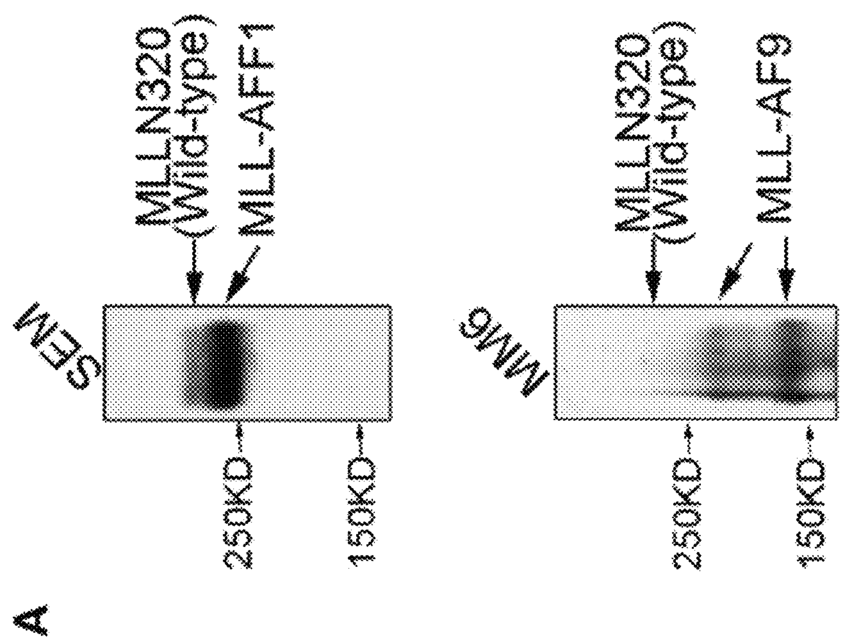
FIG. 1. UBE2O Interacts with an MLL Internal Region and Promotes Wild-Type MLL Protein Degradation (A) MLL-rearranged leukemia cell lines SEM (MLL-AFF1) and MM6 (MLL-AF9) have relatively low levels of wild-type MLL protein compared to the MLL chimeras. Immunoblotting of MLL N320 with the D2M7U monoclonal antibody was performed with total cell lysates of SEM and MM6 cells. (B) Wild-type MLL and MLL fusion alleles are transcribed at similar levels in SEM and MM6 cells. Total RNA-seq was performed with SEM and MM6 cells.
Figure 1:
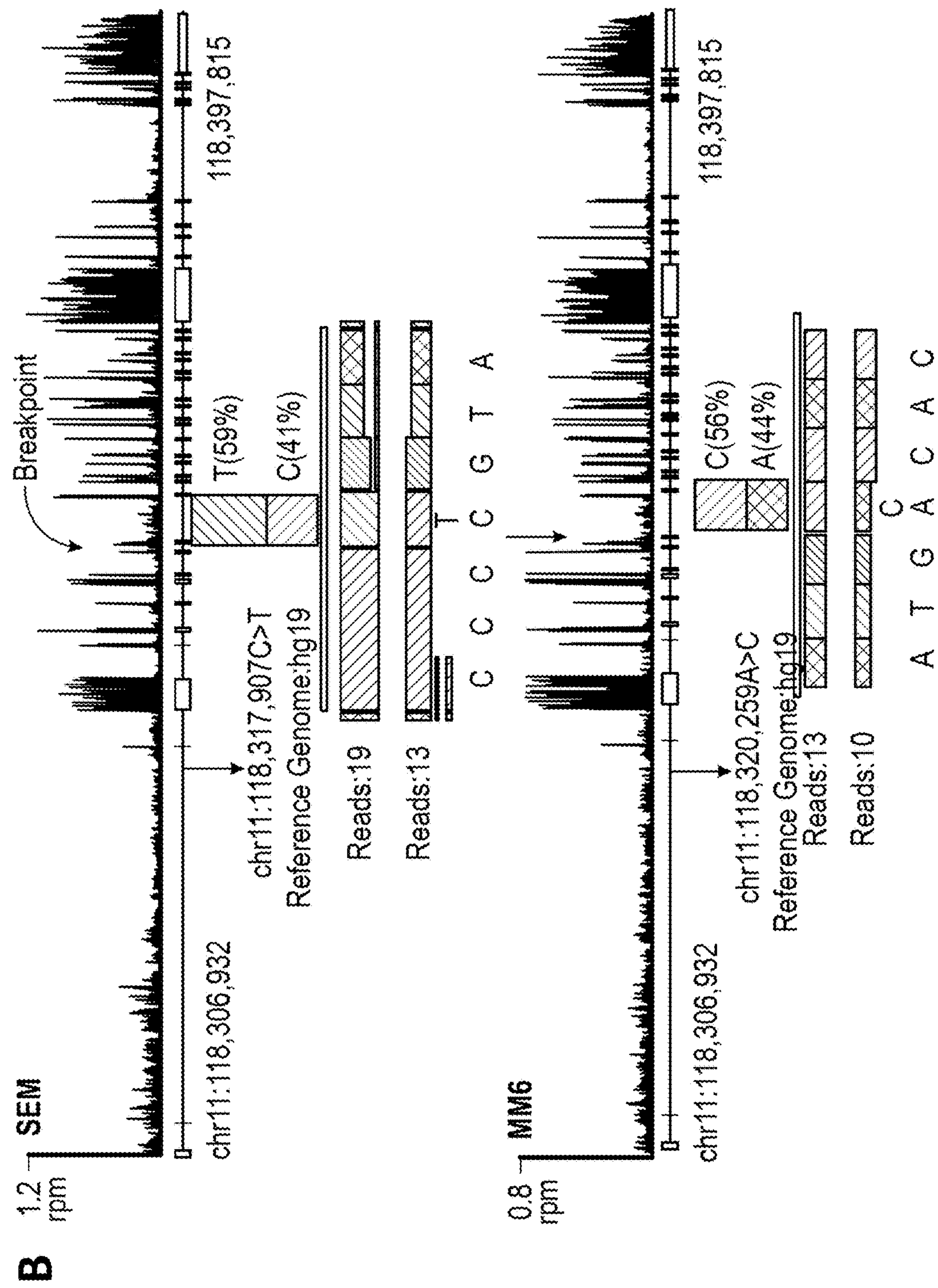
Figure 1:
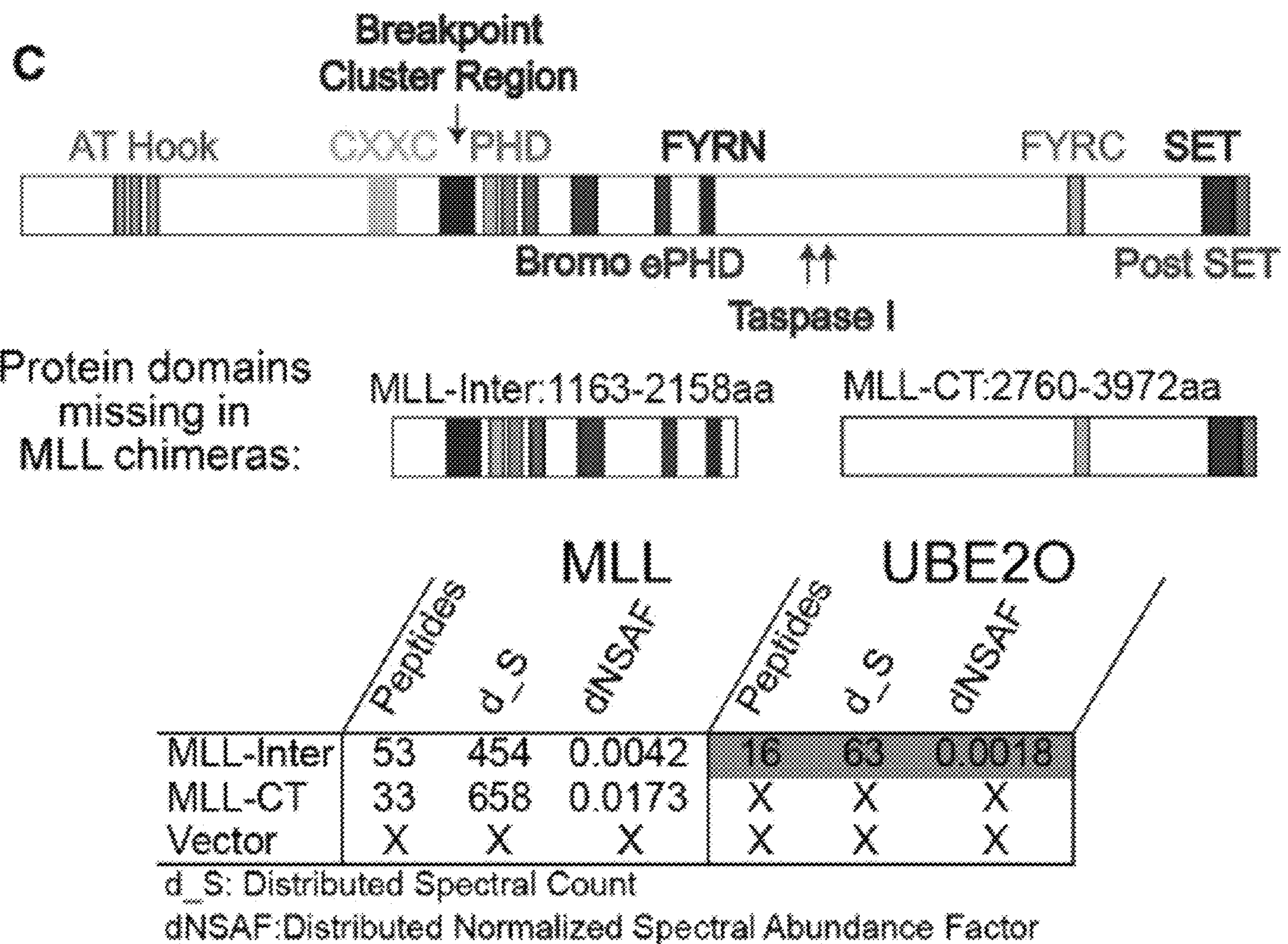
Figure 1:
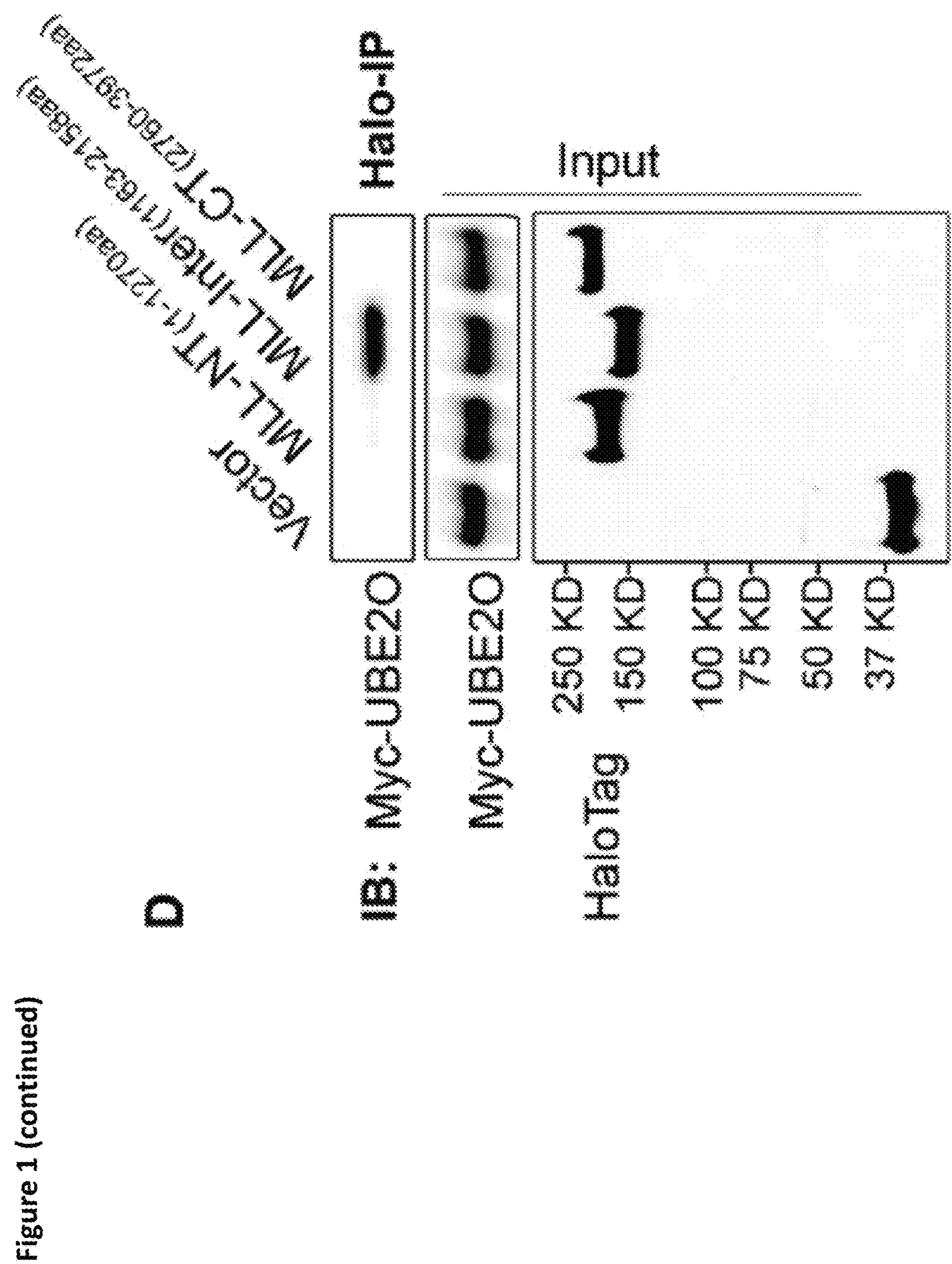
Figure 1:
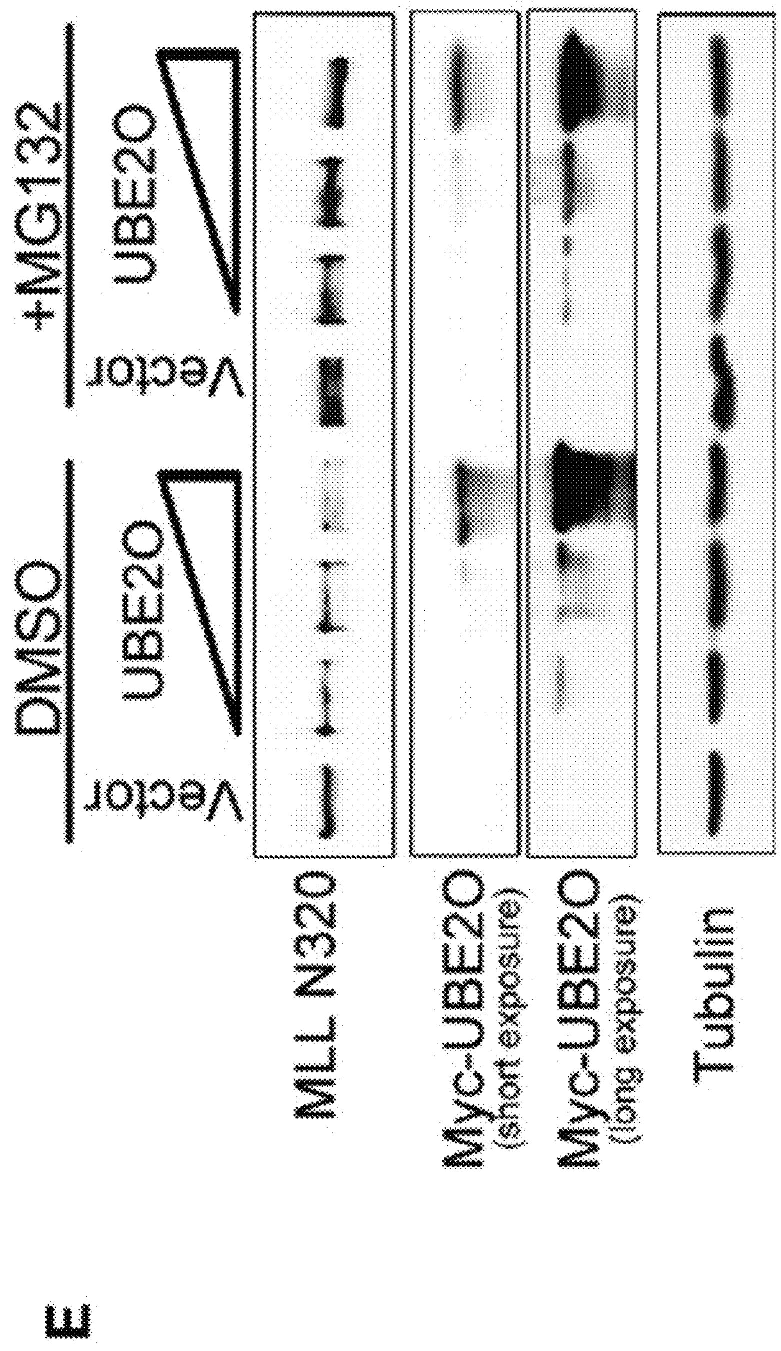
Figure 1:
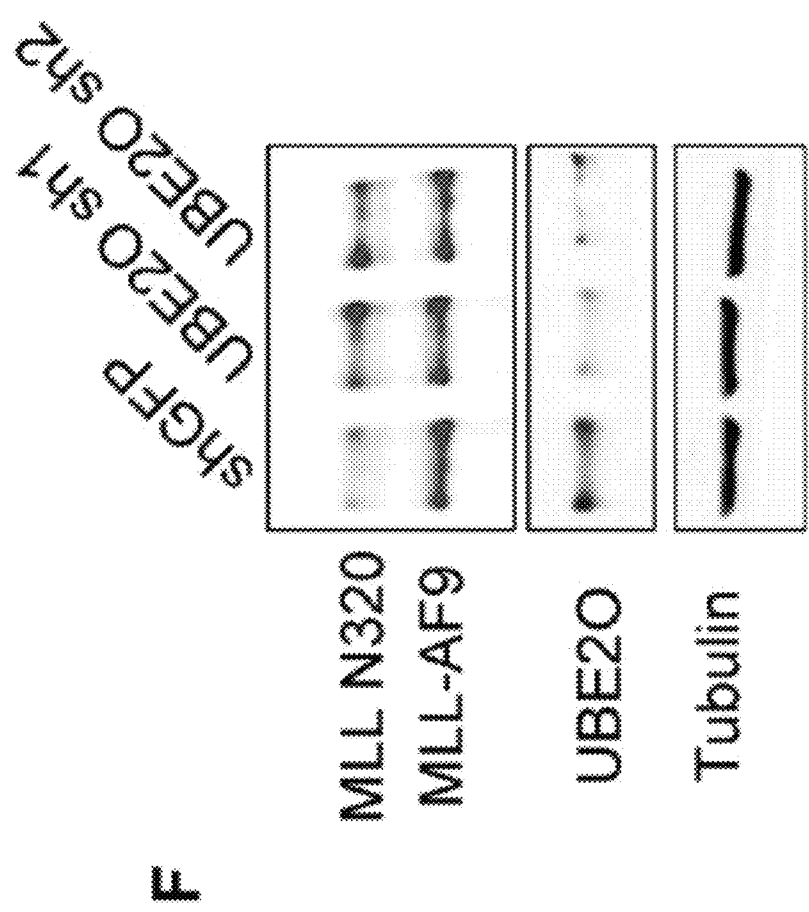
Figure 8:
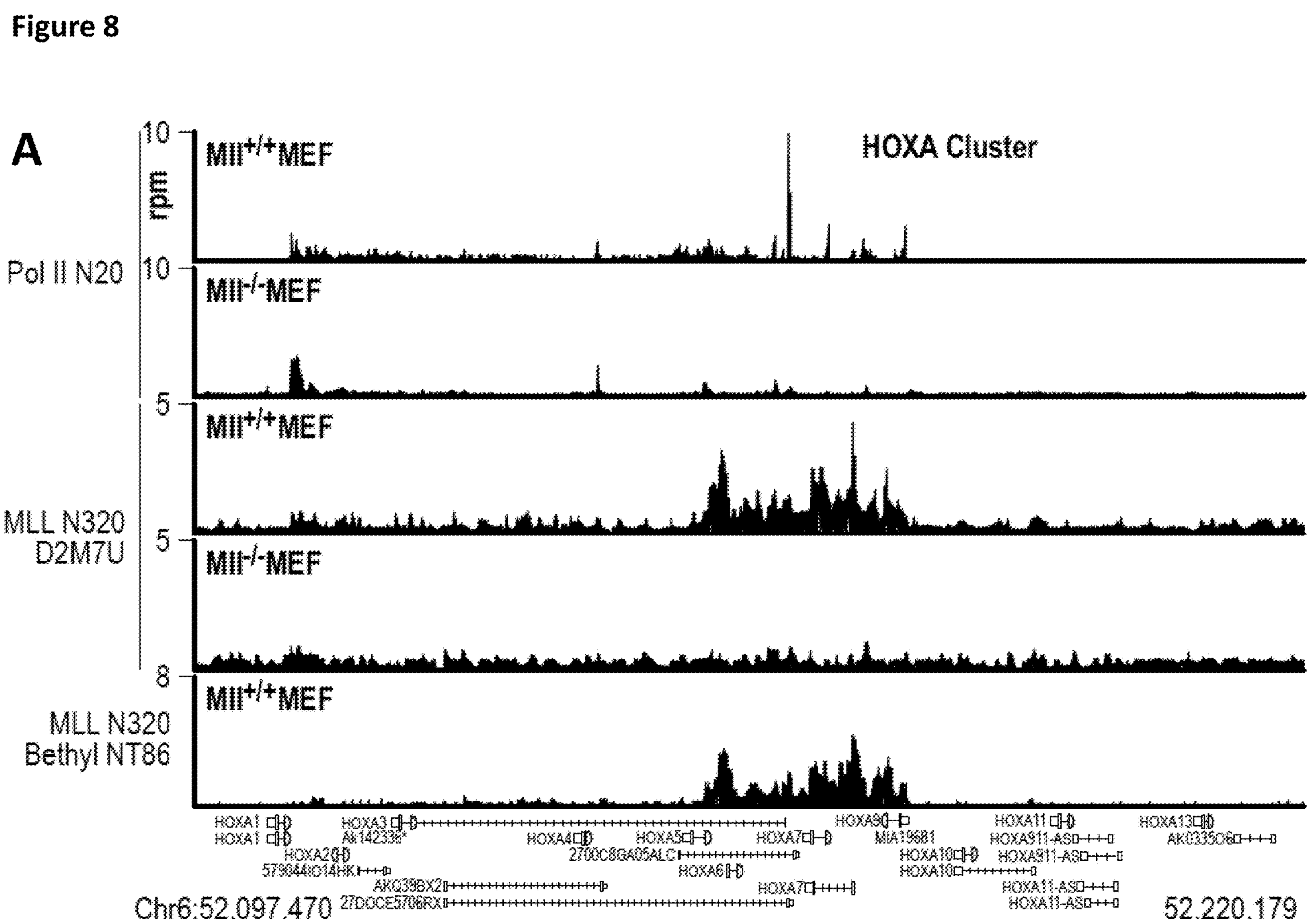
Figure 8:
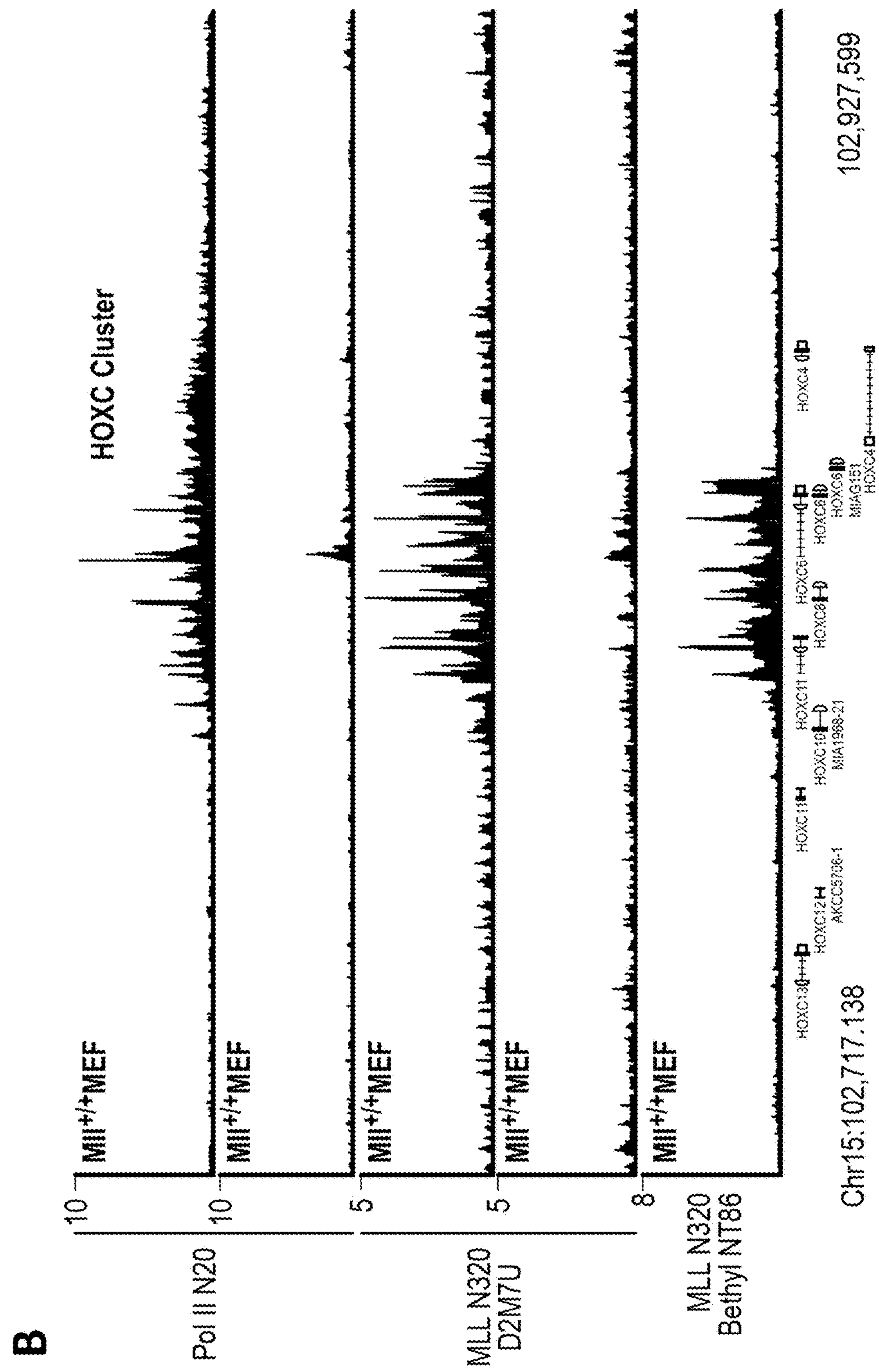
Figure 8:
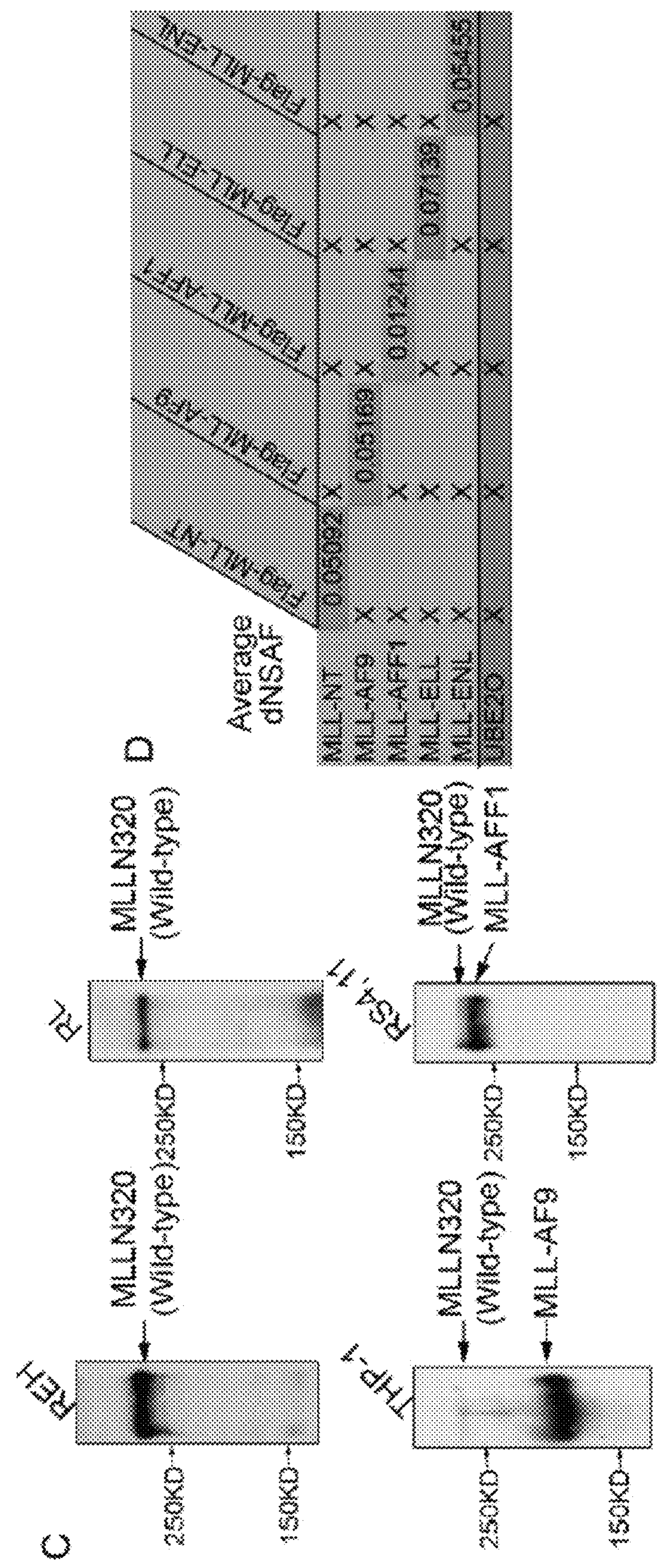
Figure 8:
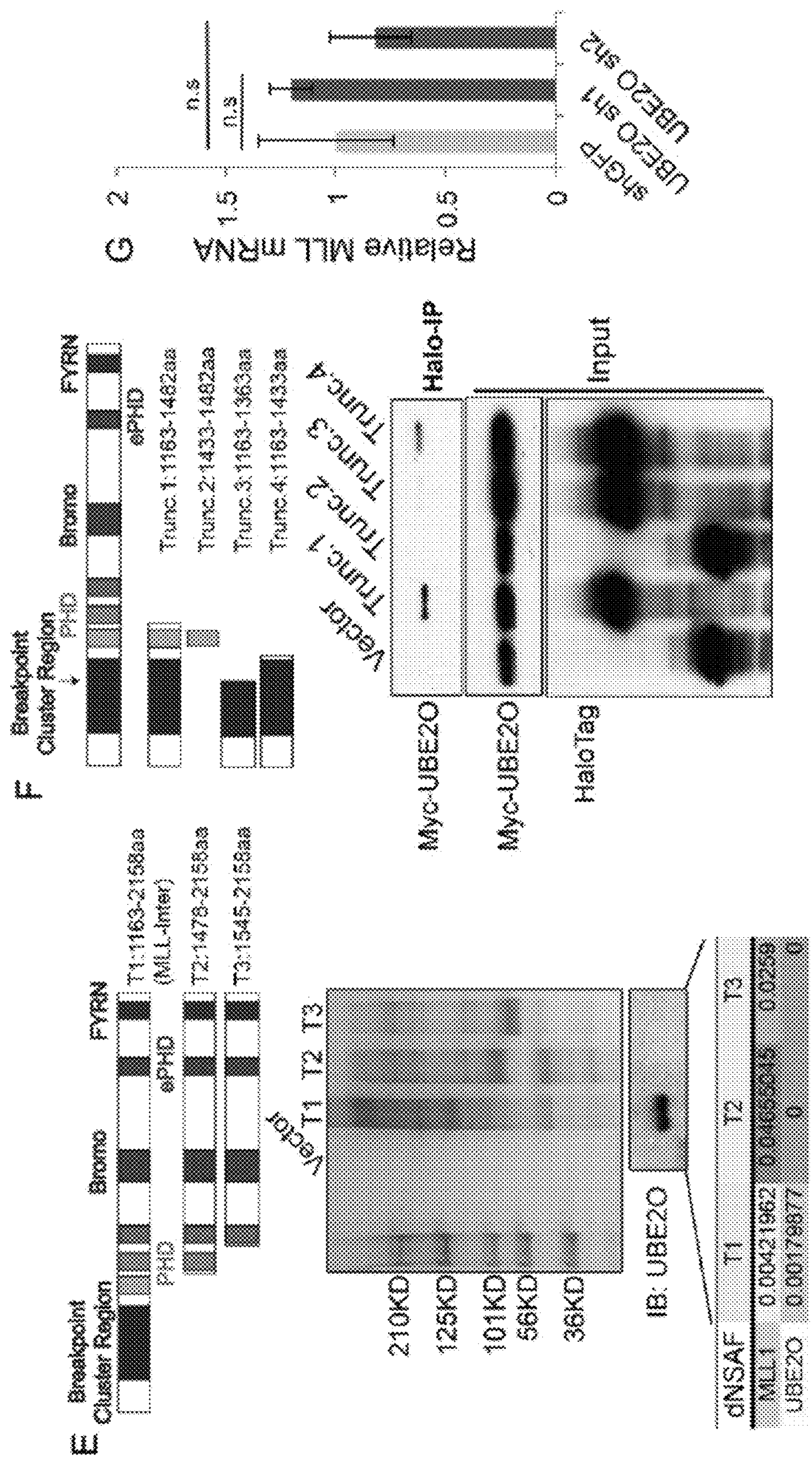

FIG. 8. UBE2O Interacts with an MLL Internal Region and Promotes Wild-type MLL Protein Degradation, Related FIG. 1 (A and B) Verification of the specificity of the MLL D2M7U antibody with ChIP-seq with Mll−/− and Mll+/+ MEF cells. Genome browser views of the Hoxa and Hoxc clusters are shown. ChIP-seq in the Mll wild-type MEFs with a second antibody, Bethyl NT86, is shown. ChIP-seq with Pol II N20 antibody in these MEF cells are also shown at these MLL target genes. (C) Low abundance of wild-type MLL protein in MLL-translocated leukemia cells. MLL-rearranged leukemia cell lines RS4; 11 and THP1 have relatively low levels of wild-type MLL protein compared to the MLL chimera proteins. Immunoblotting with the MLL D2M7U antibody was performed with various total leukemia cell lysates. REH and RL are leukemia cell lines that do not have an MLL translocation and serve as controls. (D) UBE2O does not interact with the MLL N-terminal region shared with the MLL chimeras or with some of the most common MLL chimeras. Flag-MLL-NT, Flag-MLL-AF9, Flag-MLL-AFF1, Flag-MLL-ELL and Flag-MLL-ENL were purified with Anti-Flag M2 beads and subjected to MudPIT analysis (Lin et al., 2010). Distributed normalized spectral abundance factors (dNSAF) are shown. X indicates protein not found. (E) Mapping of MLL-UBE2O interaction domains identifies a region spanning the MLL breakpoint cluster and the first PHD finger as being required for the MLLUBE2O interaction. The MLL-internal region (MLL-Inter), comprising the breakpoint cluster region through the FYRN domain (T1), was further truncated to remove additional PHD fingers (T2 and T3). Halo constructs were transfected in HEK293 cells and purified for MudPIT analysis. (F) MLL-Inter (T1) was further truncated and Halo-MLL truncations were transiently co-transfected with Myc-tagged UBE2O for immunoprecipitation and western blotting with the Myc-tag antibody. (G) Knockdown of UBE2O has no significant effect on MLL mRNA expression. Data are represented as Mean±SD (n=3). n.s, no significant difference with the One-Way AVONA test.

Figure 9:
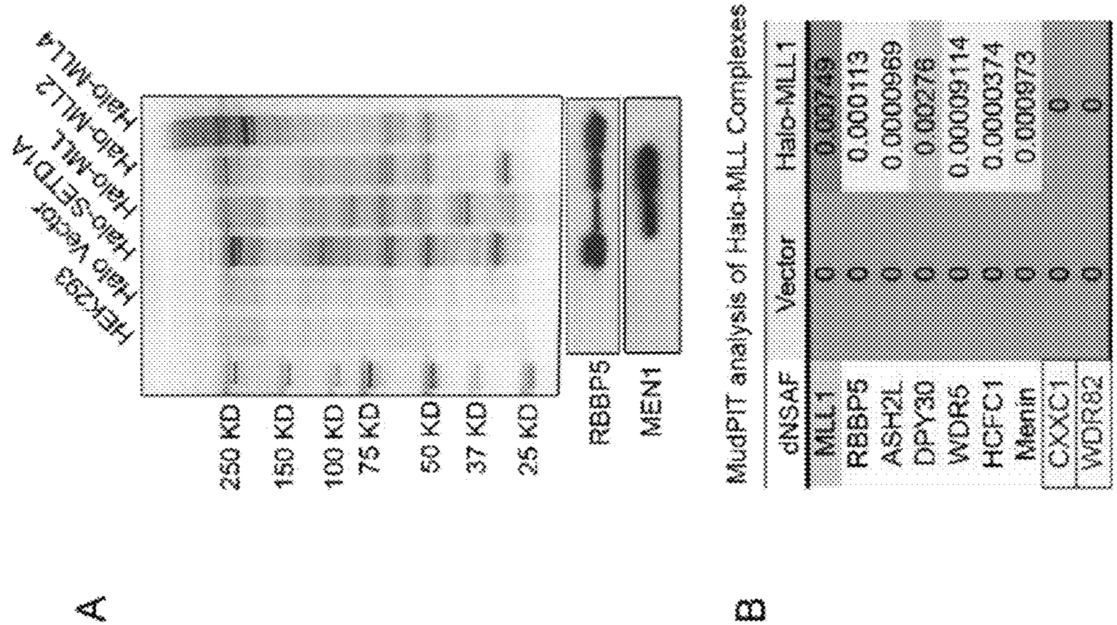
Figure 9:
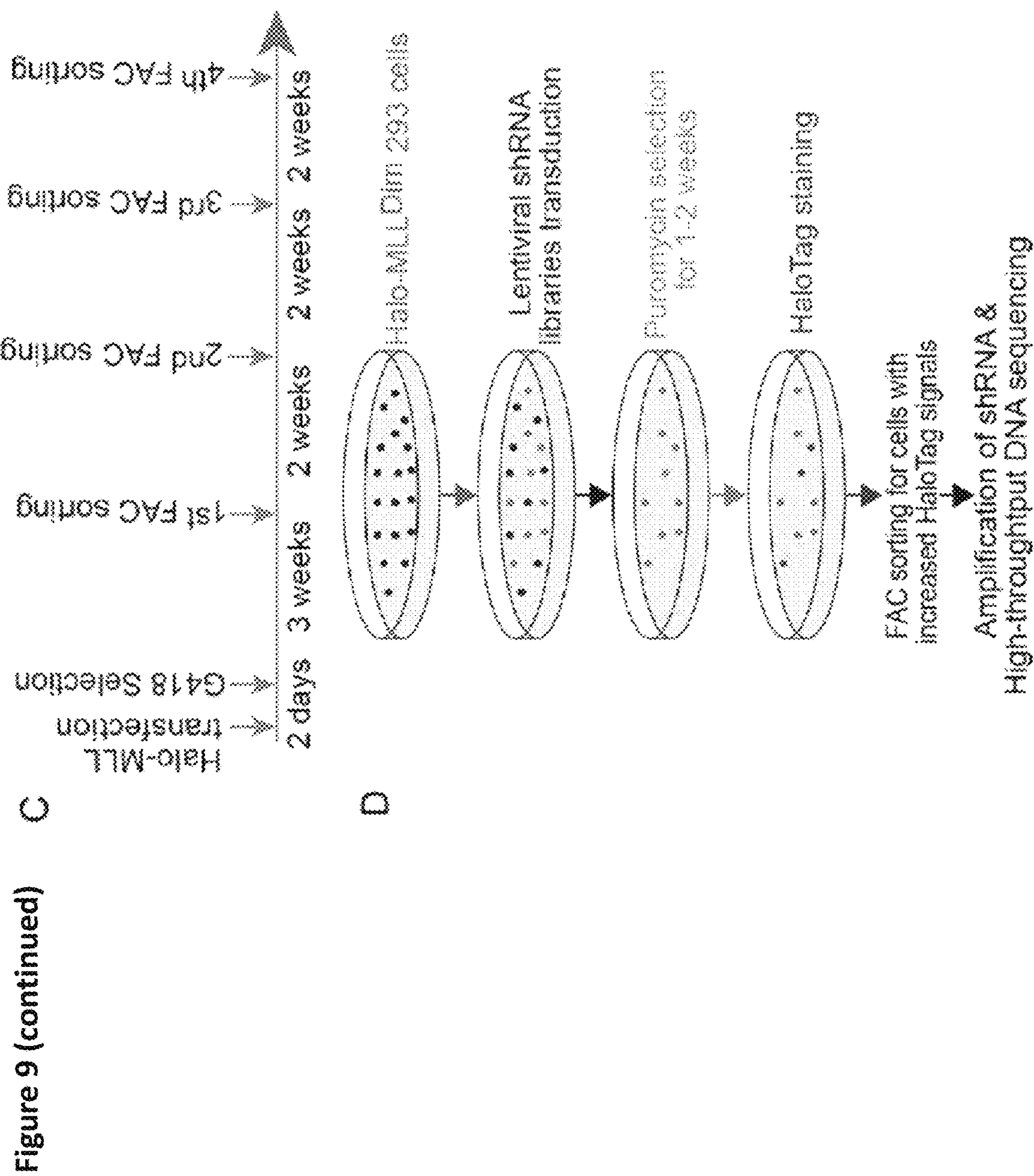
Figure 9:
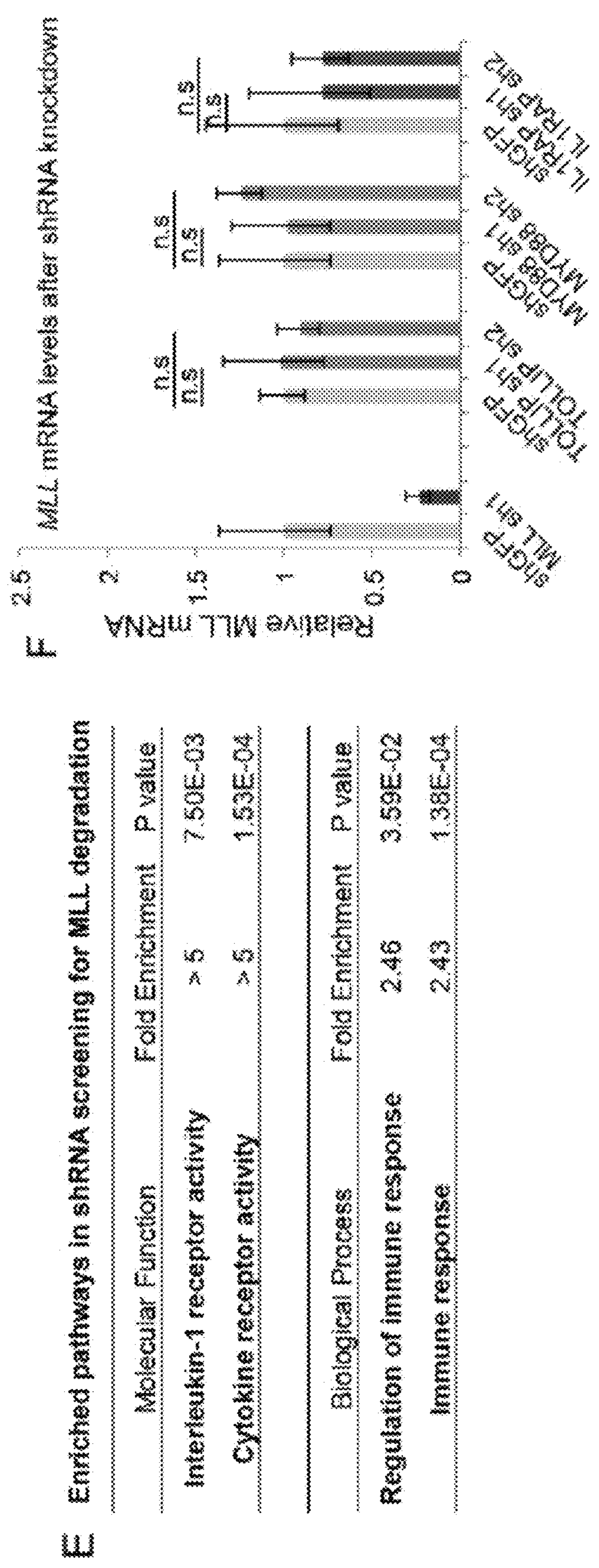

FIG. 9. Genome-wide shRNA Screen Identifies the IL-1 Pathway in Promoting MLL Degradation through an MLL-UBE2O Interaction, Related to (A and B) Halo-MLL can fully reconstitute MLL/COMPASS in HEK293 cells. Biochemical purification of different COMPASS family members with HaloLink resin from transiently transfected HEK293 cells. Halo-purified SETD1A, MLL1, MLL2 (KMT2B) and MLLA (KMT2D) were subjected to SDS-PAGE, silver staining and western blotting. Non-transfected cells (HEK293) and vector only (Halo Vector) transfected cells were used as negative controls. Antibodies recognizing the common COMPASS subunit RBBP5 were used to demonstrate that core COMPASS subunits were present in all COMPASS purifications. In contrast, Menin was only found in the MLL1 and MLL2 purifications. The composition of MLL/COMPASS is also confirmed by MudPIT analysis (B). (C) Flow chart for the generation of Halo-tagged MLLDim cells. After transient transfection of HEK293 cells with Halo-MLL plasmid, cells were selected with G418 for 3 weeks before staining with HaloTag R110 ligand for FACS sorting for low expressing (Halo-MLL-Dim). (D) Workflow for pooled lentiviral shRNA screening. Halo-MLLDim cells were infected with lentiviral shRNA libraries or shGFP and selected for 1-2 weeks with puromycin. After HaloTag R110 staining, flow cytometry sorting was performed to obtain cells with increased Halo-MLL expression. shRNAs from the sorted cells were amplified for high-throughput sequencing. (E) Pathway analysis of the enriched 303 genes from the shRNA library screen identifies the interleukin 1 (IL-1) and cytokine receptor activity as significantly enriched molecular function terms. Immune response and regulation are also enriched in biological process terms. Pathway analysis was performed with PANTHER and the fold enrichments and p values are shown. (F) Depletion of IL-1 pathway components does not affect MLL mRNA levels as determined by RT-qPCR. Data are represented as Mean±SD (n=3). n.s, no significant difference with the One-Way AVONA test.

Figure 10:
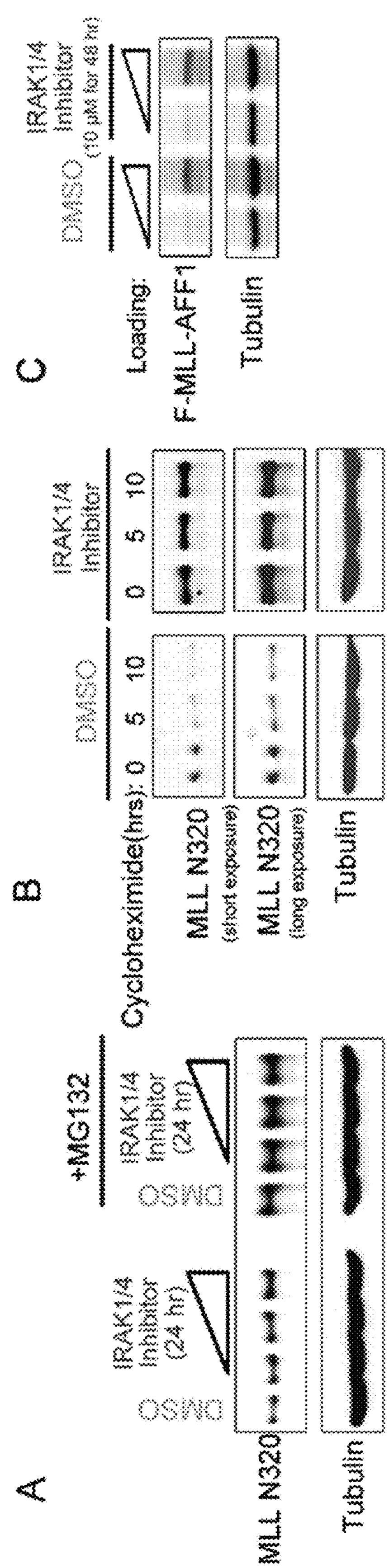
Figure 10:
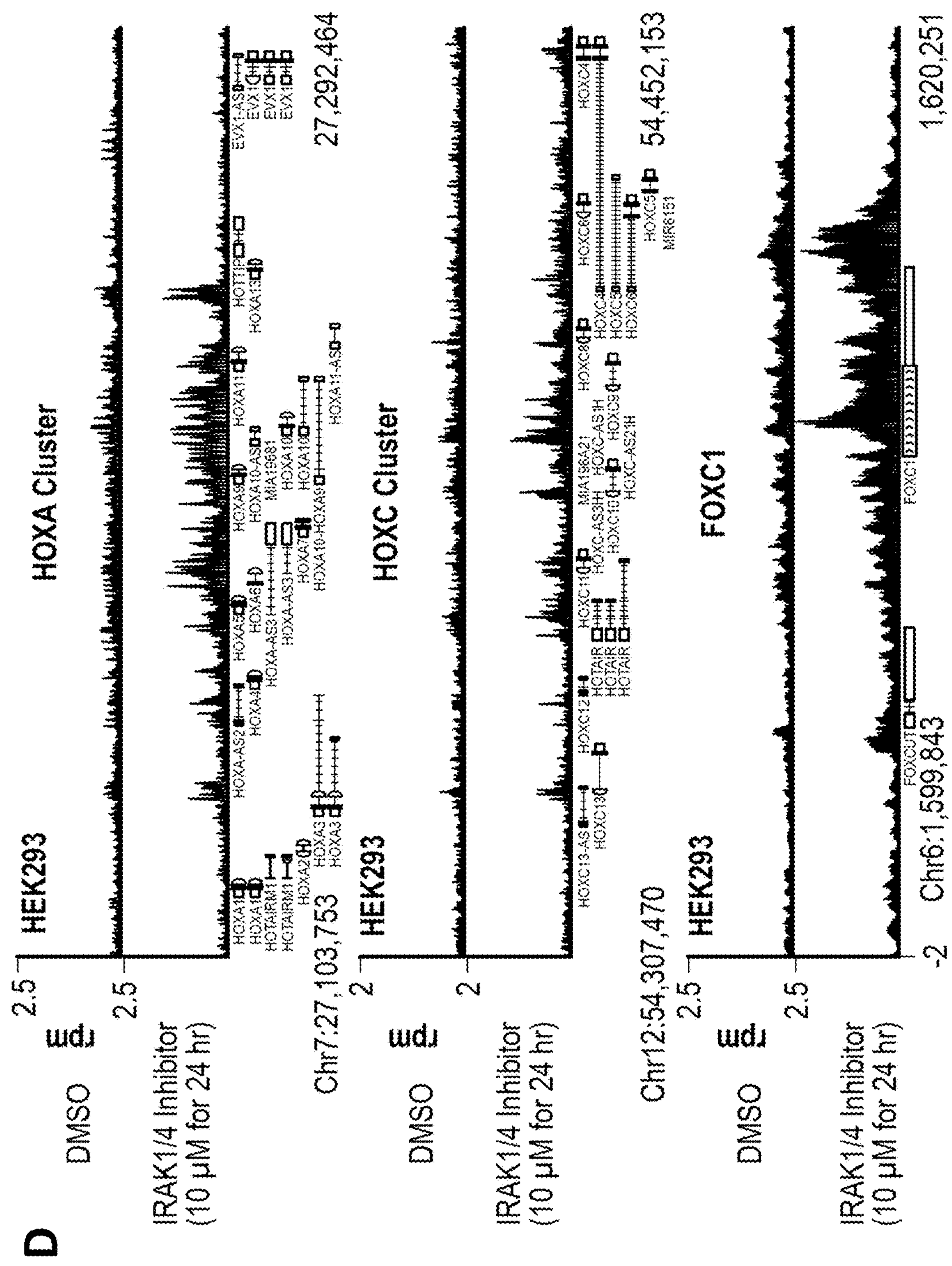
Figure 10:
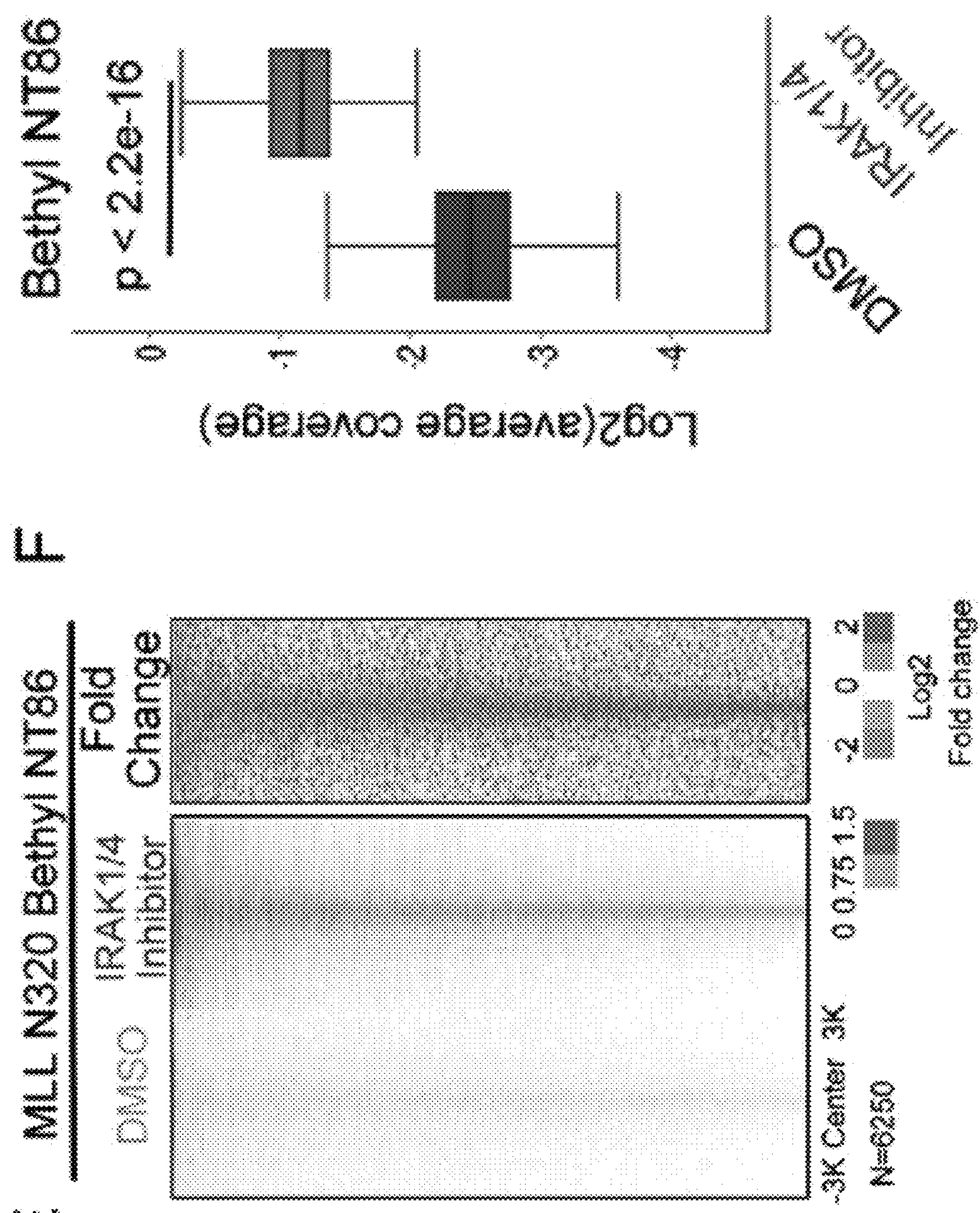

FIG. 10. IRAK Inhibition Stabilizes MLL Protein and Increases Genome-wide MLL Occupancy, Related to FIG. 3 (A) IRAK1/4 inhibitor stabilizes MLL protein from proteasomal degradation in a dose-dependent manner. HEK293 cells were first treated with different concentrations of IRAK1/4 inhibitor for 24 hr followed by treatment with DMSO or the proteasome inhibitor MG132 for 12 hr. (B) IRAK1/4 inhibitor increases the stability of endogenous MLL. After DMSO or IRAK1/4 inhibitor treatment for 24 hr, HEK293 cells were treated with the protein biosynthesis inhibitor cycloheximide for 5 and 10 hr. (C) IRAK1/4 inhibition does not stabilize MLL-AFF1 chimeras. Flag-MLL-AFF1 HEK293 cells were treated with the IRAK1/4 inhibitor at 10 mM for 2 days and subjected to western blotting with anti-FLAG. (D) IRAK1/4 inhibition increases MLL occupancy as revealed by ChIP-seq. Track examples of ChIP-seq with anti-MLL N320 (Bethyl NT86) at HOXA, HOXC, and FOXC1 loci reveal increased MLL occupancy in the presence of the IRAK1/4 inhibitor. (E and F) Heatmap of MLL occupancy in the presence of DMSO or the IRAK1/4 inhibitor. Occupancy in reads per million (rpm)±3 kb around the center of peak is shown (N=6250). Genes are ordered by MLL occupancy in the inhibitor treatment. The log 2 fold change heatmap indicates a general increase in MLL occupancy after IRAK1/4 inhibitor treatment (E). The read counts of all the MLL peaks were plotted and the Wilcoxon signed-rank test was used to calculate the p value (F).

Figure 11:
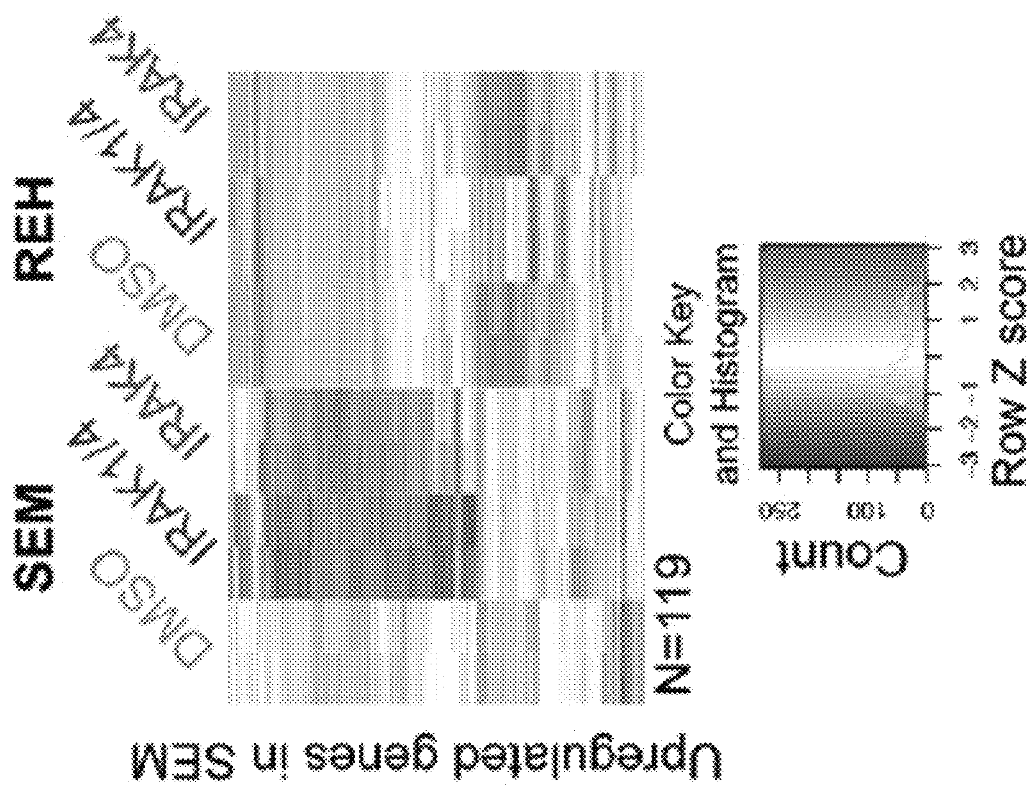
Figure 11:
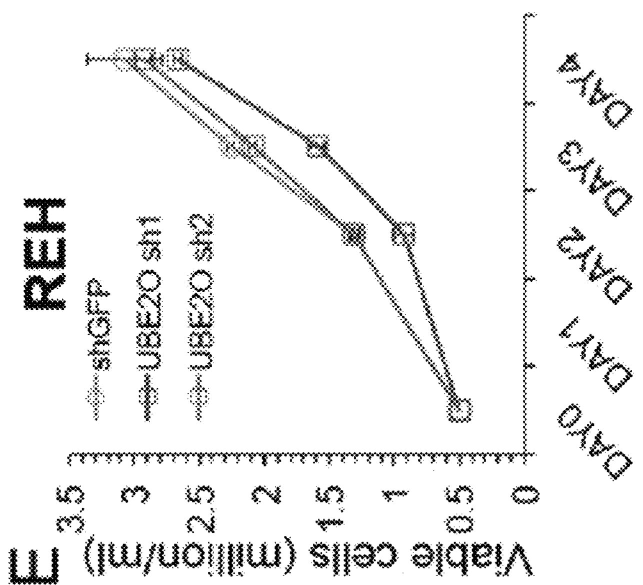
Figure 11:
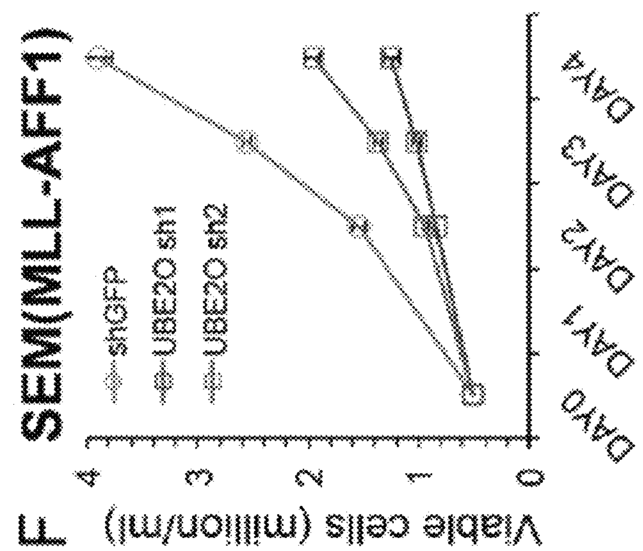
Figure 11:
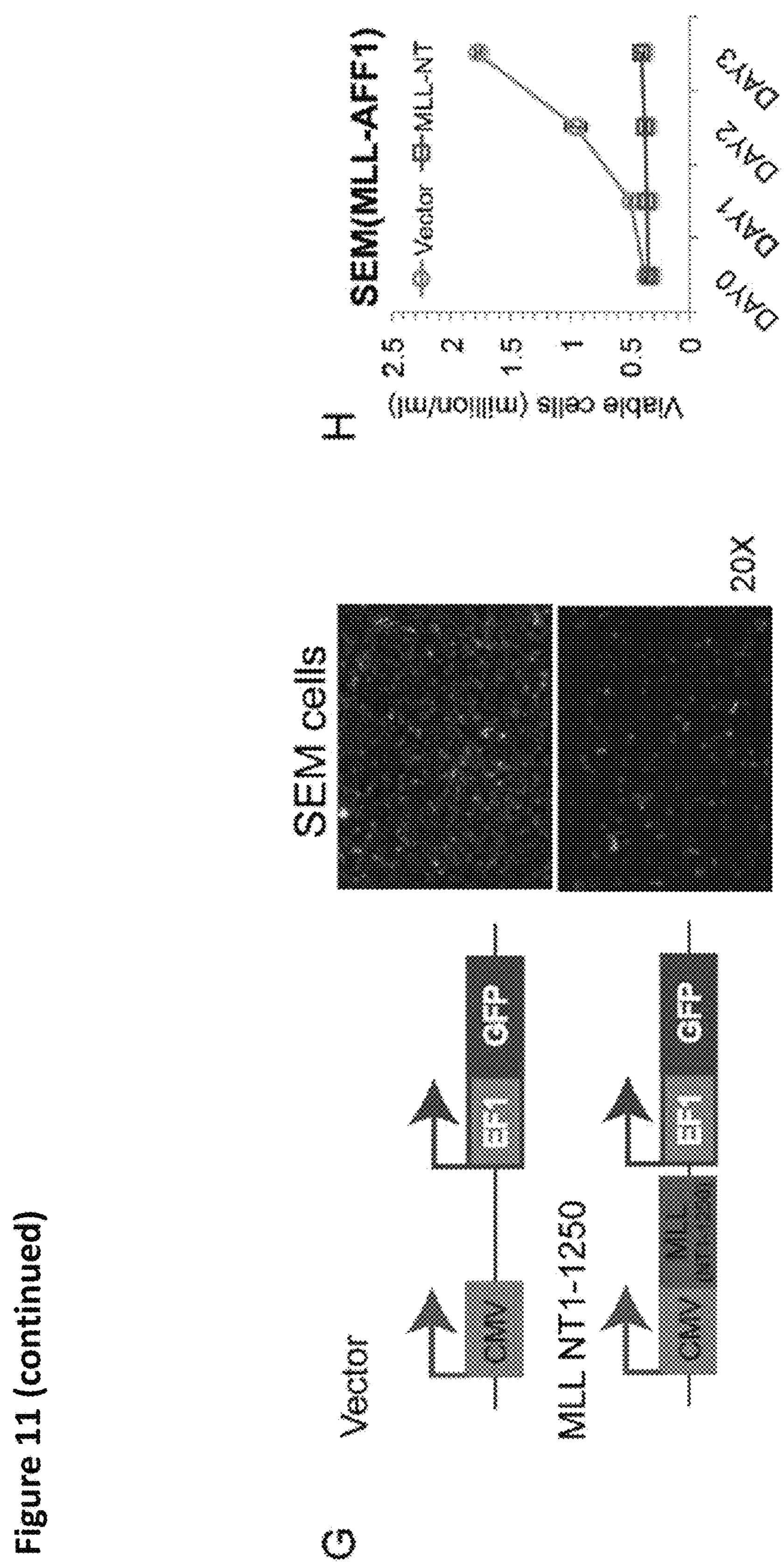

FIG. 11. Stabilization of MLL through IRAK Inhibition or UBE2O Depletion Impedes Cell Proliferation and Deregulates a Gene Regulatory Network in MLL Leukemia, Related to FIG. 4 (A and B) Venn diagram and gene ontology analysis of common deregulated genes in REH and SEM cells after IRAK 1/4 inhibitor treatment. 238 genes were downregulated and 186 genes were upregulated in both REH and SEM cells. (C) Hierarchical clustering of the 119 genes specifically upregulated in SEM cells by both the IRAK1/4 and IRAK4 inhibitor treatments. (D) Gene ontology analysis of SEM-specific deregulated genes by both IRAK inhibitors. The enriched terms are shown with p values and FDR-adjusted q-values. (E and F) Depletion of UBE2O preferentially inhibits the MLL leukemic SEM cell growth compared to non-MLL REH cells. REH and SEM cells were infected with UBE2O shRNA virus and selected with puromycin for 4 days. Viable cells were seeded and monitored for 4 more days. Data represent the Mean±SD (n=3). p<0.005, One-Way ANOVA. (G and H) Ectopic expression of an MLL-N-terminal region (1-1250aa) blocks MLL leukemic SEM cell proliferation. SEM cells were infected with lentivirus expressing MLL-NT (1-1250 aa). 2 days after lentivirus infection, the SEM cells were selected with puromycin for 4 days and monitored for GFP expression (G). The viable cells were seeded at day 0, and counted by trypan blue exclusion staining with a cell viability analyzer (H). Data are represented as Mean±SD (n=3). p<0.005, One-Way ANOVA.

Figure 12:
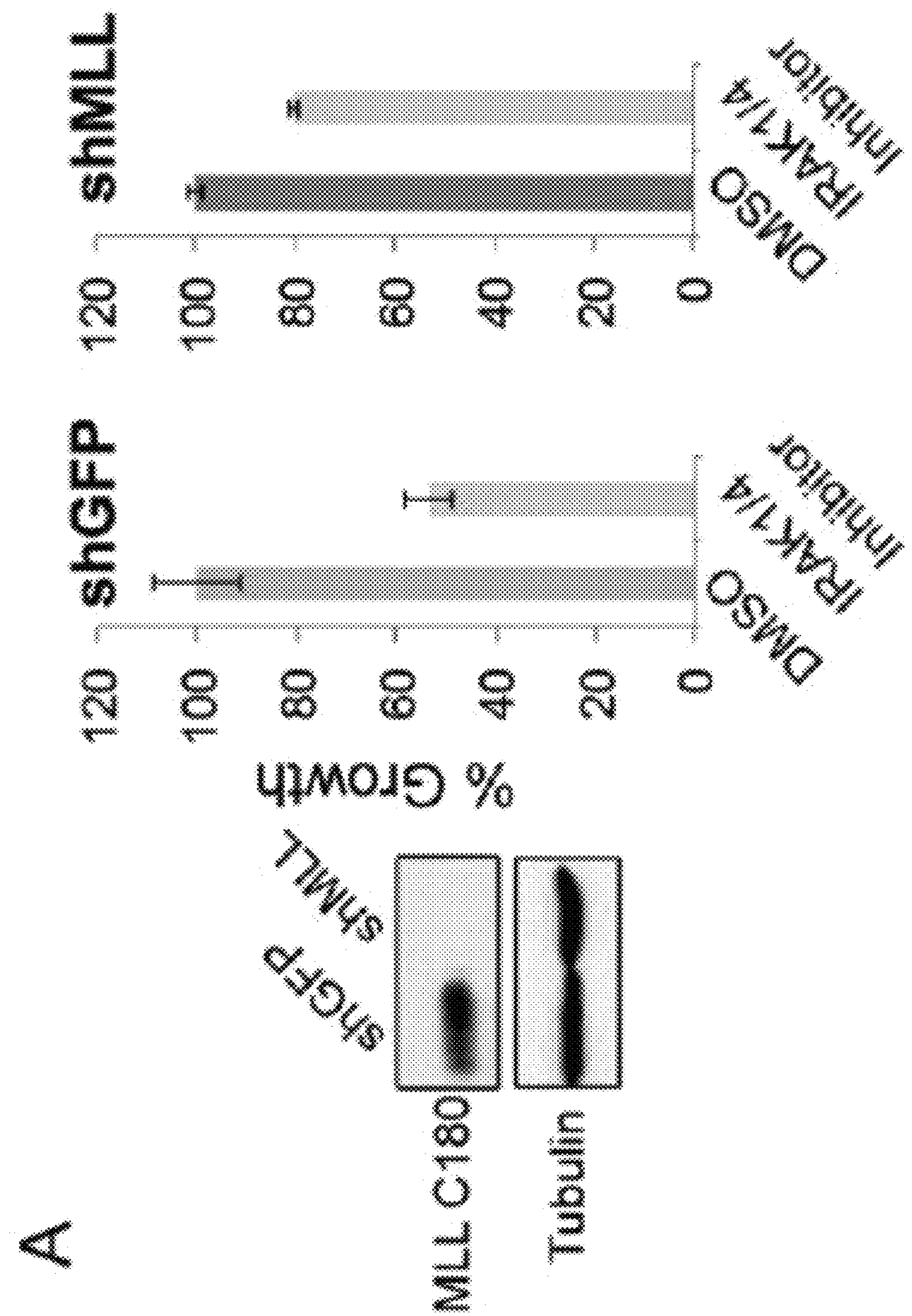
Figure 12:
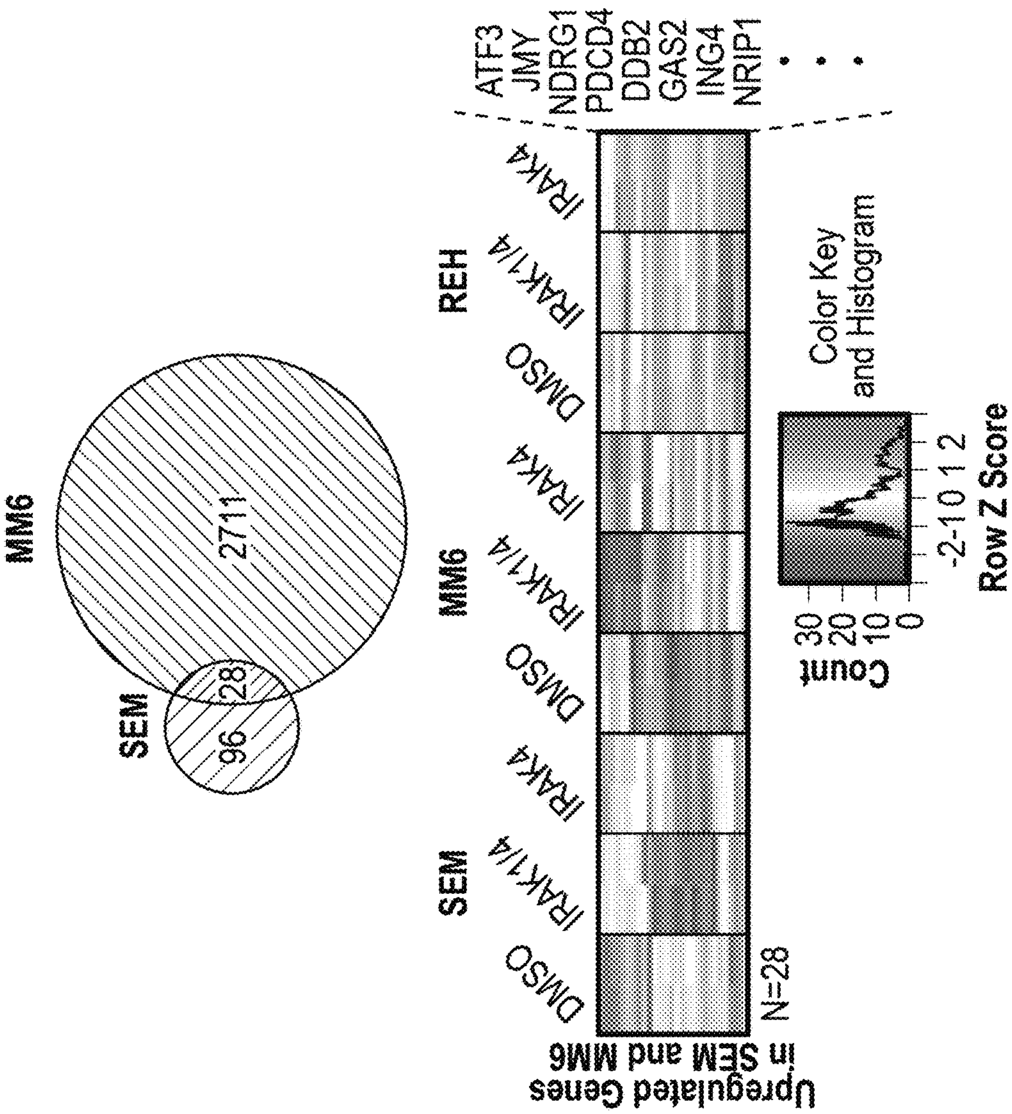
Figure 12:
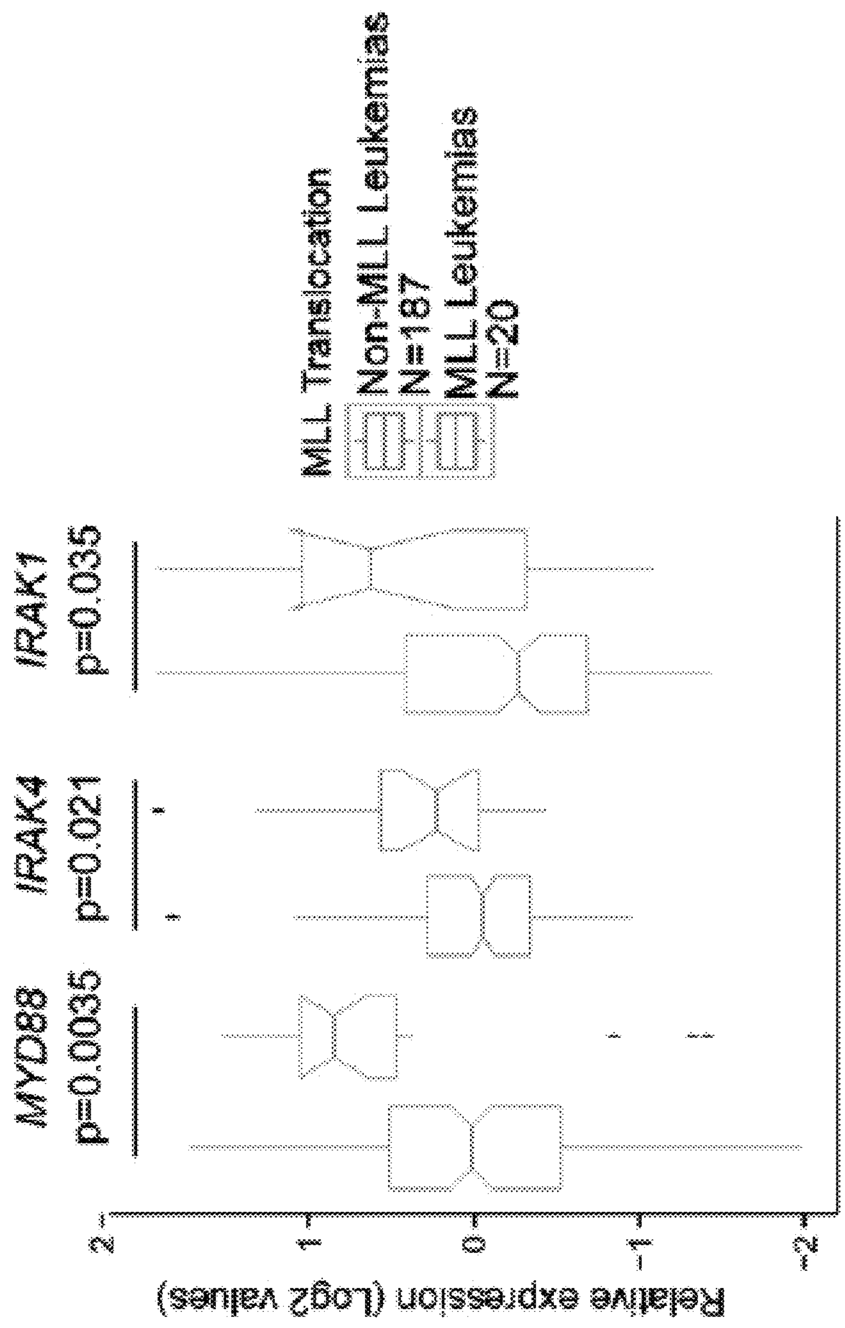
Figure 12:
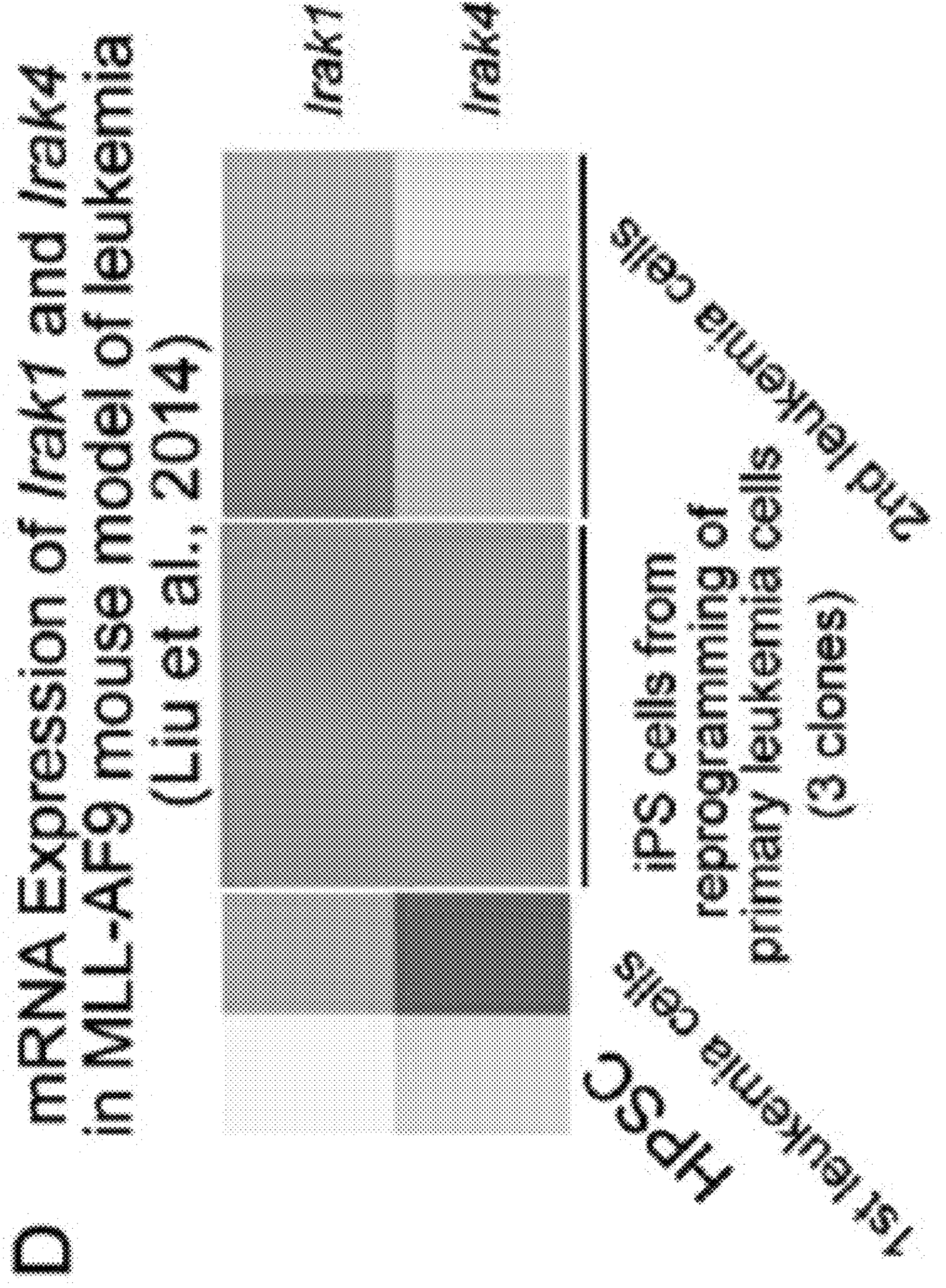

FIG. 12. Determinants of the Increased Sensitivity of MLL Leukemia Cells to IRAK Inhibition, Related to FIG. 5 (A) Depletion of wild-type MLL reduces the sensitivity of MM6 cells to the IRAK1/4 inhibitor. MM6 cells were depleted with a shRNA targeting the C terminus of MLL for 3 days. Viable cells were seeded at 0.2 million/ml and cultured for 4 days in the presence or absence of 5 mMI-RAK1/4 inhibitor before cell counting. Data represent the Mean±SD (n=3). (B) Hierarchical clustering of the 28 genes that are upregulated by the IRAK1/4 and IRAK4 inhibitor treatments in SEM and MM6 cells. (C) MYD88, IRAK1 and IRAK4 have higher expression in MLL ALL patient cells compared to other ALL leukemia patient cells (TARGET ALL microarray data from Cancer UCSC genome database. Project: COG, POG 9906). P values were calculated with the Wilcoxon signed-rank test. (D) Irak1 and Irak4 expression profiles in iPS cells, HPSC and MLL-AF9 transformed 1st and 2nd leukemia cells from a previously published study (Liu et al., 2014).

Figure 13:
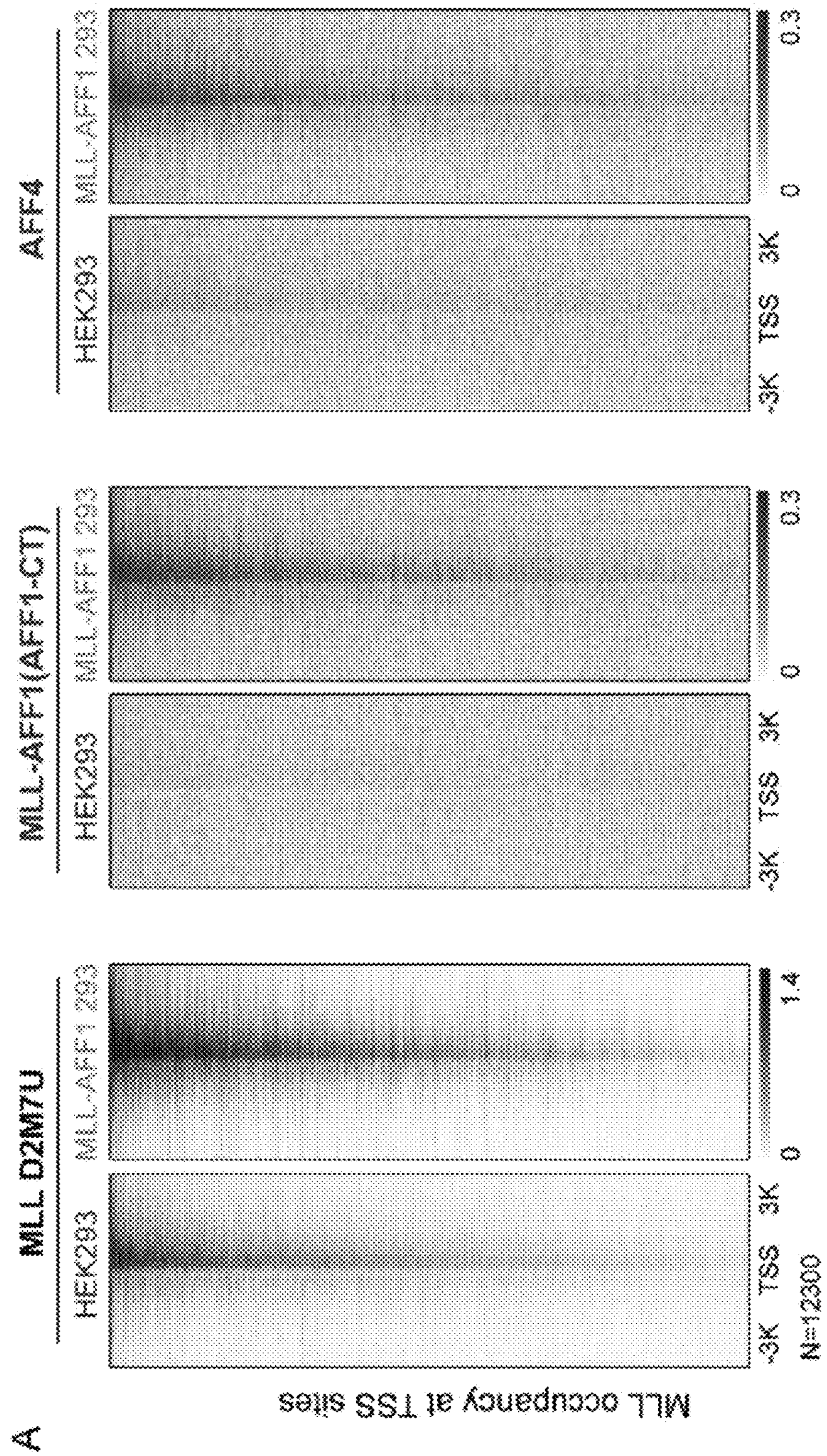
Figure 13:
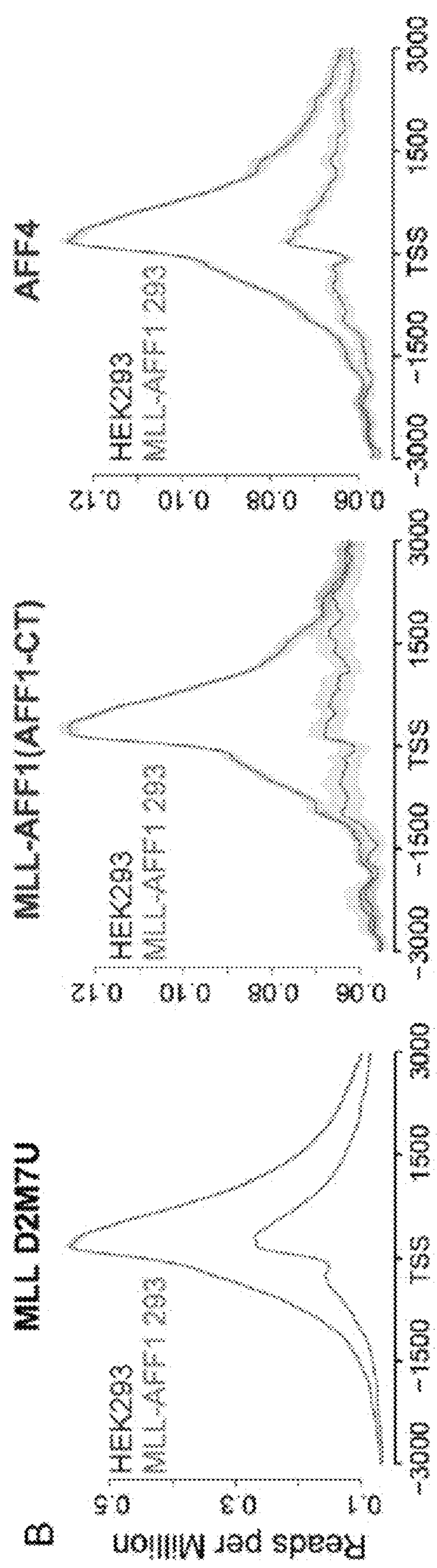
Figure 13:
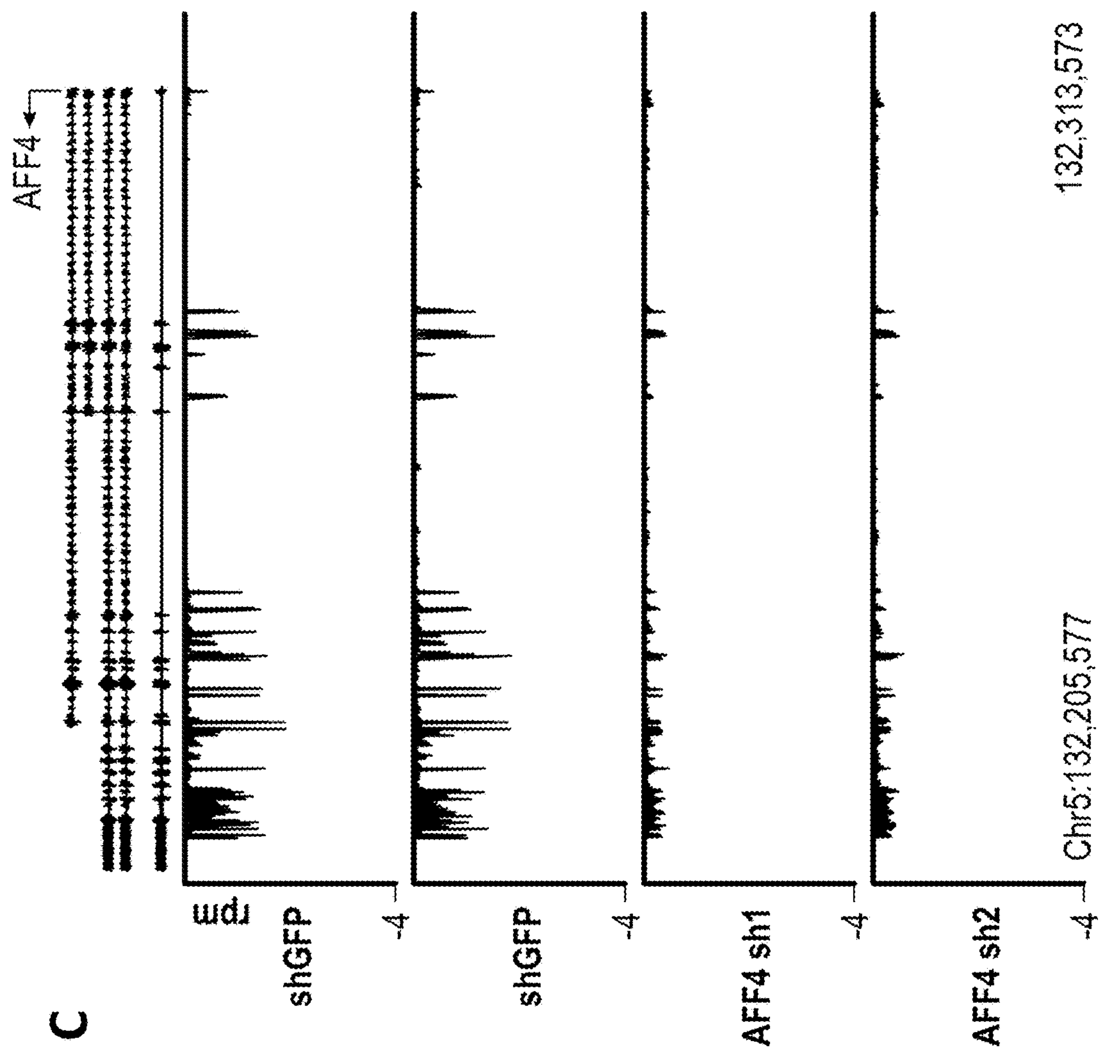
Figure 13:
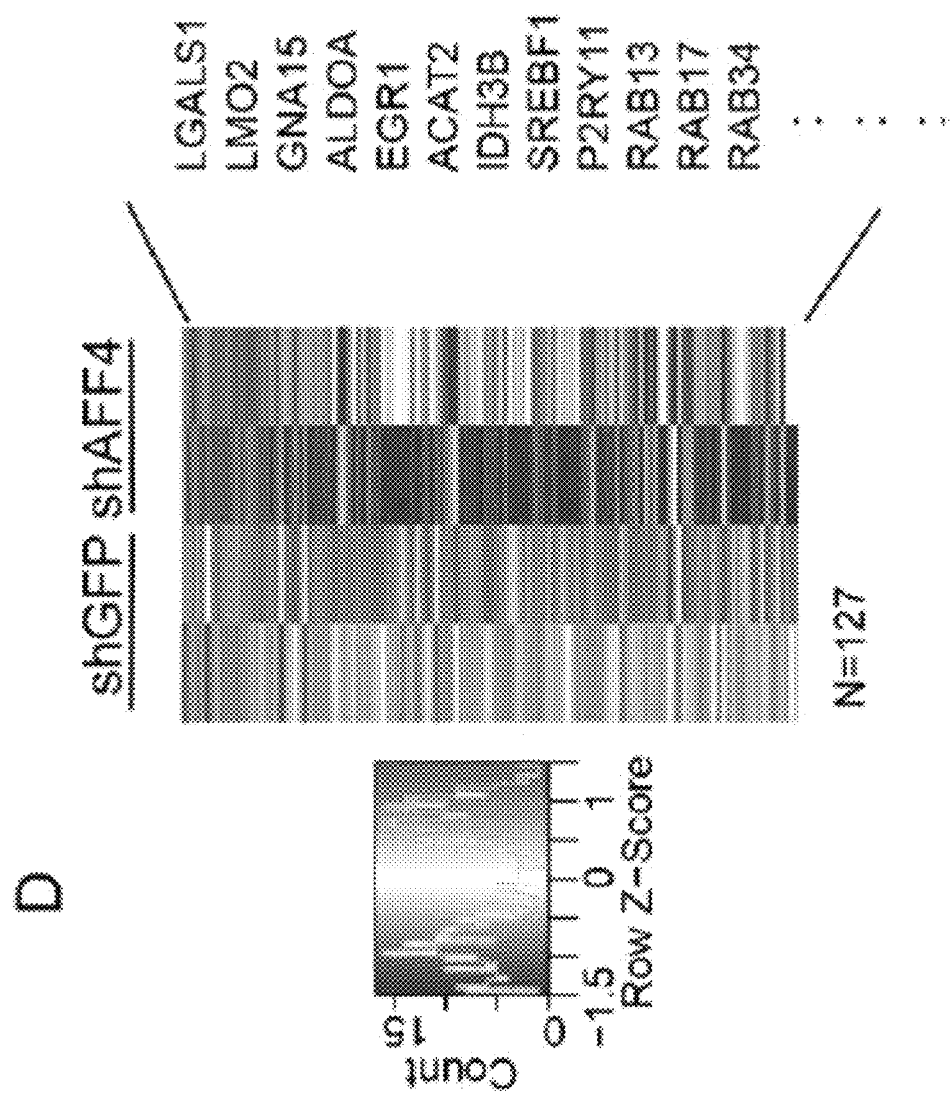

FIG. 13. IRAK Inhibition Displaces MLL Chimera and SEC Occupancy at a Subset of MLL Chimera and SEC Target Genes, Related to FIG. 6. (A) MLL-AFF1 chimera shares the same chromatin binding sites with wild-type MLL and recruits SEC. Heatmap analysis of MLL N320, AFF1-CT and AFF4 occupancy in HEK293 and Flag-MLL-AFF1 HEK293 cells. In MLL-AFF1 HEK293 cells, the D2M7U antibody could detect both wild-type MLL and MLL-AFF1. Ectopically expressed MLL-AFF1 in HEK293 cells targets the same sites as wild-type MLL as revealed by increased occupancy of both MLL N320 and AFF1-CT. AFF4, a subunit of SEC, is also recruited to these MLL-AFF1 binding sites. All protein coding genes with MLL occupancy in either HEK293 or MLL-AFF1 HEK293 cells are included in the heatmap. Each row represents a gene with MLL occupancy around the TSS site (N=12300). (B) Metagene plot of MLL, AFF1-CT and AFF4 occupancies in HEK293 and Flag-MLL-AFF1 HEK293 cells. (C) Genome browser RNA-seq tracks at the AFF4 gene with and without AFF4 knockdown in SEM cells. (D) Decreased expression of 127 genes in SEM cells by both IRAK inhibition and AFF4 knockdown. Some examples of downregulated genes are indicated on the right.

Figure 14:
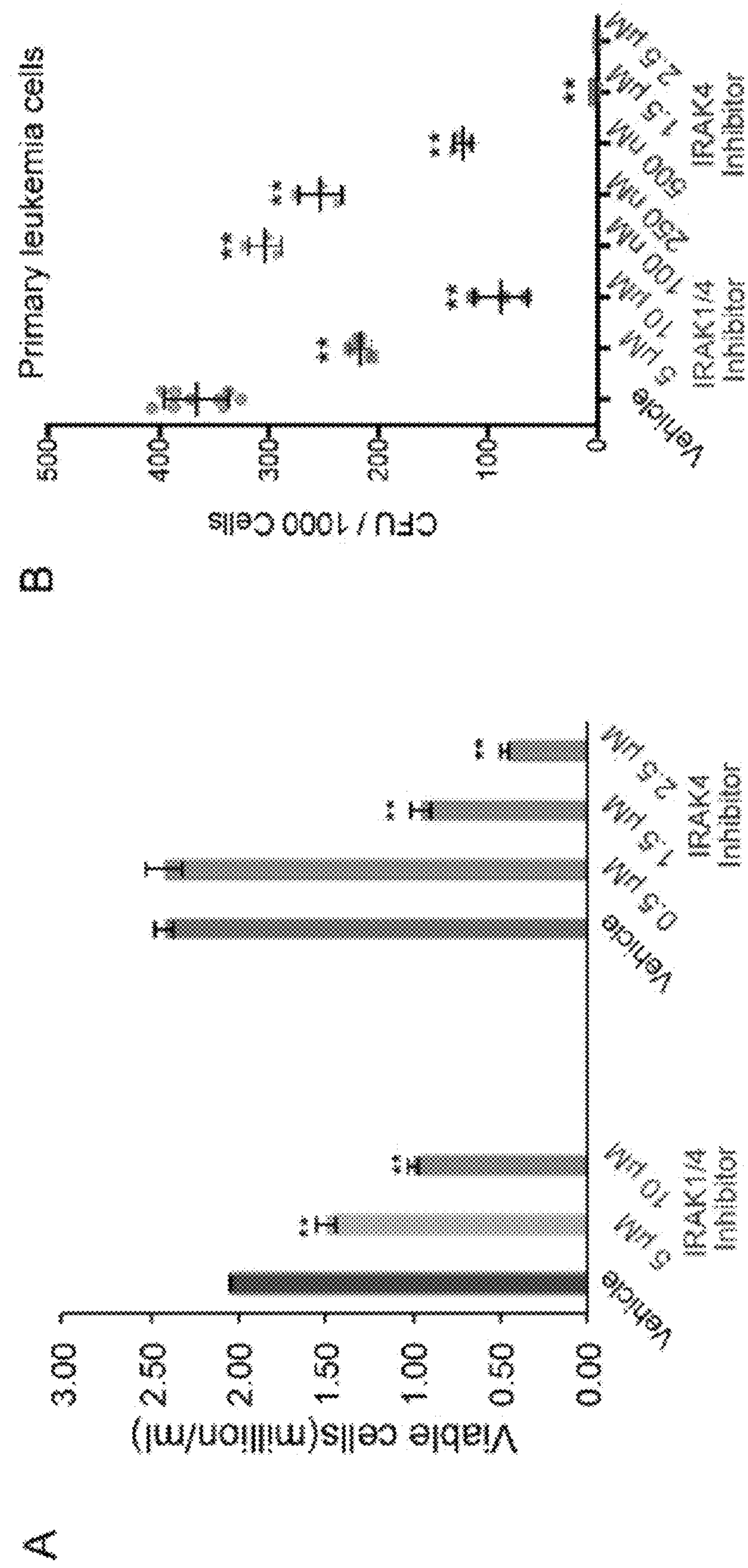
Figure 14:
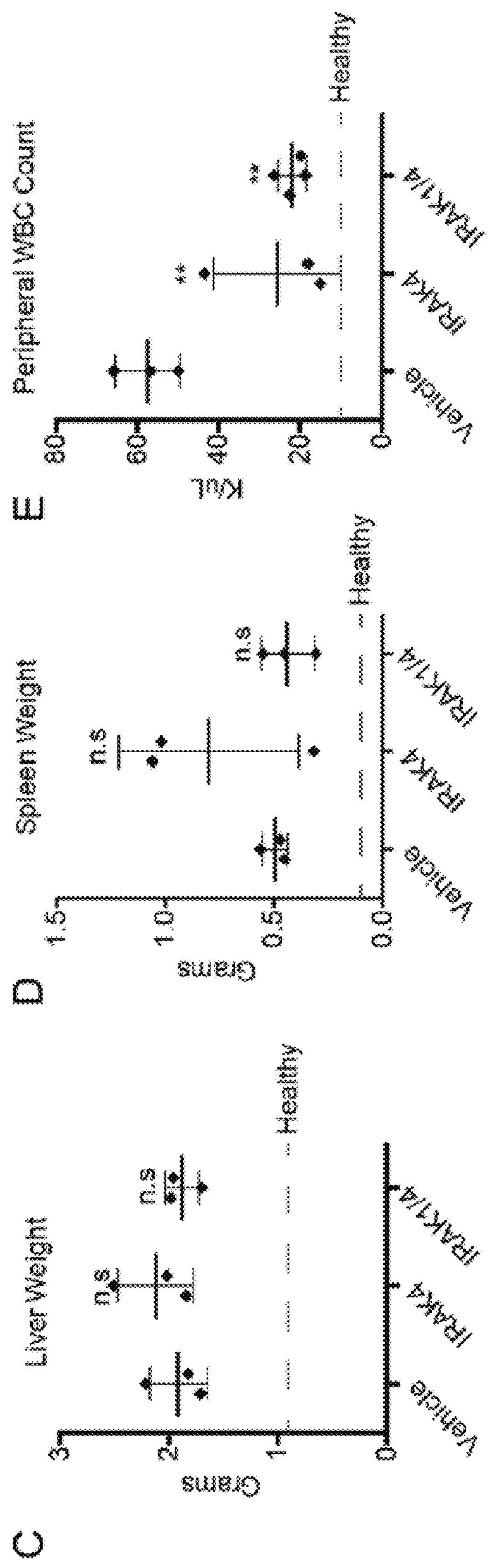

FIG. 14. IRAK Inhibition Substantially Delays Disease Progression and Improves Survival of MLL-AF9 Leukemia Mice, Related to FIG. 7 (A) IRAK inhibitors suppress growth of primary murine MLL-AF9 cells. Different dosages of IRAK inhibitors were added to the isolated primary MLL-AF9 leukemia cells in the presence of IL3, IL6 and SCF. Two days later, the viable leukemia cells were monitored by trypan blue exclusion. p<0.005 (One-Way ANOVA). (B) IRAK inhibitors decrease the colony formation ability of primary murine MLL-AF9 leukemia cells in vitro. 1000 primary MLL-AF9 leukemia cells were seeded and treated with DMSO or IRAK inhibitors at various dosages for the methylcellulose colony formation assay. p<0.005 (One-Way ANOVA). (C and D) Spleen and liver weights of vehicle and IRAK inhibitor-treated groups at sacrifice. (E) White blood cells counts of vehicle and IRAK inhibitor-treated groups at the endpoint. **p<0.005 (One-Way ANOVA).

Figure 15:
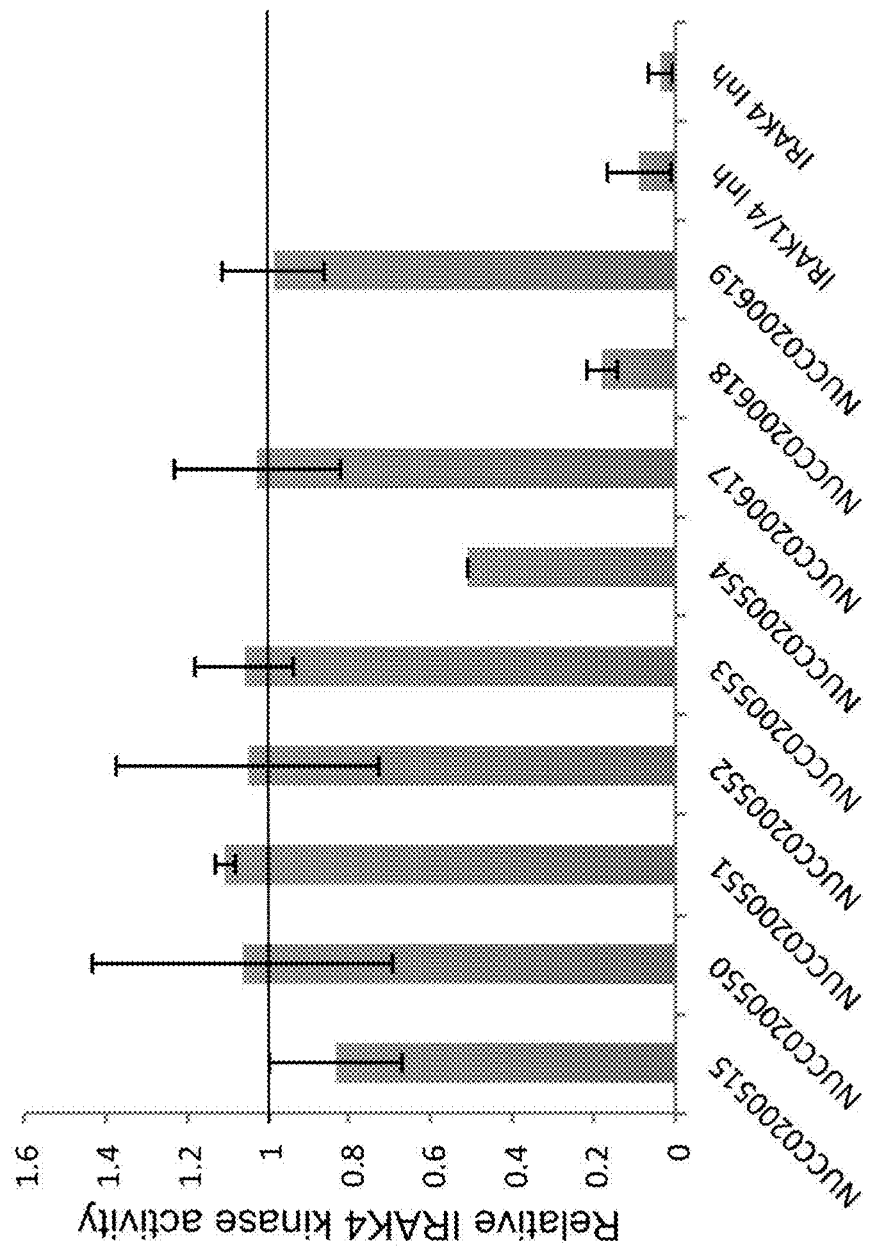

FIG. 15. Inhibition of IRAK4 kinase activity by NU's IRAK4 kinase inhibitors. 10 ng IRAK4, 12.5 uM ATP and 500 ng MBP (substrate) were used in the IRAK4 kinase assay. 100 uM of each inhibitor were used individual in the assay and the reaction product ADP was detected by the ADP-GLO assay. Relative activity to DMSO is shown.

Figure 16:
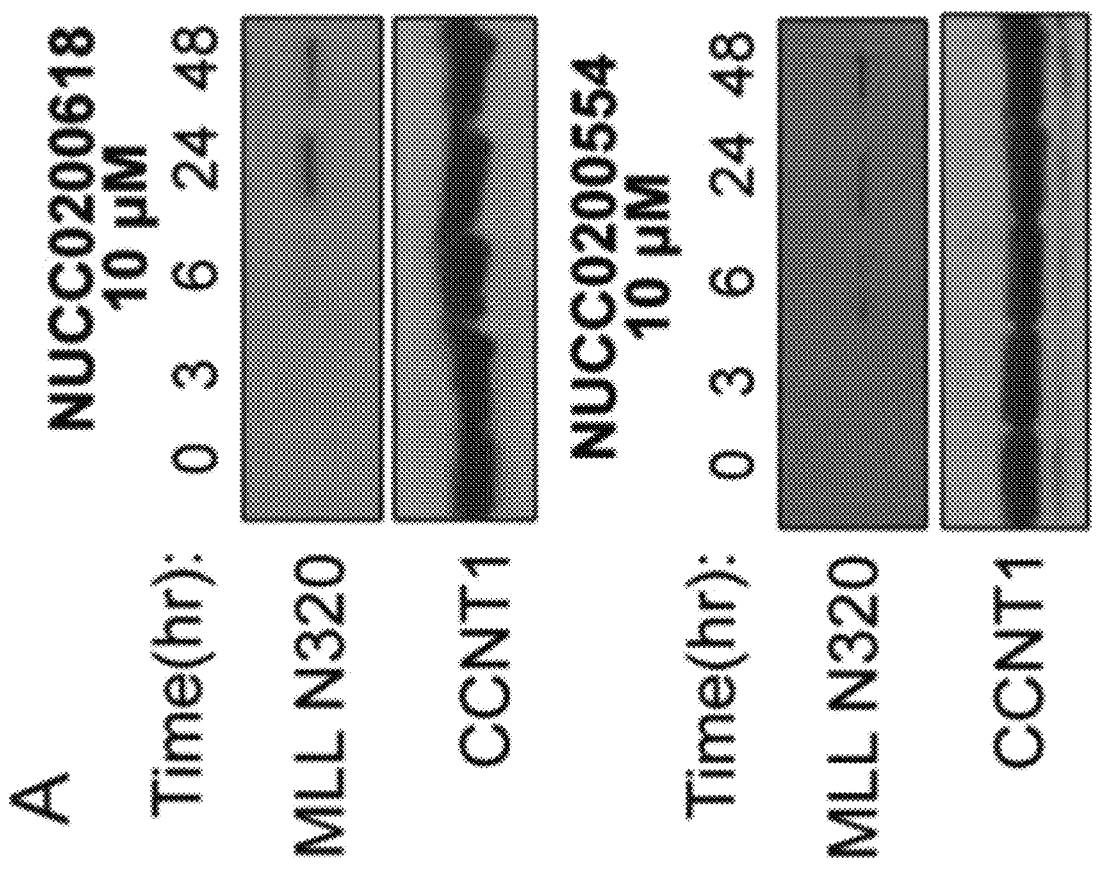
Figure 16:
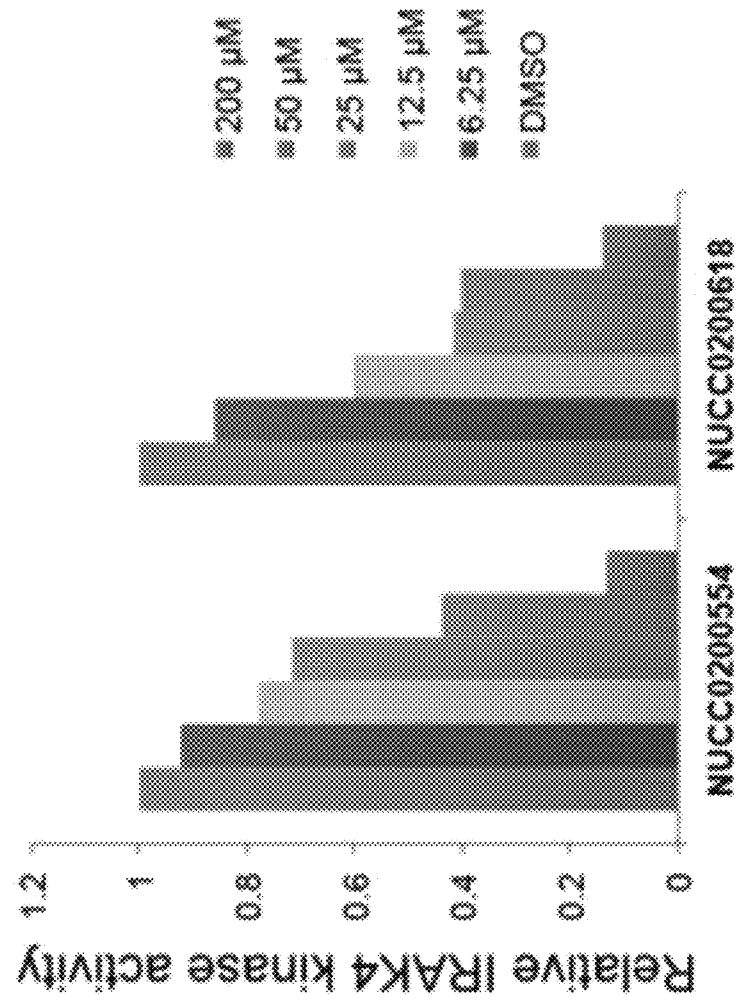
Figure 16:
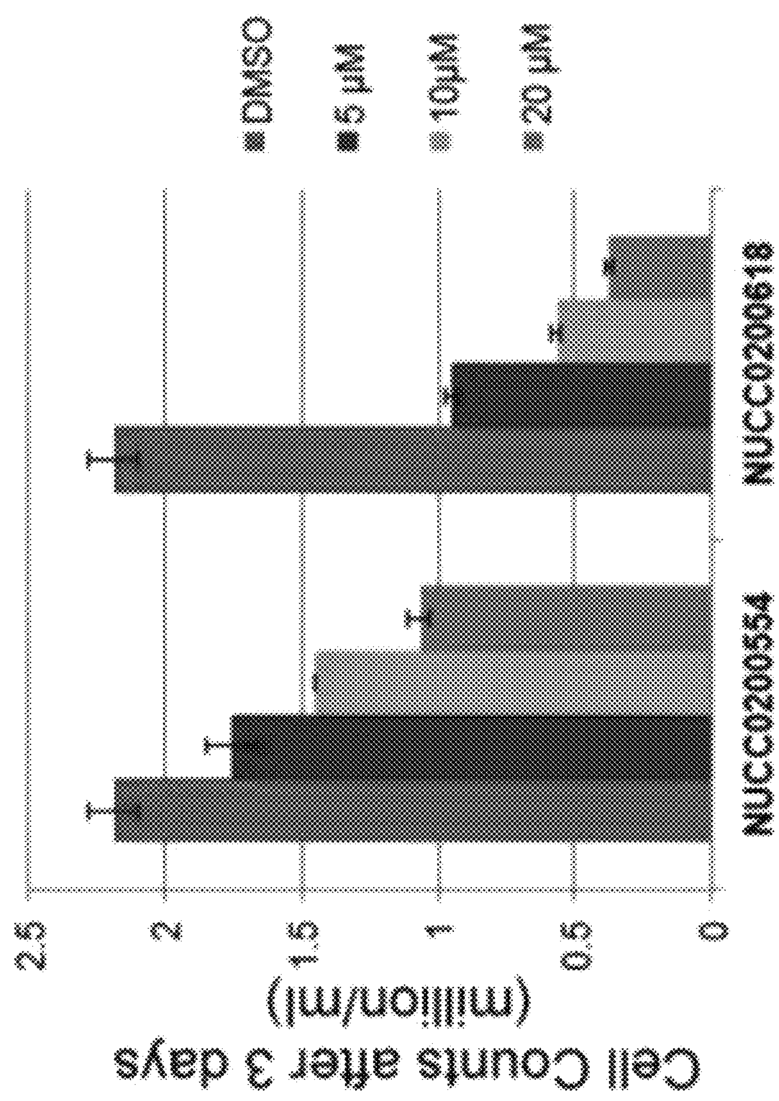

FIG. 16. Development of novel compounds (NUCC0200618 and NUCC0200554) that stabilize the wild-type MLL protein and slow leukemic cell growth through IRAK4 inhibition. A) Western blotting for MLL protein levels in cells treated with the indicated compounds designed and synthesized at Northwestern. Protein stabilization is observed to increase by 6 hours of treatment. B) Luciferase-based IRAK4 kinase assays (Promega) with the indicated doses of the new compounds. C) Cell viability counts after 3 days of treatment with the indicated doses of the new compounds.

Figure 17:
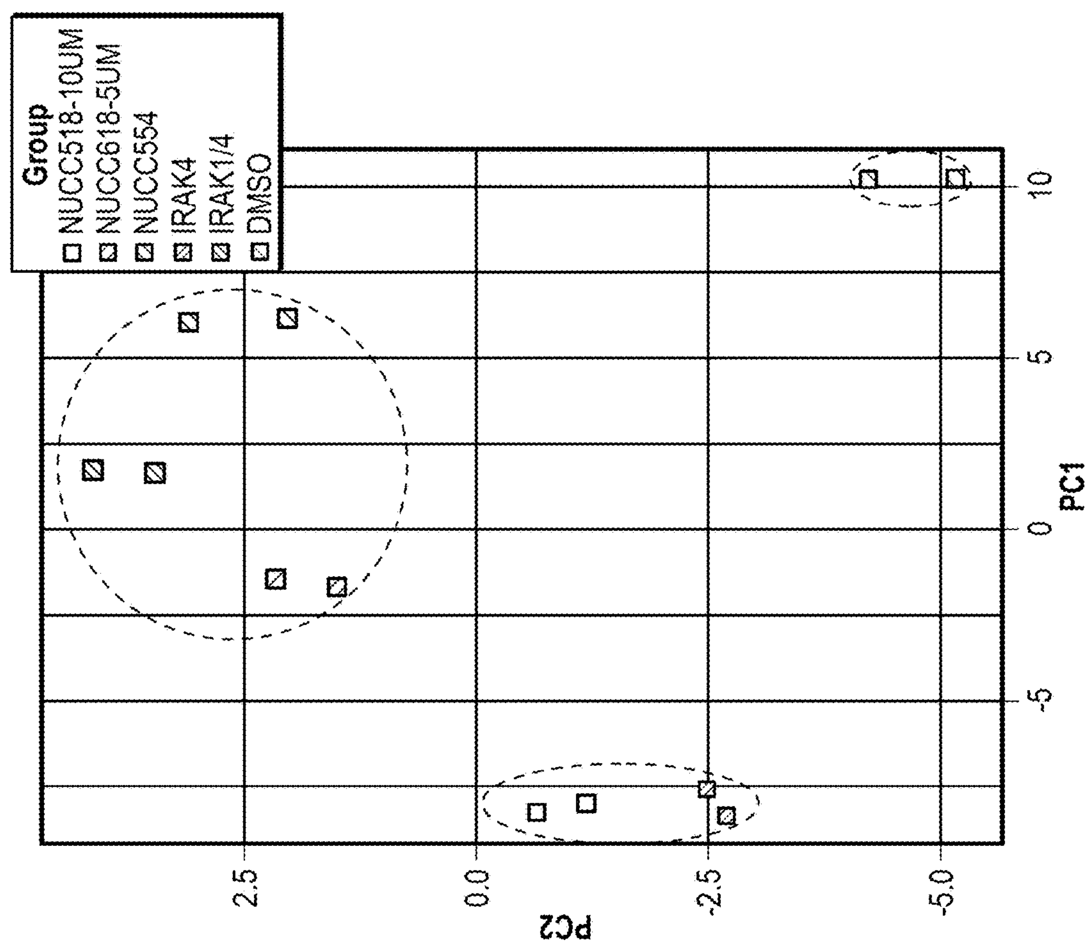
Figure 17:
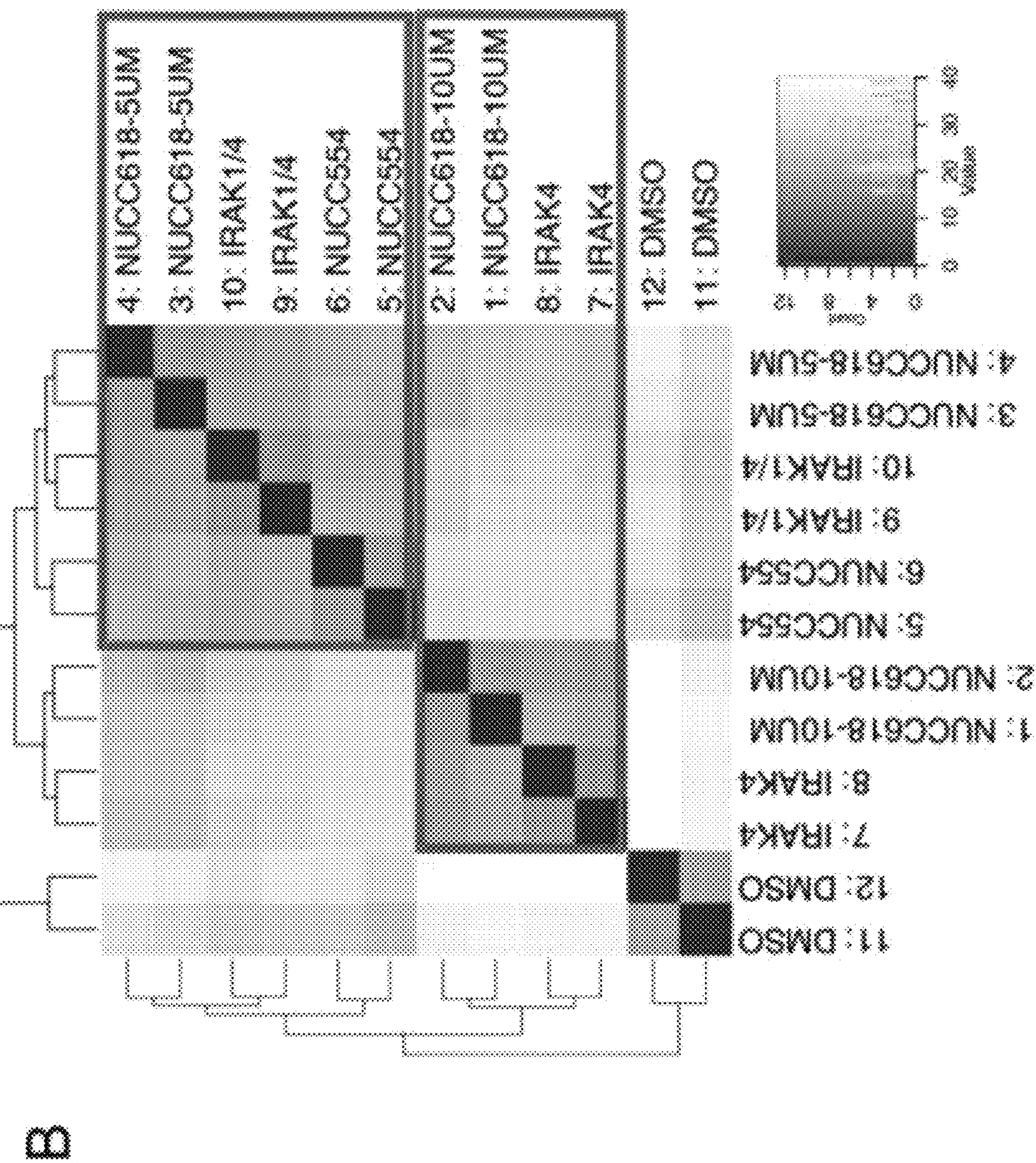
Figure 17:
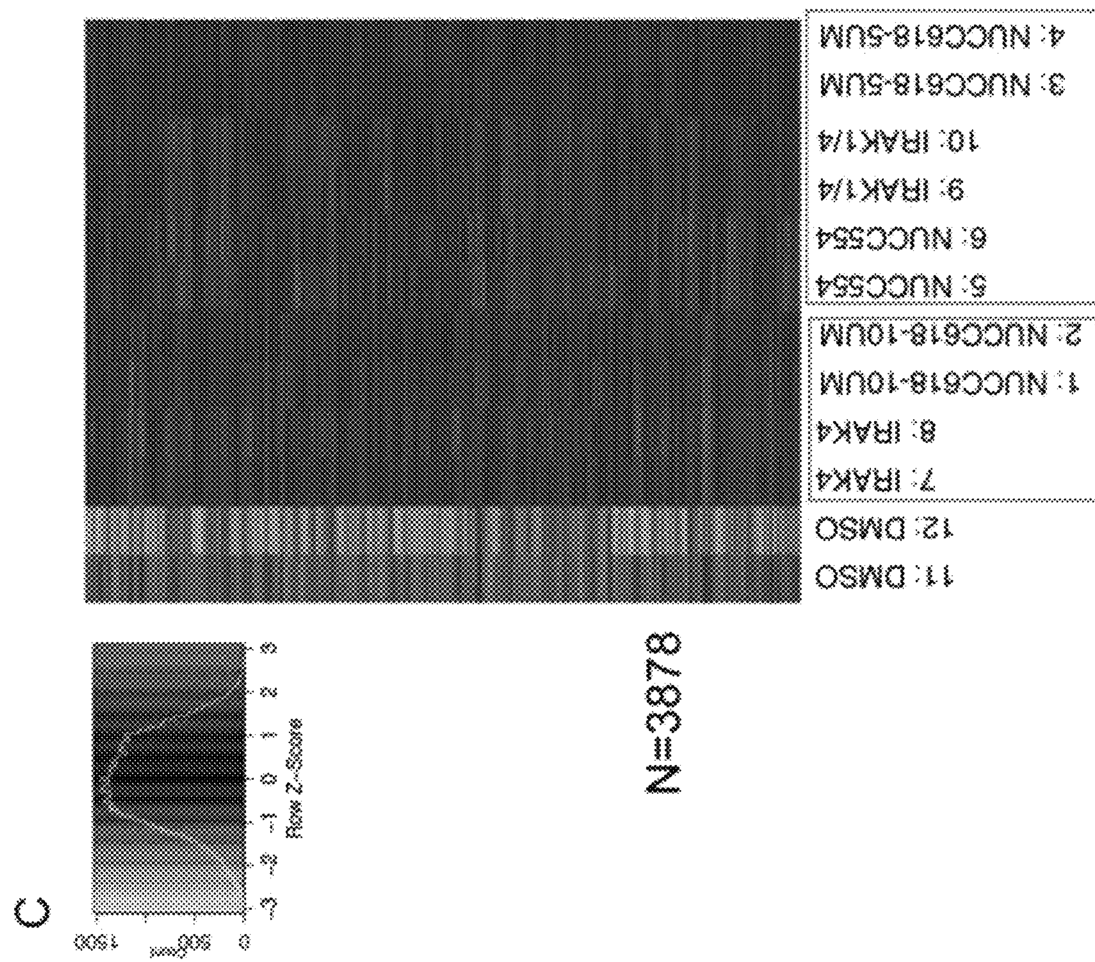
Figure 17:
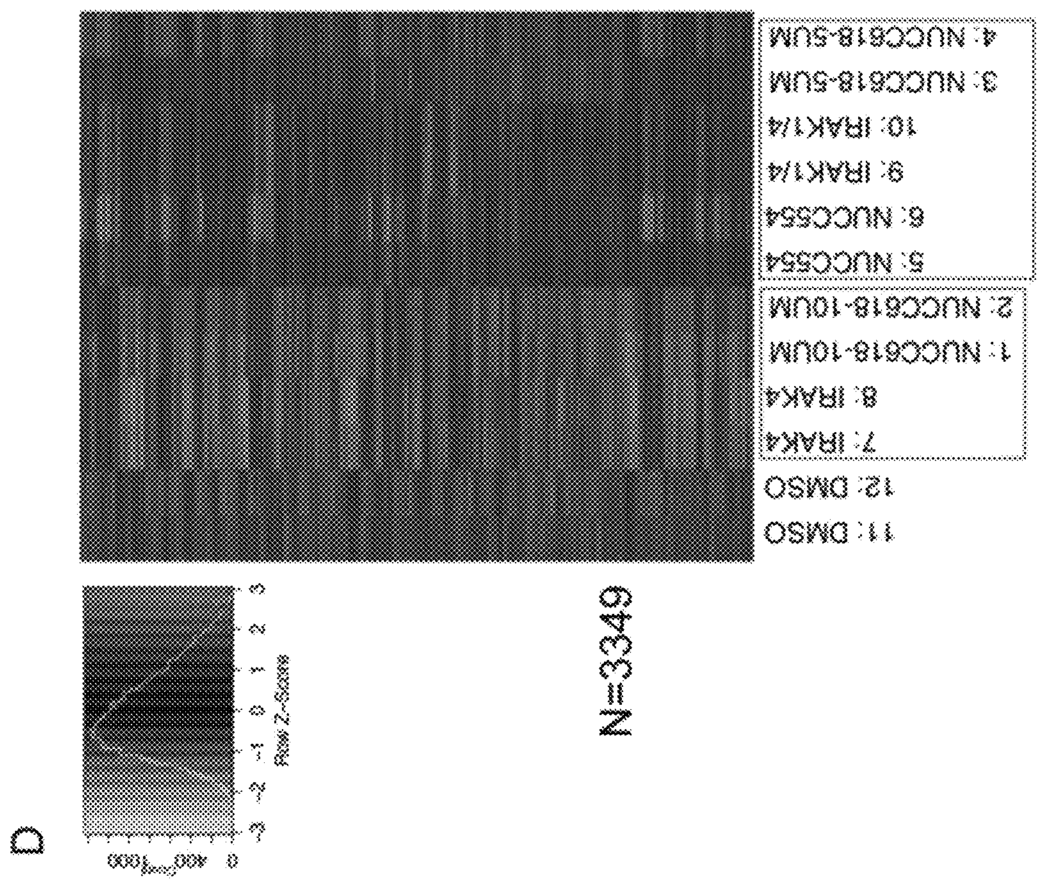

FIG. 17. Comparison of novel IRAK4 inhibitors (NUCC numbers) with commercially available IRAK inhibitors (referred to here as IRAK1/4 and IRAK4) on gene expression in leukemia cells as determined by RNA-seq. SEM cells were maintained in IMDM medium with 10% FBS. NUCC0200618 (5 uM or 10 uM), NUCC0200554(10 uM), IRAK1/4 inhibitor (10 uM) and IRAK4 inhibitor (500 nM) were used to treat SEM cells for 3 days. SEM cells were harvested and used for total RNA-seq. A: PCA plot of each group with different treatments. NUCC0200618 (10 uM) and IRAK4 inhibitors group together (medium red oval), while NUCC0200554 (10 uM), NUCC0200618 (5 uM) and the IRAK1/4 inhibitor have very similar profiles (large red oval), indicating that the Northwestern inhibitors have the same target specificity in cells as the commercially available IRAK inhibitors. DMSO treated cells group together, and far away from inhibitor treated cells (small red oval). B: Distance plot of each group with the indicated treatments. C: Heatmap of upregulated genes in any treatment D: Heatmap of downregulated genes in any treatment compared to the vehicle control (DMSO).

DETAILED DESCRIPTION

The present invention is described herein using several definitions, as set forth below and throughout the application.

Definitions

Unless otherwise specified or indicated by context, the terms “a”, “an”, and “the” mean “one or more.” For example, “a compound” should be interpreted to mean “one or more compounds.”

As used herein, “about,” “approximately,” “substantially,” and “significantly” will be understood by persons of ordinary skill in the art and will vary to some extent on the context in which they are used. If there are uses of these terms which are not clear to persons of ordinary skill in the art given the context in which they are used, “about” and “approximately” will mean plus or minus <10% of the particular term and “substantially” and “significantly” will mean plus or minus >10% of the particular term.

As used herein, the terms “include” and “including” have the same meaning as the terms “comprise” and “comprising” in that these latter terms are “open” transitional terms that do not limit claims only to the recited elements succeeding these transitional terms. The term “consisting of,” while encompassed by the term “comprising,” should be interpreted as a “closed” transitional term that limits claims only to the recited elements succeeding this transitional term. The term “consisting essentially of,” while encompassed by the term “comprising,” should be interpreted as a “partially closed” transitional term which permits additional elements succeeding this transitional term, but only if those additional elements do not materially affect the basic and novel characteristics of the claim.

As used herein, a “subject” may be interchangeable with “patient” or “individual” and means an animal, which may be a human or non-human animal, in need of treatment, for example, treatment by include administering a therapeutic amount of one or more therapeutic agents that inhibit the biological activity of one or more members of the interleukin-1 signaling pathway.

A “subject in need of treatment” may include a subject having a disease, disorder, or condition that is responsive to therapy with an inhibitor of the biological activity of one or more members of the interleukin-1 signaling pathway. For example, a “subject in need of treatment” may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A “subject in need of treatment” may include a subject having a cancer that is characterized by a rearrangement in the mixed lineage leukemia gene, a so-called MLL-r cancer, that is responsive to therapy with an inhibitor of the biological activity of one or more members of the interleukin-1 signaling pathway. In particular, some leukemias such as acute lymphoblastic leukemia (ALL) or acute myelogenous leukemia (AML) have been shown to be characterized by MLL-r. However, the present inventors' findings may be applicable to other cancers that are characterized by MML-r other than ALL and AML, including, but not limited to adenocarcinoma, lymphoma, melanoma, myeloma, sarcoma, and teratocarcinoma which are shown to be characterized by MLL-r. The present inventors' findings may be applicable to cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus which are shown to be characterized by MLL-r.

As used herein, the phrase “effective amount” shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

The term “alkyl” as contemplated herein includes a straight-chain or branched alkyl radical in all of its isomeric forms. Similarly, the term “alkoxy” refers to any alkyl radical which is attached via an oxygen atom (i.e., a radical represented as “alkyl-O—*”). As used herein, an asterick “*” is used to designate the point of attachment for any radical group or substituent group.

Therapeutic Targeting of the Interleukin-1 Pathway in MLL-r Cancers

The present inventors have invented new methods of treating MLL-r cancers, including MLL-r leukemias, in a subject in need thereof. The methods typically include targeting the interleukin-1 pathway by administering a therapeutic amount of one or more therapeutic agents that inhibit the biological activity of one or more members of the interleukin-1 signaling pathway.

Therapeutic agents administered in the inventors' may inhibit the biological activity of one or more members of the interleukin-1 signaling pathway, which may include but are not limited to interleukin-1 receptor-associated kinase 2 (IRAK2), interleukin-1 receptor-associated kinase 3 (IRAK3), interleukin-1 receptor-associated kinase 4 (IRAK4), interleukin-1 ligand α (IL1α), interleukin 1 ligand β (IL1β), interleukin-1 receptor type 1 (IL1R1), interleukin-1 receptor accessory protein (IL1RAP), toll interacting protein (TOLLIP), myeloid differentiation primary response gene 88 (MYD88), interleukin-1 receptor-associated kinase 1 (IRAK1), tumor necrosis factor receptor-associated factor 6 (TRAF6), and any combination thereof. The therapeutic agents may include, but are not limited to, small molecule inhibitors and/or peptide inhibitors. The therapeutic agents may include therapeutic agents known in the art or described herein, such as the new small molecule inhibitors of IRAK4 described herein. The therapeutic agents may be formulated as pharmaceutical compositions for treating cancers associated with the MLL-r gene, such as MLL-r leukemia.

Inhibitors of members of the IL-1 signaling pathway are known in the art. For example, inhibitors of the IL-1 receptor-associated family of kinases (i.e., the IRAK-type kinases) are known in the art. So-called "acyl-2-aminobenzimidazole compounds" or "N-(1H-benzimidazol-2-yl)-benzamide compounds" have been shown to inhibit the biological activity of IRAK1 and IRAK4. (See Powers et al., Biorg & Chem. Lett. 16 (2006) 2842-2845, the content of which is incorporated herein by reference in its entirety). As such, therapeutic agents administered in the methods disclosed herein may include acyl-2-aminobenzimidazole compounds or N-(1H-benzimidazol-2-yl)-benzamide compounds. In some embodiments, the compounds have the following formula I:

I

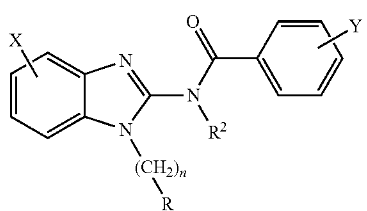

where n is 0, 1, 2, or 3;

R is H, alkyl (e.g., $C_1$-$C_6$ alkyl), allyl, cycloalkyl (e.g., $C_3$-$C_6$ cycloalkyl), alkoxy (e.g., $C_1$-$C_6$ alkoxy), alkylester (e.g., $C_1$-$C_6$ alkylester), α-(γ-butyrolactone), (2-tetrahydrofuranyl)methyl, hydroxyl, amino, alkylamino (e.g., $C_1$-$C_6$ alkylamino), dialkylamino (e.g., $C_1$-$C_6$ dialkylamino), and morpholinyl (e.g., N-morpholinyl).

$R^2$ is H, alkyl (e.g., $C_1$-$C_6$ alkyl), or allyl;

optionally the compound is substituted at one or more X positions with alkyl (e.g., $C_1$-$C_6$ alkyl), alkoxy (e.g., $C_1$-$C_6$ alkyl), halo (e.g., Cl or F), nitro, carboxyl, alkylester, or $SO_2(CH_2)_2Me$;

and optionally the compound is substituted at one or more Y positions with alkyl (e.g., $C_1$-$C_6$ alkyl), alkoxy (e.g., $C_1$-$C_6$ alkyl), halo (e.g., Cl or F), nitro, or cyano.

In further embodiments, the compound having formula I is substituted at one or more X positions with a substituent selected from the group consisting of 5-Cl, 5-F, 5-$CH_3$, 5-$OCH_3$, 5-$CO_2CH_3$, 5-$SO_2(CH_2)_2Me$, 5-$NO_2$, 4-$NO_2$, 5,6-di-F, 5,6-di-Cl, 4,5-di-F, and 5,6-di-$CH_3$. In even further embodiments, the compound having formula I is substituted at one or more Y positions with a substituent selected from the group consisting of 3-$NO_2$, 3-CN, 3-$NO_2$-4-F, 3-$NO_2$-4-Me, 3-Cl, 3,4-di-Cl, 4-$NO_2$, and 4-OMe.

Specifically, the compound having formula I may include the following compound having formula Ia:

Ia

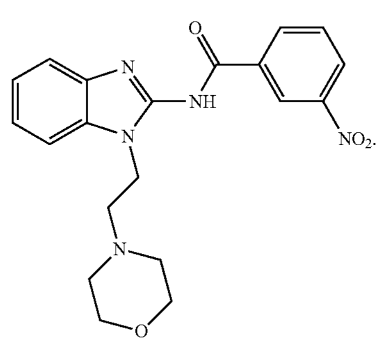

In addition, so-called "indolo[2,3-c]quinolone compounds" have been shown to inhibit the biological activity of IRAK4. (See Tumey et al., Biorg & Med. Chem. Lett. 24 (2014) 2066-2072, the content of which is incorporated herein by reference in its entirety). As such, therapeutic agents administered in the methods disclosed herein may include indolo[2,3-c]quinolone compounds. In some embodiments, the compound has a formula II:

II

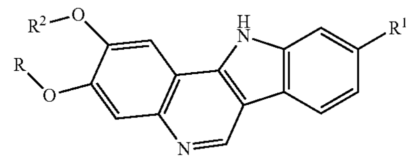

where R is selected from the group consisting of:

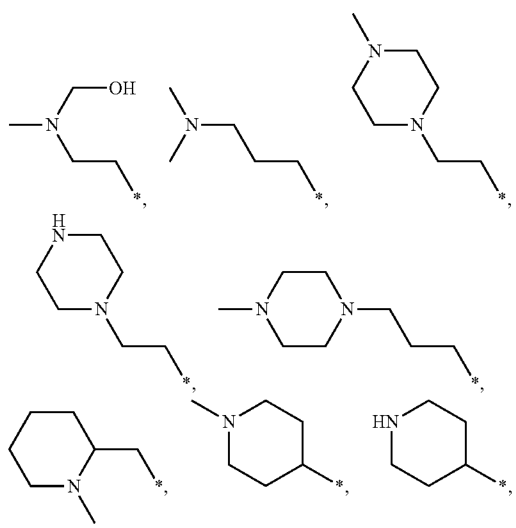

-continued

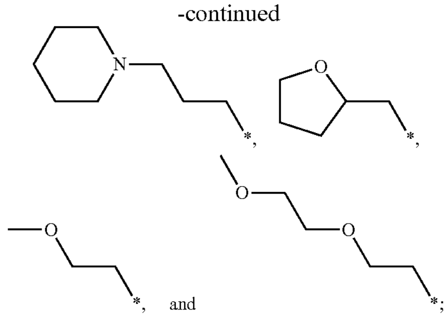

$R^1$ is cyano or nitro; and $R^2$ is H or alkyl (e.g., $C_1$-$C_6$ alkyl).

Specifically, the compound having formula II may include the following compound having formula IIa:

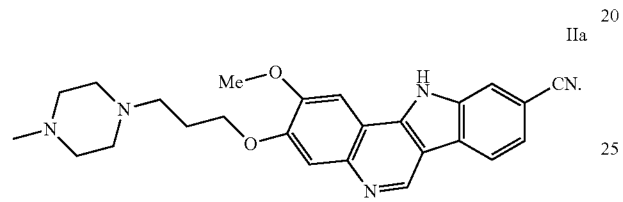

Other known inhibitors of the IRAK family of kinases include thiazole amide compounds, imidazo[1,2-α]pyridine compounds and derivatives thereof (see Buckley et al., Bioorg Med Chem Lett. (2008) 18(12):3211-3214; Buckely et al., Biorg Med Chem Lett. (2008) 18(12):3291-3295); and Buckley et al. Bioorg Med Chem Lett. (2008) 18(12):3656-60, the contents of which are incorporated herein by reference in their entireties), oxazole carboxylic acid amide compounds and derivatives (see International Published Application No. WO 2011/043371, the content of which is incorporated herein by reference in its entirety), heteroaryl substituted pyridyl compounds and derivatives (see International Published Application No. WO 2014/074675, the content of which is incorporated herein by reference in its entirety), 2-aminopyrimidine compounds and derivatives (see International Published Application No. WO 2014/058685, the content of which is incorporated herein by reference in its entirety), indazolyl triazole compounds and derivatives (see International Published Application No. WO 2012/084704, the content of which is incorporated herein by reference in its entirety), pyrimidine pyrazolyl compounds and derivatives (see International Published Application No. WO 2014/008992), pyridazinone-amides compounds and derivatives (see International Published Application No. WO 2014/121931, the content of which is incorporated herein by reference in its entirety), macrocyclic pyridazinone compounds and derivatives (see WO 2014/121942, the content of which is incorporated herein by reference in its entirety), and pyrazolo [1,5a] pyrimidine and thieno [3,2b] pyrimidine compounds and derivatives (see International Published Application No. WO 2012/007375, the content of which is incorporated herein by reference in its entirety). As such, these compounds also may be administered as therapeutic agents in the presently disclosed methods.

Further to the prior art inhibitors of IRAK4, the present inventors have synthesized new compounds that may be utilized in pharmaceutical compositions and methods for treating subjects in need thereof. For example, the disclosed compounds may be utilized in pharmaceutical compositions and methods for treating subjects having a disease or disorder associated with IRAK4 activity in which the disclosed compounds function as inhibitors of IRAK4.

In some embodiments, the disclosed compounds, which optionally are inhibitors of IRAK4, may be imidazo(1,2-a) pyridine derivatives (e.g., amido-substituted imidazo(1,2-a) pyridine derivatives). In particular, the disclosed compound may have a formula III:

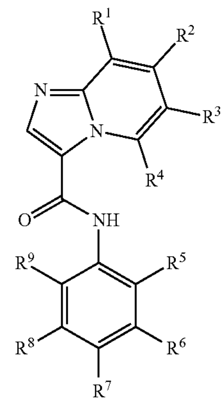

III wherein $R^1$, $R^2$, $R^3$, and $R^4$ are the same or different and each of $R^1$, $R^2$, $R^3$, and $R^4$ is independently —$(CH_2)_m$R', wherein m is 0-6 and R' is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino;

wherein $R^5$, $R^6$, $R^7$, $R^8$, and $R^9$ are the same or different and each of $R^5$, $R^6$, $R^7$, $R^8$, and $R^9$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and optionally at least one of $R^1$, $R^2$, $R^3$, $R^4$, $R^5$, $R^6$, $R^7$, $R^8$, and $R^9$ is not hydrogen, optionally at least one of $R^1$, $R^2$, $R^3$, $R^4$ is alkyl-heteroalkyl, or optionally at least one of $R^5$, $R^6$, $R^7$, $R^8$, and $R^9$ is halo.

In some embodiments, the disclosed compounds have a formula IIIa:

IIIa

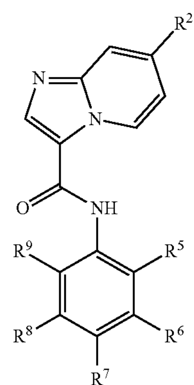

wherein $R^2$ is —$(CH_2)_m$R', wherein m is 0-6 and R' is selected from halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and wherein $R^5$, $R^6$, $R^7$, $R^8$, and $R^9$ are the same or different and each of $R^5$, $R^6$, $R^7$, $R^8$, and $R^9$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino.

In further embodiments, the disclosed compounds have a formula IIIb:

IIIb

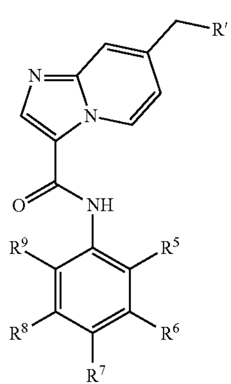

wherein R' is selected from halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and wherein $R^5$, $R^6$, $R^7$, $R^8$, and $R^9$ are the same or different and each of $R^5$, $R^6$, $R^7$, $R^8$, and $R^9$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino.

In particular, the disclosed compounds may have a formula IIIb wherein R' is heterocycloalkyl, which optionally is substituted with alkyl, halo, hydroxyl, or amino, and/or at least one of $R^5$, $R^6$, $R^7$, $R^8$, and $R^9$ is halo. For example, the disclosed compound may have a formula selected from:

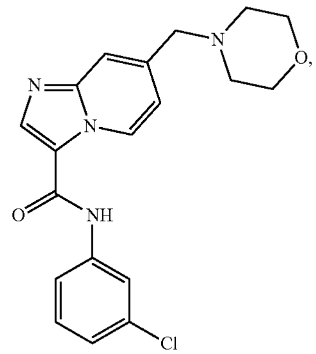

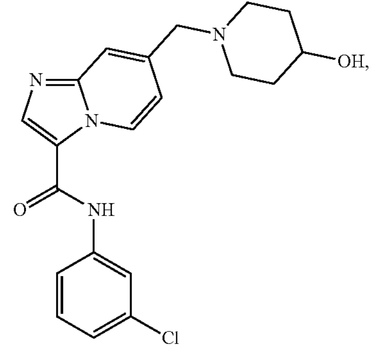

-continued

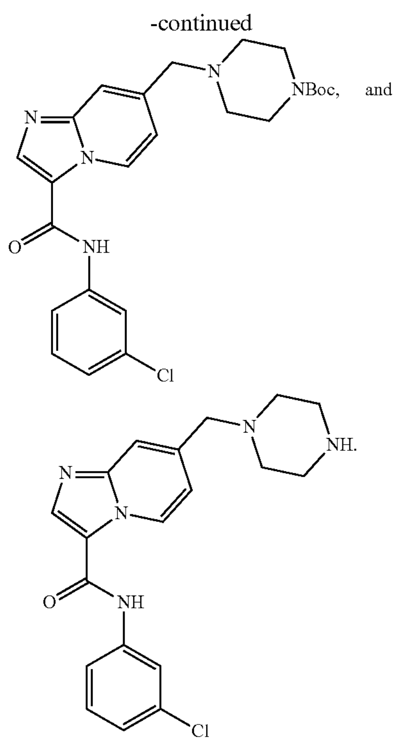

In some embodiments, the newly disclosed compounds, which optionally are inhibitors of IRAK4, may be substituted imidazole compound derivatives. For example, the disclosed compounds may be benzamido-substituted, phenyl-substituted imidazole compound derivatives. In particular, the disclosed compound may have a formula IV:

IV

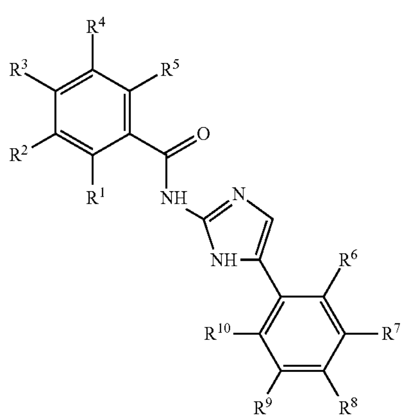

wherein $R^1$, $R^2$, $R^3$, $R^4$, and $R^5$ are the same or different and each of $R^1$, $R^2$, $R^3$, $R^4$, and $R^5$ is independently —$(CH_2)_m$R', wherein m is 0-6 and R' is selected from hydrogen, halo, amino or alkyl-substituted amino (e.g., $C_1$-$C_6$ alkylamino or $C_1$-$C_6$ dialkylamino), hydroxyl, cyano, nitro, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino;

wherein $R^6$, $R^7$, $R^8$, $R^9$, and $R^{10}$ are the same or different and each of $R^5$, $R^6$, $R^7$, $R^8$, $R^9$, and $R^{10}$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, nitro, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and optionally at least one of $R^1$, $R^2$, $R^3$, $R^4$, $R^5$, $R^6$, $R^7$, $R^8$, $R^9$, and $R^{10}$ is not hydrogen, optionally at least one of $R^1$, $R^2$, $R^3$, $R^4$, and $R^5$ is halo or alkyoxy, or optionally at least one of $R^6$, $R^7$, $R^8$, $R^9$, and $R^{10}$ is amino, alkyl-substituted amino, dialkyl-substituted amino, amido, cyano, nitro, hydroxyl, or halo.

In some embodiments, the compounds may have a formula IVa:

IVa

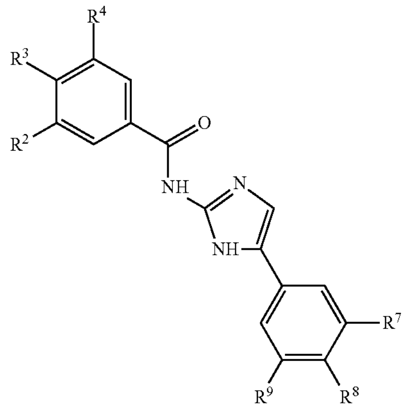

In particular, the disclosed compounds may have a formula selected from:

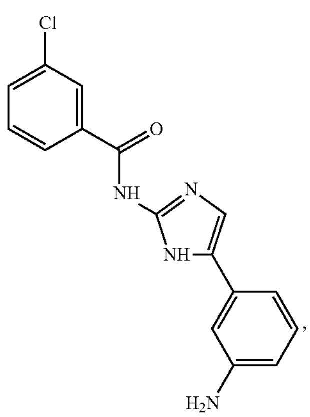

-continued

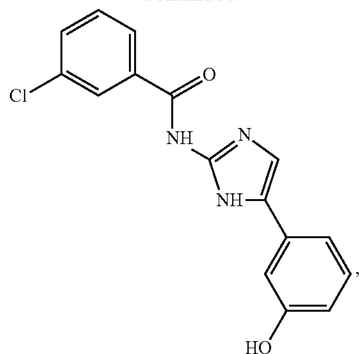

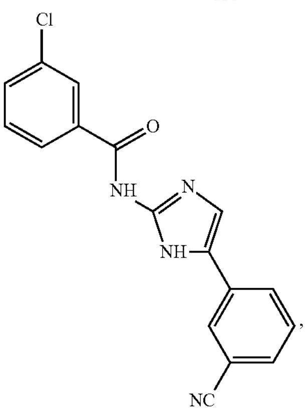

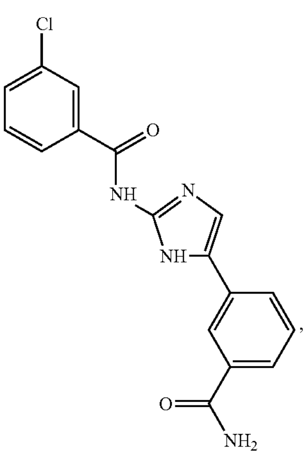

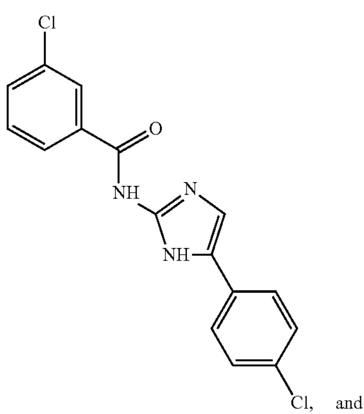

-continued

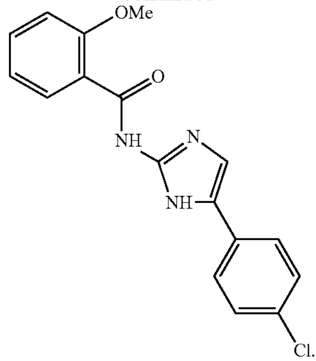

Inhibitors of the interaction between interleukin-1 ligand α (IL1α) and/or interleukin 1 ligand β (IL1β) and their receptor, the interleukin-1 receptor type 1 (IL1R1), also are known in the art. The interleukin-1 receptor antagonist (IL-1RA) is naturally occurring protein in humans that inhibits the activity of IL1α and IL1β. A recombinant form of IL-1RA called "Anakinra" is marketed as a drug for treating inflammation and cartilage damage associated with rheumatoid arthritis under the trademark Kineret® (Sobi, Inc.) Interleukin-1 receptor blockade therapy via administering IL-1RA also has been proposed for treating perinatal brain injury. (See Rosenweig et al., Frontiers in Pediatrics, October 2014, Volume 2, Article 108, the content of which is incorporated herein by reference in its entirety). Anakinra differs from native human IL-1RA in that Anakinra has an N-terminal methionine residue and Anakinra is not glycosylated. As such, therapeutic agents administered in the methods disclosed herein may include interleukin-1 receptor type 1 antagonists such as IL-1RA or recombinant or modified forms of IL-1RA such as Anakinra.

Inhibitors of myeloid differentiation primary response gene 88 (MYD88) also are known in the art. For example, a peptidomimetic called "ST2825" has been shown to inhibit MYD88 dimerization. (See Loiarro et al., J. Leukocyte Biol. 2007, 82(4): 801-810, the content of which is incorporated herein by reference in its entirety). "ST2825" is otherwise known as 4R,7R,8aR)-1'-[2-[4-[[2-(2,4-dichlorophenoxy) acetyl] amino]phenyl]acetyl]-6-oxospiro[3,4,8,8a-tetrahydro-2H-pyrrolo[2,1-b][1,3]thiazine-7,2'-pyrrolidine]-4-carboxamide and by CAS No. 894787-30-5. As such, therapeutic agents administered in the methods disclosed herein may include ST2825.

Other small molecule inhibitors of MYD88 have been reported. (See Olson et al., Scientific Reports, Sep. 18, 2015, 5:14246; the content of which is incorporate herein by reference in its entirety). These other small molecule inhibitors of MYD88 include the following compounds:

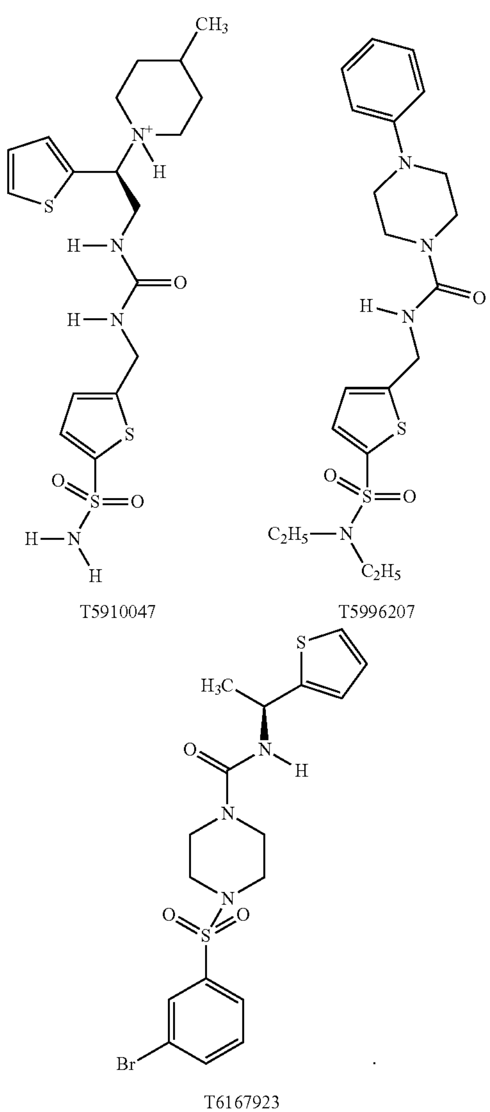

T5910047 T5996207

T6167923

As such, therapeutic agents administered in the methods disclosed herein may include T5910047, T5996207, and T6167923 and derivatives thereof.

Inhibitory peptides of the biological activity of MYD88 also are known in the art. (See Loiarro et al., 2005. J. Biol. Chem., 2800: 15809-14; the content of which is incorporated herein by reference in its entirety). In particular, a peptide called "Pepinh-MYD" has been shown to inhibit homodimerization of MYD88. (See id.). Pepinh-MYD contains a sequence of the MYD88 TIR homodimerization domain preceded by a protein transduction sequence. As such, therapeutic agents administered in the methods disclosed herein may include Pepinh-MYD or derivatives of MYD88 comprising the homodimerization domain preceded by a protein transduction sequence. (See id.).

Small molecule inhibitors of the biological activity of tumor necrosis factor receptor-associated factor 6 (TRAF6) also are known in the art. (See International Published Applications WO 2008/115259 and WO 2014/033122, the contents of which are incorporated herein by reference in their entireties). In particular, 3-[(2,5-Dimethylphenyl) amino]-1-phenyl-2-propen-1-one (CAS No. 433249-94-6), otherwise referred to as "Compound 6877002," has been shown to inhibit the biological activity of TRAF6. (See Chatzigeorgiou et al., PNAS, Feb. 18, 2014, vol. 111, no. 7, p. 2686-2691, the content of which is incorporate herein by reference in its entirety). As such, therapeutic agents administered in the methods disclosed herein may include Compound 6877002.

In addition to the use of small molecules and peptides for inhibiting the biological activity of the members of the IL-1 signaling pathway, expression of one or more members of the IL-1 signaling pathway also may be inhibited via RNA interference (RNAi). As such, therapeutic agents administered in the methods disclosed herein may include therapeutic agents for administering RNAi therapy as known in the art. (See, e.g., Davidson et al., Nat. Rev. Genet. 12, 329-340 (May 2011); Wittrup et al., Nat. Rev. Genet. 16, 543-552 (August 2015); Bobbin et al., Ann. Rev. Pharma Toxic. Vol. 56, 103-122 (January 2016); the contents of which are incorporated herein by reference in their entireties). Nucleic acid inhibitors utilized in the disclosed methods may include, but are not limited to shRNAs and siRNAs that inhibit expression of one or more members of the IL-1 signaling pathway.

Formulations and Administration

The formula of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds (e.g., pharmaceutically acceptable salts).

The disclosed therapeutic agents may be effective in inhibiting cell proliferation of cancer cells, including mixed lineage leukemia cells. Cell proliferation and inhibition thereof by the presently disclosed therapeutic agents may be assessed by cell viability methods disclosed in the art including colorimetric assays that utilize dyes such as MTT, XTT, and MTS to assess cell viability. Preferably, the disclosed therapeutic agents have an $IC_{50}$ of less than about 10 μM, 5 μM, 1 μM, or 0.5 μM in the selected assay.

The therapeutic agents utilized in the methods disclosed herein may be formulated as pharmaceutical compositions that include: (a) a therapeutically effective amount of one or more of the therapeutic agents as disclosed herein; and (b) one or more pharmaceutically acceptable carriers, excipients, or diluents. The pharmaceutical composition may include the therapeutic agent in a range of about 0.1 to 2000 mg (preferably about 0.5 to 500 mg, and more preferably about 1 to 100 mg). The pharmaceutical composition may be administered to provide the therapeutic agent at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a subject (e.g., after about 1, 2, 3, 4, 5, or 6 hours post-administration), the concentration of the therapeutic agent at the site of action is about 2 to 10 μM.

The therapeutic agents utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The therapeutic agents utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The therapeutic agents utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The therapeutic agents utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The therapeutic agents utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the therapeutic agents may be adapted for administration by any appropriate route, for example by the oral (including buccal or sublingual), or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Illustrative Embodiments

The following embodiments are illustrative and are not intended to limit the scope of the claimed subject matter.

Embodiment 1. A method for treating a cancer characterized by a rearrangement in the mixed lineage leukemia gene (MLL-r) in a subject in need thereof, the method comprising administering a therapeutic amount of a therapeutic agent that inhibits the biological activity of a member of the interleukin-1 signaling pathway.

Embodiment 2. The method of embodiment 1, wherein the cancer is MLL-r leukemia.

Embodiment 3. The method of embodiment 1, wherein the member of the interleukin 1 signaling pathway is selected from the group consisting of interleukin-1 ligand α (IL1α), interleukin 1 ligand β (IL1 β), interleukin-1 receptor type 1 (IL1R1), interleukin-1 receptor accessory protein (IL1RAP), toll interacting protein (TOLLIP), myeloid differentiation primary response gene 88 (MYD88), interleukin-1 receptor-associated kinase 1 (IRAK1), interleukin-1 receptor-associated kinase 2 (IRAK2), interleukin-1 receptor-associated kinase 3 (IRAK3), interleukin-1 receptor-associated kinase 4 (IRAK4), and tumor necrosis factor receptor-associated factor 6 (TRAF6).

Embodiment 4. The method of embodiment 1, wherein the therapeutic agent inhibits the biological activity of interleukin-1 receptor-associated kinase 1 (IRAK1) and/or the biological activity of interleukin-1 receptor-associated kinase 4 (IRAK4).

Embodiment 5. The method of any of the foregoing embodiments, wherein the therapeutic agent is an N-(1H-benzimidazol-2-yl)-benzamide compound.

Embodiment 6. The method of any of the foregoing embodiments, wherein the therapeutic agent is a compound having the formula I:

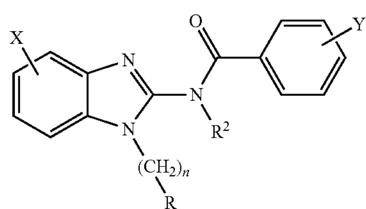

I n is 0, 1, 2, or 3;

R is H, alkyl (e.g., $C_1$-$C_6$ alkyl), allyl, cycloalkyl (e.g., $C_3$-$C_6$ cycloalkyl), alkoxy (e.g., C1-C6 alkoxy), alkylester, α-(γ-butyrolactone), (2-tetrahydrofuranyl)methyl, hydroxyl, amino, $C_1$-$C_6$ alkyl amino, $C_1$-$C_6$ dialkyl amino, and morpholinyl (e.g., N-morpholinyl);

$R^2$ is H, alkyl (e.g., $C_1$-$C_6$ alkyl), or allyl;

optionally the compound is substituted at one or more X positions with alkyl (e.g., $C_1$-$C_6$ alkyl), alkoxy (e.g., $C_1$-$C_6$ alkyl), halo (e.g., Cl or F), nitro, carboxyl, alkylester, or $SO_2(CH_2)_2Me$;

and optionally the compound is substituted at one or more Y positions with alkyl (e.g., $C_1$-$C_6$ alkyl), alkoxy (e.g., $C_1$-$C_6$ alkyl), halo (e.g., Cl or F), nitro, or cyano.

Embodiment 7. The method of embodiment 6, wherein the compound is substituted at one or more X positions with a substituent selected from the group consisting of 5-Cl, 5-F, 5-$CH_3$, 5-$OCH_3$, 5-$CO_2CH_3$, 5-$SO_2(CH_2)_2Me$, 5-$NO_2$, 4-$NO_2$, 5,6-di-F, 5,6-di-Cl, 4,5-di-F, and 5,6-di-$CH_3$.

Embodiment 8. The method of embodiment 6 or 7, wherein the compound is substituted at one or more Y positions with a substituent selected from the group consisting of 3-$NO_2$, 3-CN, 3-$NO_2$-4-F, 3-$NO_2$-4-Me, 3-Cl, 3,4-di-Cl, 4-$NO_2$, and 4-OMe.

Embodiment 9. The method of any of the foregoing embodiments wherein the therapeutic agent is a compound having the formula Ia:

Ia

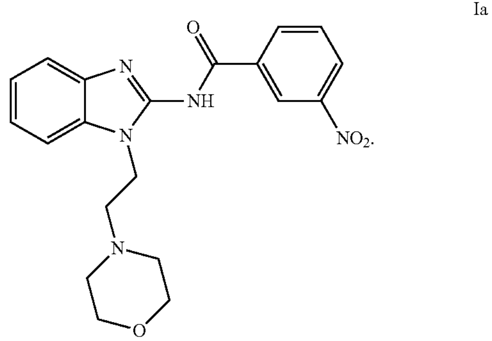 [SMILES: O=C(Nc1nc2ccccc2n1CCN1CCOCC1)c1cccc([N+](=O)[O-])c1]

Embodiment 10. The method of any of embodiments 1-4, wherein the therapeutic agent is an indolo[2,3-c]quinolone compound.

Embodiment 11. The method of any of embodiments 1-4 and 10, wherein the therapeutic agent is a compound having the formula II:

II

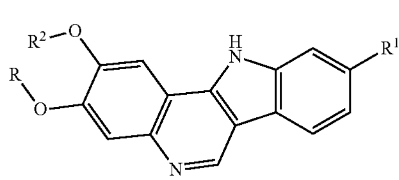

R is selected from the group consisting of:

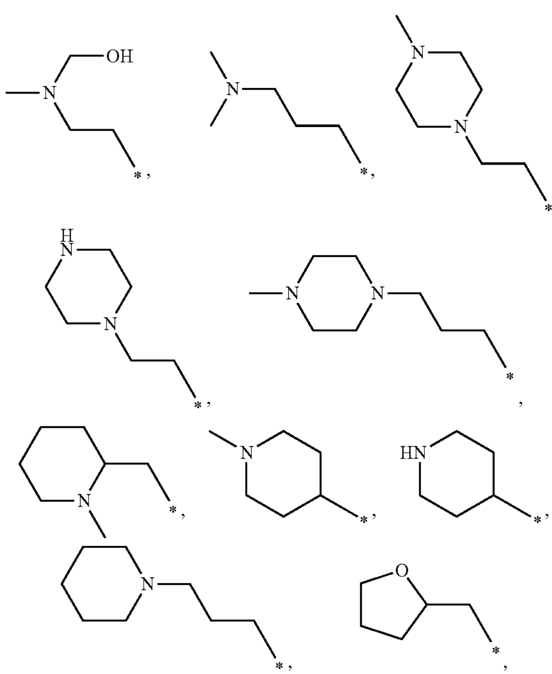

-continued

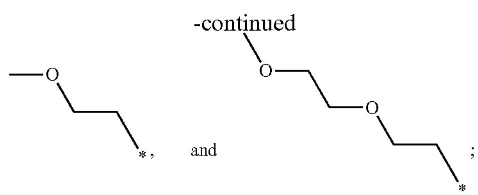

$R^1$ is cyano or nitro; and $R^2$ is H or alkyl (e.g., $C_1$-$C_6$ alkyl).

Embodiment 12. The method of any of embodiments 1-4, 10, and 11, wherein the therapeutic agent is a compound having the formula IIa:

IIa

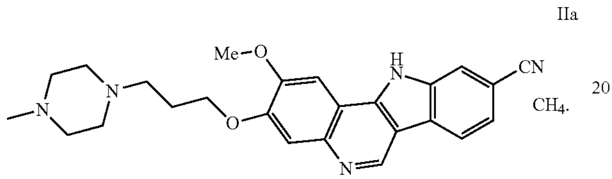

Embodiment 13. The method of any of embodiments 1-4, wherein the therapeutic agent is a compound selected from the group consisting of imidazo[1,2-a]pyridine compounds and derivatives, oxazole carboxylic acid amide compounds and derivatives, heteroaryl substituted pyridyl compounds and derivatives, 2-aminopyrimidine compounds and derivatives, indazolyl triazole compounds and derivatives, pyrimidine pyrazolyl compounds and derivatives, pyridazinone-amides compounds and derivatives, macrocyclic pyridazinone compounds and derivatives, and pyrazolo [1,5a] pyrimidine compounds and derivatives, and thieno [3,2b] pyrimidine compounds and derivatives.

Embodiment 14. The method of embodiment 1, wherein the therapeutic agent is an interleukin-1 receptor type 1 antagonist.

Embodiment 15. The method of embodiment 14, wherein the therapeutic agent is Anakira.

Embodiment 16. The method of embodiment 1, wherein the therapeutic agent inhibits the biological activity of myeloid differentiation primary response gene 88 (MYD88).

Embodiment 17. The method of embodiment 15, wherein the therapeutic agent is an inhibitory peptide. (See Loiarro et al., 2005. J. Biol. Chem., 2800: 15809-14; the content of which is incorporated herein by reference in its entirety).

Embodiment 18. The method of embodiment 16, wherein the therapeutic agent is selected from a group consisting of T5910047, T5996207, and T6167923.

Embodiment 19. The method of embodiment 16, wherein the therapeutic agent is ST2825.

Embodiment 20. The method of embodiment 1, wherein the therapeutic agent inhibits the biological activity of tumor necrosis factor receptor-associated factor 6 (TRAF6).

Embodiment 21. The method of embodiment 20, wherein the therapeutic agent is an inhibitory peptide.

Embodiment 22. The method of embodiment 20, wherein the therapeutic agent is Compound 6877002.

Embodiment 23. The method of any of embodiments 1-4, wherein the therapeutic agent is an imidazo(1,2-a)pyridine derivative compound (e.g., an amido-substituted imidazo(1, 2-a)pyridine derivative compound).

Embodiment 24. The method of embodiments 23, wherein the compound has a formula III:

III

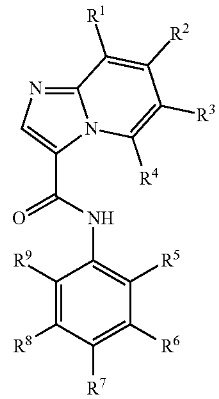

wherein $R^1$, $R^2$, $R^3$, and $R^4$ are the same or different and each of $R^1$, $R^2$, $R^3$, and $R^4$ is independently —$(CH_2)_m$R', wherein m is 0-6 and R' is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino;

wherein $R^5$, $R^6$, $R^7$, $R^8$, and $R^9$ are the same or different and each of $R^5$, $R^6$, $R^7$, $R^8$, and $R^9$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and optionally at least one of $R^1$, $R^2$, $R^3$, $R^4$, $R^5$, $R^6$, $R^7$, $R^8$, and $R^9$ is not hydrogen, optionally at least one of $R^1$, $R^2$, $R^3$, $R^4$ is alkyl-heteroalkyl, or optionally at least one of $R^5$, $R^6$, $R^7$, $R^8$, and $R^9$ is halo.

Embodiment 25. The method of embodiment 23 or 24, wherein the compound has a formula IIIa:

IIIa

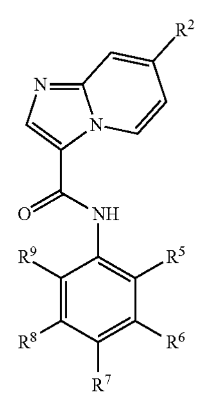

Embodiment 26. The method of any of embodiments 23-25, wherein the compounds has a formula IIIb:

IIIb

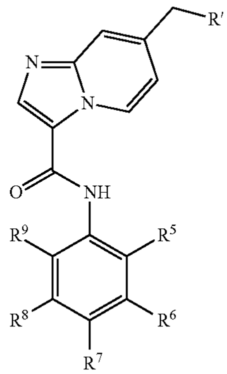

Embodiments 27. The method of any of embodiments 23-26 wherein the compound has a formula selected from:

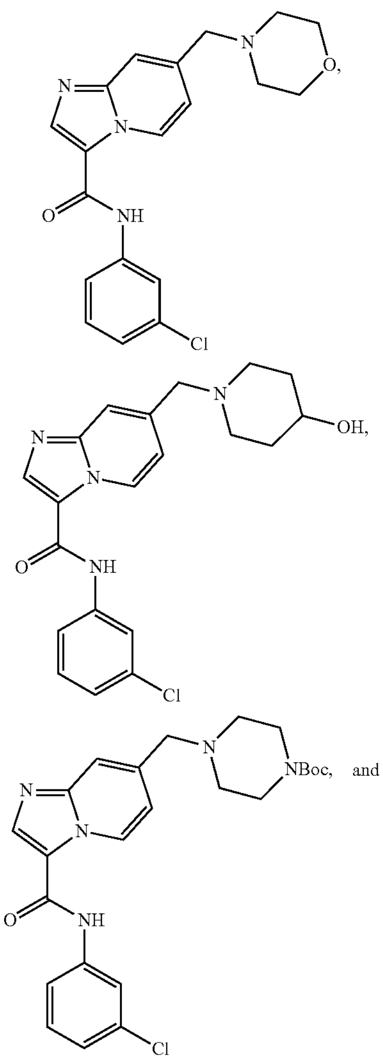

-continued

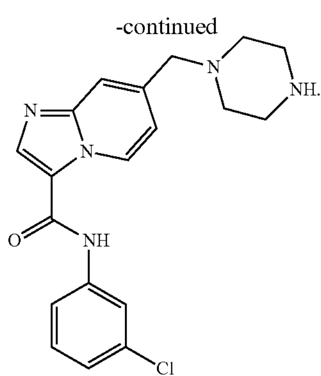

Embodiment 28. The method of any of embodiments 1-4, wherein the compound is a substituted imidazole compound derivative (e.g., benzamido, phenyl-substituted imidazole compound derivative).

Embodiment 29. The method of embodiment 28, wherein the compound has a formula IV:

IV wherein $R^1$, $R^2$, $R^3$, $R^4$, and $R^5$ are the same or different and each of $R^1$, $R^2$, $R^3$, $R^4$, and $R^5$ is independently —$(CH_2)_m$R', wherein m is 0-6 and R' is selected from hydrogen, halo, amino or alkyl-substituted amino (e.g., $C_1$-$C_6$ alkylamino or $C_1$-$C_6$ dialkylamino), hydroxyl, cyano, nitro, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino;

wherein $R^6$, $R^7$, $R^8$, $R^9$, and $R^{10}$ are the same or different and each of $R^5$, $R^6$, $R^7$, $R^8$, $R^9$, and $R^{10}$ is independently —$(CH_2)_n$R", wherein n is 0-6 and R" is selected from hydrogen, halo, amino or alkyl-substituted amino (e.g., $C_1$-$C_6$ alkylamino or $C_1$-$C_6$ dialkylamino), hydroxyl, cyano, nitro, alkyl (e.g., $C_1$-$C_6$ alkyl which may be straight chain or branched), allyl, alkoxy (e.g., $C_1$-$C_6$ alkoxy which may be straight chain or branched), saturated or unsaturated cycloalkyl (e.g., $C_3$-$C_7$ cycloalkyl or phenyl) which optionally is substituted with alkyl, halo, hydroxyl, or amino, and saturated or unsaturated heterocycloalkyl (e.g., piperidinyl, piperizinyl, morpholinyl, pyridinyl) which optionally is substituted with alkyl, halo, hydroxyl, or amino; and optionally at least one of $R^1$, $R^2$, $R^3$, $R^4$, $R^5$, $R^6$, $R^7$, $R^8$, $R^9$, and $R^{10}$ is not hydrogen, optionally at least one of $R^1$, $R^2$, $R^3$, $R^4$, and $R^5$ is halo or alkyoxy, or optionally at least one of $R^6$, $R^7$, $R^8$, $R^9$, and $R^{10}$ is amino, alkyl-substituted amino, dialkyl-substituted amino, amido, cyano, nitro, hydroxyl, or halo.

Embodiment 29. The method of embodiment 27 or 28, wherein the compound has a formula IVa:

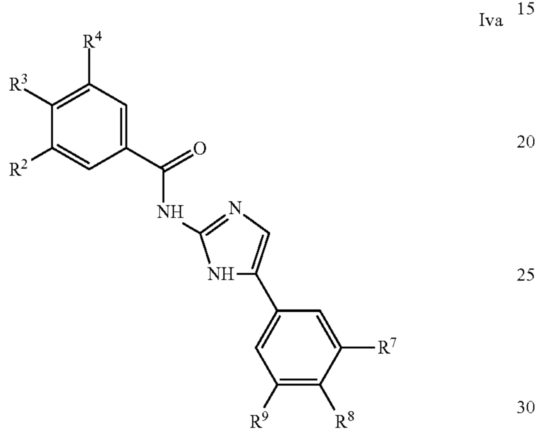

Embodiment 30. The method of any of embodiments 27-29 wherein the compound has a formula selected from:

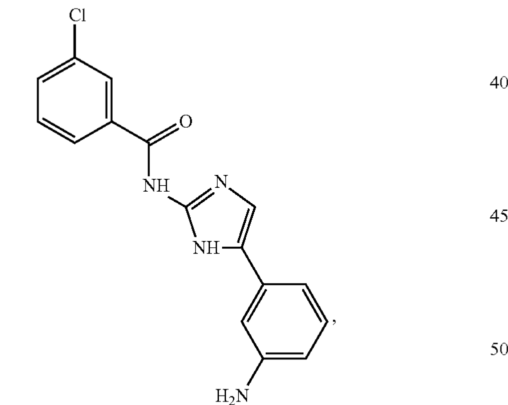

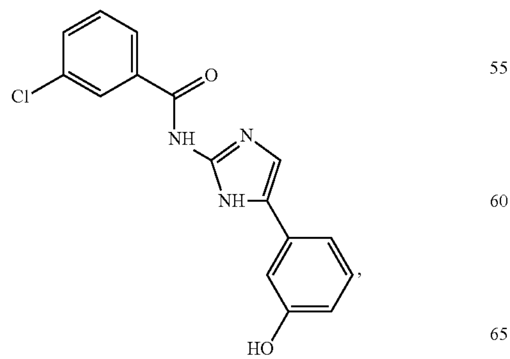

-continued

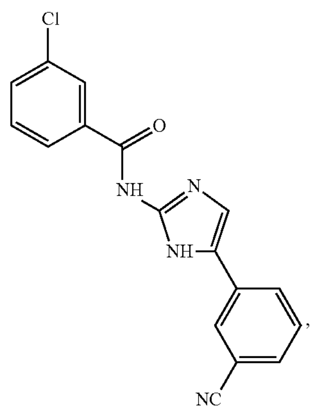

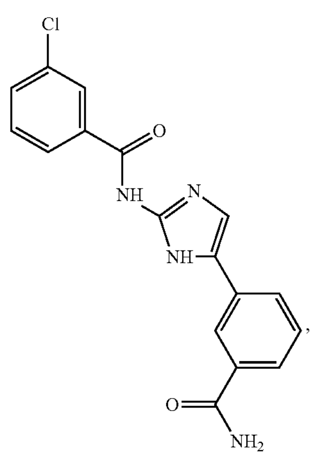

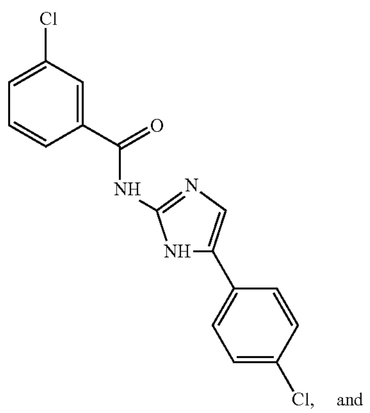

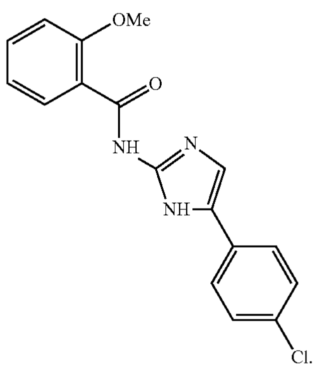

Embodiment 31. A compound having a formula III:

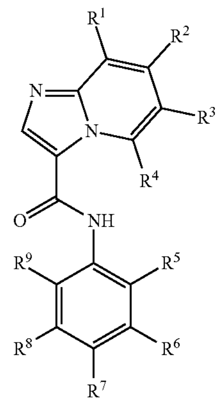

wherein $R^1$, $R^2$, $R^3$, and $R^4$ are the same or different and each of $R^1$, $R^2$, $R^3$, and $R^4$ is independently —$(CH_2)_m$R', wherein m is 0-6 and R' is selected from hydrogen, halo, amino or alkyl-substituted amino, hydroxyl, cyano, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino;

wherein $R^5$, $R^6$, $R^7$, $R^8$, and $R^9$ are the same or different and each of $R^5$, $R^6$, $R^7$, $R^8$, and $R^9$ is independently —$(CH_2)_n$R", wherein m is 0-6 and R" is selected from hydrogen, halo, amino or alkyl-substituted amino, hydroxyl, cyano, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino; and optionally at least one of $R^1$, $R^2$, $R^3$, $R^4$, $R^5$, $R^6$, $R^7$, $R^8$, and $R^9$ is not hydrogen, optionally at least one of $R^1$, $R^2$, $R^3$, $R^4$ is alkyl-heteroalkyl, or optionally at least one of $R^5$, $R^6$, $R^7$, $R^8$, and $R^9$ is halo.

Embodiment 32. The compound of embodiment 31, wherein the compound has a formula IIIa:

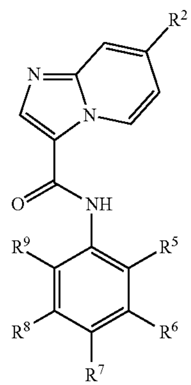

Embodiment 33. The compound of embodiment 31 or 32, wherein the compounds has a formula IIIb:

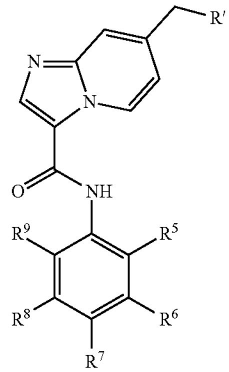

Embodiment 34. The compound of any of embodiments 31-33, wherein the compound has a formula selected from:

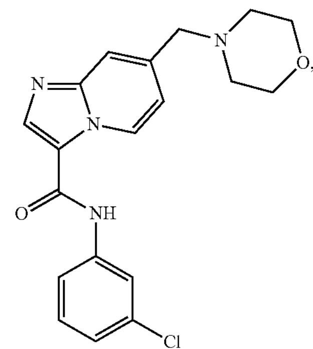

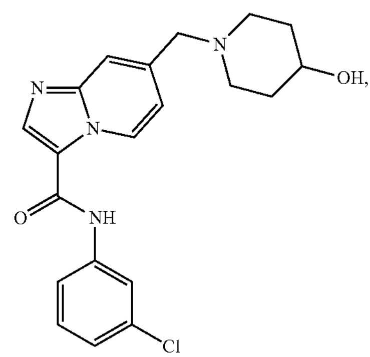

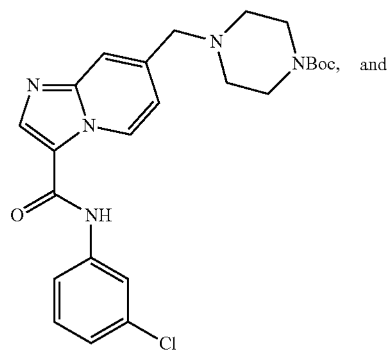

-continued

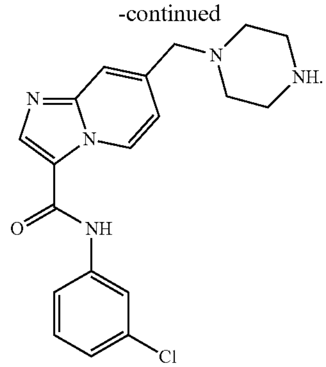

Embodiment 35. A compound having a formula IV:

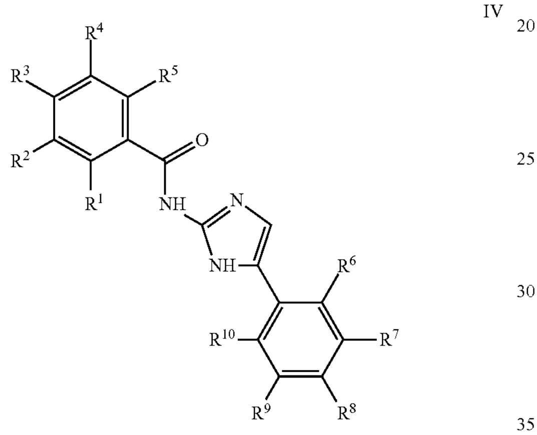

wherein $R^1$, $R^2$, $R^3$, $R^4$, and $R^5$ are the same or different and each of $R^1$, $R^2$, $R^3$, $R^4$, and $R^5$ is independently —$(CH_2)_m R'$, wherein m is 0-6 and R' is selected from hydrogen, halo, amino or alkyl-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino;

wherein $R^6$, $R^7$, $R^8$, $R^9$, and $R^{10}$ are the same or different and each of $R^5$, $R^6$, $R^7$, $R^8$, $R^9$, and $R^{10}$ is independently —$(CH_2)_n R''$, wherein n is 0-6 and R" is selected from hydrogen, halo, amino or alkyl-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino; and optionally at least one of $R^1$, $R^2$, $R^3$, $R^4$, $R^5$, $R^6$, $R^7$, $R^8$, $R^9$, and $R^{10}$ is not hydrogen, optionally at least one of $R^1$, $R^2$, $R^3$, $R^4$, and $R^5$ is halo or alkyoxy, or optionally at least one of $R^6$, $R^7$, $R^8$, $R^9$, and $R^{10}$ is amino, alkyl-substituted amino, dialkyl-substituted amino, amido, cyano, nitro, hydroxyl, or halo.

Embodiment 36. The compound of embodiment 35, wherein the compound has a formula IVa:

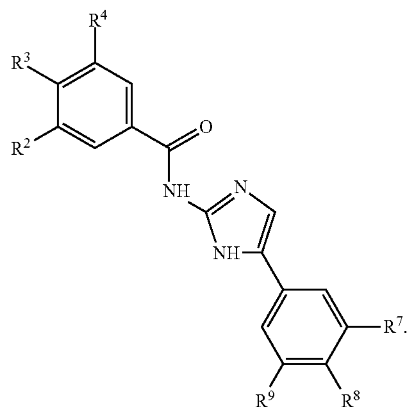

Embodiment 37. The compound of embodiment 35 or 36, wherein the compound has a formula selected from:

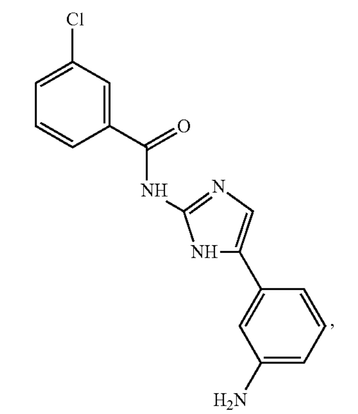

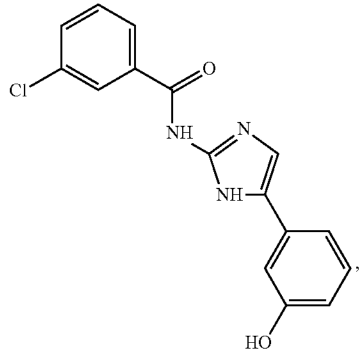

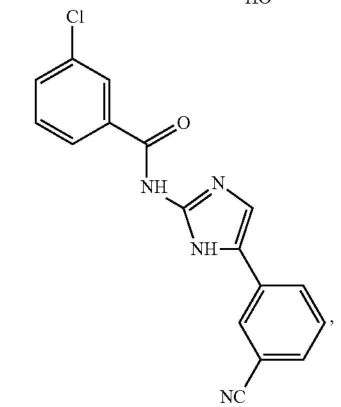

-continued

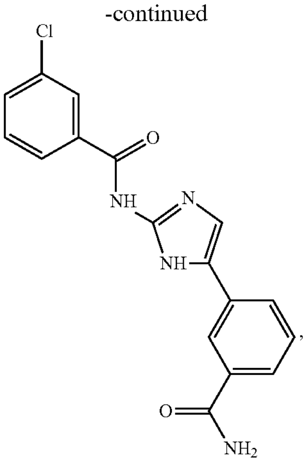

,

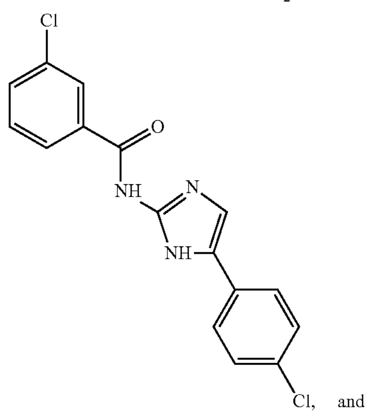

, and

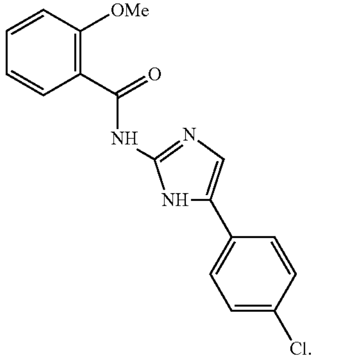

.

Embodiment 38. A pharmaceutical composition comprising the compound of any of claims 31-37 and a pharmaceutically acceptable carrier.

EXAMPLES

The following Examples are illustrative and are not intended to limit the scope of the claimed subject matter.

Example 1

Reference is made to the manuscript Liang et al., "Therapeutic Targeting of MLL Degradation Pathways in MLL-Rearranged Leukemia" Cell, Vol. 168, Issues 1-2, p 59-72, 12 Jan. 2017, the content of which is incorporated herein by reference in its entirety.

Summary

Chromosomal translocations of the mixed-lineage leukemia (MLL) gene with various partner genes result in aggressive leukemia with dismal outcomes. Despite similar expression at the mRNA level from the wild-type and chimeric MLL alleles, the chimeric protein is more stable. We report that UBE2O functions in regulating the stability of wild-type MLL in response to interleukin-1 signaling. Targeting wild-type MLL degradation impedes MLL leukemia cell proliferation, and it downregulates a specific group of target genes of the MLL chimeras and their oncogenic cofactor, the super elongation complex. Pharmacologically inhibiting this pathway substantially delays progression, and it improves survival of murine leukemia through stabilizing wild-type MLL protein, which displaces the MLL chimera from some of its target genes and, therefore, relieves the cellular oncogenic addiction to MLL chimeras. Stabilization of MLL provides us with a paradigm in the development of therapies for aggressive MLL leukemia and perhaps for other cancers caused by translocations.

Introduction

Mixed-lineage leukemias (MLLs), including acute myeloid leukemia (AML) and acute lymphoblastic leukemia (ALL), are very aggressive blood cancers with unique clinical and biological characteristics, and they are often lethal due to the development of resistance and high relapse rates with established therapies, including hematopoietic stem cell transplantation (Pigneux et al., 2015; Tomizawa et al., 2007). MLL leukemia is character characterized and driven by the recurrent translocations of an allele of the MLL gene (MLL, KMT2A) with a variety of other chromosomes (Mohan et al., 2010b). These MLL rearrangements predominantly occur in pediatric patients, including 69%-79% of infant leukemia, and they are associated with the poorest prognosis of any acute leukemia subset (Meyer et al., 2013; Mohan et al., 2010b). MLL leukemia remains a clinical challenge with an urgent need for the development of more effective targeted therapies for these aggressive cancers.

The MLL gene encodes a member of the complex of proteins associated with Setl (COMPASS) family of enzymes that are conserved from yeast to human and catalyze methylation of histone H3 lysine 4 (Miller et al., 2001; Shilatifard, 2012; Wang et al., 2009). MLL is a large protein comprised of about 4,000 amino acids (aa), but, due to proteolytic processing by Taspase I, it primarily exists in cells as two fragments, an N-terminal 320-kDa fragment (N320) and a C-terminal 180-kDa (C180) fragment (Yokoyama et al., 2011). MLL plays an essential and non-redundant role in development and hematopoiesis (Jones et al., 2012; Shilatifard, 2012). Homozygous Mll knockout mice are embryonic lethal, while Mll heterozygous mice are haploinsufficient with segmentation defects and hematological abnormalities (Yu et al., 1995).

The MLL gene has been characterized in translocations with over 70 different translocation partner genes that generate diverse oncogenic MLL chimeras possessing an MLL N-terminal fragment fused in-frame to a C-terminal portion of the partner (Meyer et al., 2013). Some of the most common fusion partners of MLL in leukemia are subunits of the super elongation complex (SEC) (Lin et al., 2010) and/or the DOT1L complex (DotCom) (Mohan et al., 2010a; Nguyen et al., 2011). The inclusion of MLL's chromatin-targeting domains in the MLL chimeras, together with their fusion to SEC and DotCom subunits, could result in aberrant recruitment of SEC and/or DotCom to deregulate MLL target genes, leading to increased proliferation and defects in differentiation (Mohan et al., 2010b; Shilatifard, 2012; Smith et al., 2011).

Gene disruption of the remaining wild-type copy of MLL, but not loss of histone methyltransferase activity, has been reported to jeopardize the initiation of MLL-AF9 leukemia in hematopoietic stem and progenitor cells (HSPCs) (Mishra et al., 2014; Thiel et al., 2010), consistent with the general requirement of MLL for embryonic hematopoiesis and the specification of postnatal HSPCs (Gan et al., 2010; Jude et al., 2007; McMahon et al., 2007). However, the existence of patient-derived MLL leukemia cell lines (such as ML2) with a deletion of the entire wild-type MLL locus suggests that wild-type MLL may not be required for the maintenance of MLL leukemia. Interestingly, in AML patients with partial tandem duplications of the MLL gene (MLL-PTD), wild-type MLL transcription is generally silenced and contributes to MLL-PTD-mediated leukemia (Whitman et al., 2005). However, the interplay between wild-type MLL and the MLL chimeras in MLL-rearranged leukemia remains elusive, given the fact that chromatin-interacting domains from the N terminus are shared between oncogenic MLL chimeras and wild-type MLL.

Here we found that wild-type MLL protein is much less abundant than the MLL chimeras in MLL leukemia cells. Therefore, we reasoned that the stabilization of the wild-type copy of the MLL protein could displace MLL chimeras from chromatin and, therefore, evade the oncogenic addiction of these cells to MLL chimeras. To test this hypothesis, we established biochemical approaches and a genome-wide small hairpin RNA (shRNA) screen to identify factors regulating MLL protein degradation. These studies identified UBE2O and the interleukin-1 (IL-1) pathway in regulating MLL stability. Disruption of the balance between wild-type MLL and MLL chimeras through chemical inhibition of the interleukin-1 receptor-associated kinases (IRAKs) impedes MLL leukemia cell proliferation both in vitro and in vivo. Together, our study reveals that targeting MLL/COMPASS degradation pathways is a promising strategy for treating the aggressive and otherwise refractory MLL leukemia, while also providing a new paradigm in the development of therapies through protein stabilization that perhaps can be applied for the treatment of other cancers resulting from translocations.

Results

UBE2O Interacts with an Internal Region of MLL and Promotes Wild-Type MLL Degradation. We first validated the specificity of the MLL antibodies using wild-type and MLL-null mouse embryonic fibroblast (MEF) cells (FIGS. 8A and 8B; data not shown). To determine the stability of the MLL chimera and the wild-type MLL, we analyzed MLL levels in multiple leukemia cell lines, and we found that the wildtype MLL protein is much less abundant than the corresponding MLL chimera when assayed by western blotting (FIGS. 1A and 8C). To determine if this observation was a consequence of lower MLL mRNA levels, we used total RNA sequencing (RNAseq) with SEM (MLL-AFF1, also called MLL-AF4) and MM6 (MLL-AF9) leukemia cells to identify MLL allele-specific SNPs that are in regions N-terminal to the breakpoints. Each SNP had similar levels of RNA expression (FIG. 1B), suggesting that wild-type MLL protein could be less stable than the MLL chimeras and that stabilization of MLL by targeting MLL degradation factors might be a potential strategy for MLL leukemia treatment.

MLL chimeras shared the same N terminus with wild-type MLL but lost internal regions C-terminal of the breakpoint (FIG. 1C). To identify proteins that associate with these missing regions, we expressed and purified the Halo-tagged portions of an internal region (MLL-Inter) and a C-terminal region (MLL-CT) in HEK293 cells. Multidimensional protein identification technology (MudPIT) analysis of the co-eluted proteins identified the ubiquitin-conjugating enzyme E2O (UBE20, an E2/E3 ubiquitin ligase) to be the most abundant protein specifically interacting with MLL-Inter, which was confirmed by co-immunoprecipitation (FIGS. 1C and 1D). In agreement, UBE2O did not interact with the most common MLL chimeras (MLL-AF9, MLLAFF1, MLL-ENL, and MLL-ELL) (FIG. 8D) (Lin et al., 2010). Further truncation of MLL-Inter demonstrated that the region spanning the MLL breakpoint region and the first PHD finger domain (1,163-1,482 aa) was required and sufficient for the MLL-UBE2O interaction (FIGS. 8E and 8F). Ectopic expression of UBE2O in HEK293 cells induced proteasome-mediated MLL degradation in a dose-dependent manner (FIG. 1E). Knockdown of UBE2O by two independent shRNAs had no effect on MLL mRNA expression (FIG. 8G) but increased wild-type MLL protein levels (but not MLL-AF9 protein levels) in FLAG-MLL-AF9 HEK293 cells (FIG. 1F). Together, these data demonstrate that UBE2O specifically interacts with the MLL internal region and induces degradation of wild-type MLL protein.

UBE2O Mediates Interleukin-1 Pathway-Induced MLL Degradation. To identify the molecular pathways involved in MLL degradation, we employed a genome-wide shRNA screen. We first generated a stable cell line with random integration of Halo-MLL that can fully reconstitute the MLL complex (FIGS. 9A and 9B). Cells stained with HaloTag ligand were sorted into Halo-MLLNeg, Halo-MLLDim, Halo-MLLMid, and Halo-MLLHigh (FIGS. 2A and 9C). The Halo-MLLDim cells were transduced with the RNAi Consortium (TRC) lentiviral libraries and selected with puromycin for 1-2 weeks before performing flow cytometry to sort cells with increased Halo-MLL protein levels (FIG. 9D). We reproducibly (four of four times) sorted a population of cells with elevated Halo-MLL signal in the shRNA library-transduced cells compared to negative control (shGFP-)transduced cells (FIG. 2B). Sequencing of the shRNA sequences from these sorted cells identified 303 gene targets (enriched in at least two different sortings).

Protein analysis through evolutionary relationships (PANTHER) pathway analysis (Mi et al., 2013) of these targets showed that the IL-1 and cytokine receptor activity terms were significantly enriched (FIG. 9E). In the shRNA screening, IL1R1, IL1RAP, and TOLLIP were enriched targets (FIG. 2C). To determine if the IL-1 pathway regulates endogenous MLL protein, we depleted TOLLIP, MYD88, and IL1RAP within the IL-1 pathway (FIG. 2C shown by stars), and we observed increased levels of endogenous MLL protein (FIGS. 2E and 2F), with no obvious effect on MLLmRNA expression (FIG. 9F).

We further stimulated HEK293C6 cells, which ectopically express IL1R1 and IL1RAP (Lu et al., 2009), with IL-1b in the presence of the protein synthesis inhibitor cycloheximide. We found that IL-1b rapidly induces MLL degradation and increases the MLL-Inter-UBE2O interaction (FIGS. 2G and 2H). Depletion of UBE2O diminishes IL-1-induced endogenous MLL protein degradation (FIG. 21), while ectopic expression of UBE2O increases MLL-Inter ubiquitination, which could be further elevated by IL-1b stimulation (FIG. 2J). Furthermore, IRAK4 could directly phosphorylate UBE2O in the in vitro kinase assay (FIG. 2K), raising the possibility that phosphorylation of UBE2O by IRAK4 could be a regulatory signal for the enhanced MLLUBE2O interaction and subsequent MLL degradation induced by IL-1b.

IRAK Inhibition Increases the Stability and Chromatin Occupancy of Wild-Type MLL. Since depleting IRAK4 protein levels can increase MLL protein levels (FIG. 3A), we asked whether IRAK4's kinase activity was required for MLL degradation. Treating cells with a small molecule inhibitor of IRAK1/4 (IRAK1/4 inhibitor I), which has been developed to inhibit the IRAK1 and IRAK4 kinase activities (Powers et al., 2006), led to increased levels of MLL protein in a time- and dose-dependent manner (FIGS. 3B and 10A). A cycloheximide chase assay also demonstrated that the IRAK1/4 inhibitor increased MLL protein stability (FIG. 10B). Consistent with the role of the IL-1 pathway and UBE2O in MLL degradation, IRAK inhibition did not affect MLL-AF9 and MLL-AFF1 protein levels (FIGS. 3C and 10C), suggesting that the IRAK activity specifically signals for the wild-type MLL degradation, but not for the MLL chimeras. Furthermore, we measured the MLL-UBE2O interaction with or without IRAK1/4 inhibitor treatment using MudPIT analysis, and we found that IRAK inhibition substantially decreased the MLL-UBE2O interaction (FIG. 3D), which was confirmed by co-immunoprecipitation (FIG. 3E).

To investigate the consequences of MLL stabilization and its association on chromatin, we performed chromatin immunoprecipitation sequencing (ChIP-seq) of MLL in HEK293 cells in the presence or absence of the IRAK1/4 inhibitor. IRAK1/4 inhibitor enhanced MLL occupancy at the well-characterized MLL target genes, HOXA, HOXC, and FOXC1, as revealed by two different MLL N320 antibodies (CST D2M7U and Bethyl NT86) (FIGS. 3F and 10D). Genome-wide analysis demonstrated that IRAK1/4 inhibition resulted in significant increases in MLL occupancy (FIGS. 3G, 3H, and 10D-10F), demonstrating that the MLL protein stabilized by IRAK inhibition can access chromatin.

Stabilization of MLL through IRAK Inhibition and UBE2O Depletion Regulates a Specific Gene Regulatory Network in MLL Leukemia. To measure the consequence of stabilizing MLL in MLL leukemia cells, we determined the effects of IRAK inhibition on cell proliferation of REH (MLL-germline leukemia) and SEM (MLL-AFF1) cells. Both of these cell lines are derived from precursor B cell ALL patient blast cells, and, therefore, they have been studied when comparing non-MLL (REH) and MLL-dependent (SEM) leukemia gene expression (Guenther et al., 2008). Treatment with 5 mM IRAK1/4 inhibitor resulted in decreased proliferation of SEM cells, but not REH cells (FIG. 4A). To avoid potential off-target effects of the IRAK1/4 inhibitor, we also used a second inhibitor named IRAK4 inhibitor compound 26, which was characterized as a more specific inhibitor of IRAK4 (Tumey et al., 2014). Treatment with 500 nM of this IRAK4 inhibitor led to an even greater inhibition of SEM cell proliferation and decreased cell viability, with no detectable effect on the REH cells (FIG. 4B).

Total RNA-seq of SEM and REH cells after 2 days of IRAK1/4 or IRAK4 inhibitor treatment was performed to characterize gene expression profile changes. We found that expression of the IKK/nuclear factor kB (NF-kB) downstream targets HOXA9 and MEIS1 (Kuo et al., 2013) was not reduced by IRAK inhibition in SEM cells, suggesting that IKK/NF-kB signaling may not be the major target of IRAK inhibition in MLL leukemia cells. However, we found that, in the presence of the IRAK1/4 inhibitor, 238 genes were downregulated and 186 genes were upregulated in both REH and SEM cells (FIG. 11A), with the gene ontology analysis of these genes consistent with a previous report in myelodysplastic syndrome (MDS) cells (FIG. 11B) (Rhyasen et al., 2013). However, this set of deregulated genes would not explain the different response to IRAK inhibition by the MLL leukemic SEM cells.

To determine the set of genes specifically deregulated in SEM cells, we compared gene expression changes in SEM and REH cells with both IRAK inhibitors (FIG. 4C). We found 227 downregulated and 119 upregulated genes in SEM cells, but not REH cells (FIGS. 4D, 4E, and 11C). Gene ontology analysis (Tripathi et al., 2015) of the SEM-specific downregulated genes showed that cell activation, cellular response to growth factor stimulus, positive regulation of cell proliferation, and integrin-mediated signaling pathway were among the top enriched terms (FIGS. 4F and 11D), while no significantly enriched terms were reported for the SEM-specific upregulated genes.

Similar to IRAK inhibition, depletion of UBE2O led to a greater defect in SEM cell proliferation compared to REH cells (FIGS. 11E and 11F). Furthermore, ectopic expression of the MLL N terminus (1-1,250 aa), which cannot interact with UBE2O but possesses chromatin-binding domains (FIG. 11G), results in a substantial reduction of SEM cell proliferation, indicating that destabilization of wild-type MLL is required for MLL leukemia cell proliferation (FIG. 11H). Our RNA-seq analysis of SEM cells after UBE2O knockdown found that 121 of the 227 genes that were downregulated by the IRAK inhibitors also were decreased by UBE2O depletion (FIG. 4G). These genes included genes related to cell activation (LGALS1, GNA15, ALDOA, and EGR1) and cellular response to growth factor stimulus (P2RY11, SREBF1, RAB13, RAB17, and RAB34) (FIG. 4G). Together, these results demonstrate that targeting MLL degradation through either IRAK inhibition or UBE2O depletion decreases cell proliferation and downregulates a specific gene regulatory network in MLL leukemia cells.

Determinants of the Increased Sensitivity of MLL Leukemia Cells to IRAK Inhibition. To further determine the effectiveness of IRAK inhibition for MLL leukemia cell growth, we performed dose-dependent studies with multiple patient-derived leukemia cell lines, including MLL leukemia and non-MLL leukemia or lymphoma cells. We found that IRAK4 inhibitor treatment preferentially impeded cell growth of MLL-rearranged AML and ALL leukemia cells (FIG. 5A), including the AML MM6 cells for which we demonstrated similar mRNA expression from the wild-type and translocated alleles (FIGS. 1A, 1B, and 5B). Interestingly, the MLL-AF6-positive ML2 leukemia cells, which have a deletion of the wild-type MLL allele, were not sensitive to the IRAK4 inhibitor (FIG. 5A). Consistent with the lower sensitivity of ML2 leukemia cells, we found that depleting wild-type MLL in MM6 cells with a shRNA targeting the MLL C terminus reduces the sensitivity of MM6 cells to IRAK inhibition (FIG. 12A). These results suggest that wild-type MLL is required for the preferential sensitivity of MLL leukemia cells to IRAK inhibition.

Comparing the differentially expressed genes in SEM and MM6 cells after IRAK inhibition, we found 59 downregulated genes and 28 upregulated genes that were shared between both cell lines (FIGS. 5C and 12B). These common downregulated genes contained genes related to cell activation and cellular response to growth factor stimulus (FIG. 5D). Among these genes, LGALS1 and LMO2 previously were identified to be highly expressed in MLL leukemia (Armstrong et al., 2002). Depletion of LGALS1 or LMO2 also reduced MM6 cell proliferation (FIGS. 5E and 5F), indicating that IRAK inhibition could prevent MLL leukemia cell proliferation, at least partially, through downregulation of LGALS1 and LMO2 expression.

Using the University of California, Santa Cruz (UCSC) cancer genome database (children's oncology group [COG], POG 9906), we found that IL-1 pathway components MYD88, IRAK1, and IRAK4 are expressed at a higher level in MLL-rearranged ALL patients than non-MLL ALL patients (FIG. 12C). Furthermore, enhanced expression of Irak1 and Irak4was found in primary and secondary leukemia inanMLL-AF9mousemodel (FIG. 12D) (Liu et al., 2014). Together, these findings indicate a dependence of MLL leukemia on IL-1 signaling, and they suggest that targeting wild-type MLL degradation by IRAK inhibition is a potential therapeutic approach for the MLL translocation-based leukemia.

IRAK Inhibition Displaces the MLL Chimera and Subunits of SEC at a Subset of Target Genes. As described above, IRAK inhibition significantly increases MLL chromatin occupancy and preferentially impedes MLL leukemia cell proliferation. We sought to profile the chromatin occupancy of the MLL chimera to determine the mechanistic basis of IRAK inhibition abrogating the oncogenic potential of MLL chimeras. However, our MLL antibodies recognize the MLL N-terminal epitopes shared by the wild-type MLL and the MLL chimeras. Therefore, we employed a strategy based on comparing co-occupancy of the MLL fusion partner AFF1 (AFF1 C-terminal) and the SEC subunits that are recruited by the MLL chimeras (Lin et al., 2010; Yokoyama et al., 2010). We tested this strategy in FLAG-MLL-AFF1 HEK293 cells, and we observed increased occupancy of MLL-NT at the sites of normal MLL occupancy in HEK293 cells (FIGS. 13A and 13B). The increase of MLLAFF1 chimera occupancy also was detected by the co-enrichment of AFF1 (AFF1-CT antibody), which is generally not enriched at most of these genes in HEK293 cells (FIGS. 13A and 13B). Furthermore, SEC subunit recruitment to these MLL-AFF1-binding sites was demonstrated by AFF4 ChIP-seq (FIGS. 13A and 13B). MLL-AFF1 (AFF1-CT) and AFF4 ChIP-seq in SEM cells demonstrated that MLL-AFF1 and AFF4 occupancies were both reduced in the promoter-proximal regions of LGALS1, GNA15, and LMO2 genes after IRAK inhibitor treatment (FIG. 6A), consistent with the downregulation of these genes by IRAK inhibition. Genome-wide analysis further revealed that MLL-AFF1 occupancy was significantly decreased (more than 25%) around the promoter-proximal regions of 1,311 genes (FIGS. 6B and 6C), while AFF4 occupancy was decreased at these regions as well (FIGS. 6D and 6E), demonstrating that IRAK inhibition displaces MLL chimeras and SEC from these chromatin regions.

To further determine if LGALS1, LMO2, and GNA15 are direct target genes of MLL chimeras and SEC, we performed AFF4 knockdown in SEM cells (FIG. 13C), and we found that AFF4 depletion resulted in decreased mRNA expression of LGALS1, LMO2, and GNA15 genes as well (FIGS. 6F and 13D). These results demonstrate that IRAK inhibition displaces MLL chimeras and its oncogenic cofactor SEC at a subset of MLL chimera target genes.

IRAK Inhibitors Substantially Delay the Progression and Improve the Survival of Murine MLL-AF9 Leukemia In Vivo. We further assessed the effects of the IRAK inhibitors in vivo using the murine MLL-AF9 leukemia transplantation model (FIG. 7A) (Volk et al., 2014). Primary MLL-AF9 leukemia cells were sensitive to IRAK inhibition based on the decreased colony formation and cell proliferation in vitro (FIGS. 14A and 14B). To measure the potential of IRAK inhibitors as a first-line treatment, we initiated the injection of the animals with IRAK inhibitors on day 19 after transplantation, just before they succumb to leukemia. Intraperitoneal injection with IRAK1/4 inhibitor (8 mg/kg), IRAK4 inhibitor (75 mg/kg) (Tumey et al., 2014), or vehicle was performed every other day for 10 days. At sacrifice, the leukemia was confirmed by enlarged spleen, liver weights, elevated white blood cell counts (FIGS. 14C-14E), and histological analysis. Both IRAK inhibitors significantly extended survival of the recipients beyond the 27 days when all of the vehicle-treated mice succumbed to the disease, and they extended the life of the AML mice to more than 55 days, with one mouse from each IRAK inhibitor-treated group still alive at day 55 (FIG. 7B).

We also treated cohorts of animals 10 days after transplantation (FIG. 7C). Strikingly, eight of ten mice from the IRAK1/4 inhibitor-treated group and four of nine mice from the IRAK4 inhibitor group still did not develop MLL-AF9 leukemia as of day 55, while all of the vehicle-treated mice succumbed to the disease by 31 days after transplantation (FIG. 7C). IRAK inhibitor treatment of mice led to a substantial decrease of leukemic blasts in the peripheral blood, as seen by white blood cell counting (FIG. 14E) or visually in blood smears from the MLL-AF9 leukemic mice at the endpoint (FIG. 7D). Wright-Giemsa staining also revealed that the blasts from IRAK inhibitor-treated MLL-AF9 leukemic mice were partially differentiated (FIG. 7D). Together, these data suggest that pharmacologic inhibition of IRAK can delay the progression and improves survival of the aggressive MLL-AF9 leukemia in vivo.

Discussion

Murine MLL chimera knock-in mice develop leukemia with a long latency, which indicates that multiple cooperating events and/or signaling pathways are required in the pathogenic process (Li and Ernst, 2014). Despite the complexity of these diseases and the remaining challenges for effective treatments, biochemical and developmental insights have led to the proposal of several therapeutic strategies, including the use of small molecules that block the Menin-MLL interaction (Borkin et al., 2015) or disrupt the chromatin binding of the bromodomain-containing protein 4 (BRD4) (Dawson et al., 2011). Inhibitors of the methyltransferase activity of DOT1L also have been tested in phase 1 clinical trials, and they are being explored for use in combination with other therapies (Singer, 2015). Recent studies (Fong et al., 2015; Rathert et al., 2015) also reported recurring development of resistance to BRD4 inhibitors.

Here, we provide a unique mechanism for the treatment of MLL translocation-based leukemia via the stabilization of the wild-type copy of MLL (FIG. 7E). Through our biochemical and molecular screens, we demonstrated that the IL-1 pathway initiates the specific degradation of wild-type IRAK1/4 and UBE20, while MLL chimeras escape UBE20-mediated degradation for lack of the MLL-UBE20-interacting region (FIG. 7E). The higher expression of IL-1 pathway components in MLL-translocated ALL leukemia patient cells and the increased Irak1 and Irak4 expression in mouse models correlate with the low abundance of wild-type MLL protein in MLL leukemia cells (FIGS. 1A, 1B, and 8C). The IRAK1/4 inhibitor recently has been shown to sensitize a subset of MDS and T-ALL cells that exhibit high expression of IRAK1 to BCL2 inhibitor treatment, although IRAK1/4 inhibitor alone does not substantially impair these cells (Li et al., 2015; Rhyasen et al., 2013). We found profound effects of IRAK inhibition alone for MLL leukemia both in vitro and in vivo. Mechanistically, we found that targeting wild-type MLL degradation through IRAK inhibition or UBE2O depletion impedes MLL leukemia cell proliferation and downregulates a common subset of MLL chimera target genes. These genes (FIG. 4F) are likely to contribute to the observed antiproliferative effects in MLL leukemia cells. Indeed, knockdown of LGALS1 or LMO2 leads to decreased MLL leukemia cell proliferation (FIGS. 5E and 5F), indicating that downregulation of these genes contributes to the cell growth inhibition observed after IRAK inhibition or UBE2O knockdown. The downregulation of these genes could be explained by the decreased occupancy of the MLL chimeras and the associated SEC, a key cofactor for MLL leukemia (Smith et al., 2011). Together, these findings explain the enhanced effects of IRAK inhibition on MLL chimera-driven leukemia compared to other non-MLL-rearranged leukemia, and they suggest that stabilization of wildtype MLL could be a potential therapeutic strategy for MLL leukemia treatment (FIG. 7E).

Although a requirement for wild-type MLL in leukemogenesis has been suggested by the decreased growth of MLL leukemia cells in the presence of a small molecule that disrupts the WDRS-MLL SET domain interaction (Cao et al., 2014), a recent study demonstrated that deletion of the whole SET domain of wild-type MLL has no effect on MLL leukemogenesis, suggesting that at least the HMT activity of MLL is dispensable for MLL leukemogenesis (Mishra et al., 2014). Furthermore, ChIP-seq analysis of MLL chimera occupancy in ML2 cells, in which the entire wild-type locus is lost, demonstrated that MLL chimeras can access chromatin to mediate their oncogenic functions in the absence of wild-type MLL (Okuda et al., 2014; Wang et al., 2011). MLL fusion proteins require an open chromatin status for chromatin occupancy due to their impaired chromatin-binding capability, likely due to their missing key chromatin-binding modules, such as PHD fingers and a bromodomain (Milne et al., 2010). These data suggest that, rather than being required for the oncogenic function of MLL chimeras, wild-type MLL has the potential to outcompete the chimeras through additional chromatin-binding modules. Therefore, lessening the imbalance between wild-type MLL and the more abundant oncogenic MLL chimeras could deregulate MLL chimera target gene expression and impair MLL leukemia cell proliferation.

In addition to IL-1 receptors, Toll-like receptors can activate the IRAKs, suggesting that these pathways also may have the potential to regulate MLL stability and contribute to MLL leukemia. In this study, we observed a few-fold increase of MLL occupancy after IRAK inhibition, with the MLL chimera and SEC occupancy being reduced only at a subset of genes generally associated with weak MLL chimera and SEC occupancy. Therefore, searching for additional pathways involved in regulating MLL stability could be very helpful for MLL leukemia treatment. In conclusion, our study suggests that altering the balance between wild-type MLL and MLL oncogenic fusion proteins by modulating signaling pathways is a promising approach for treating the aggressive and refractory MLL-rearranged leukemia. Furthermore, in addition to stabilization of MLL as a paradigm in the development of therapies for aggressive MLL leukemia, perhaps other cancers caused by translocations can be treated via developing similar stabilization strategies.

Experimental Models and Subject Details

Cell Lines. HEK293 cells, Flag-MLL-AFF1 and Flag-MLL-AF9 stable cell lines (Lin et al., 2010) were cultured in Dulbecco's Modified Eagle Medium (DMEM) supplemented with 10% fetal bovine serum (FBS, catalog No. F6178, Sigma). The 293C6 stable cell line with the overexpression of IL1R1 and IL1RAP in HEK293 cells was a gift from George Stark's Lab (Cleveland Clinic) and maintained in DMEM medium with5% FBS. MONO-MAC-6 (MM6, ACC-252), RL (CRL-2261), U-937 (CRL-1593.2), RS4; 11 (CRL-1873), SU-DHL-5 (CRL-2958), SU-DHL-6 (CRL-2959), MOLM13 (ACC-554), OCI-LY1 (ACC-722), THP-1 (TIB-202), ML-2 (ACC-15), NB-4 (ACC-207) and REH (ACC-22) leukemia cells were maintained in RPMI-1640 medium supplemented with 10% FBS. MV4-11 (CRL-9591) and SEM (ACC-546) leukemia cells were maintained in Iscove's Modified Dulbecco's Medium (IMDM) with 10% FBS. The Mll wildtype Mll+/+ and knockout Mll−/− mouse embryonic fibroblasts (MEF) cell lines were provided by Dr. Jay Hess (University of Michigan Medical School) and cultured in DMEM with 10% FBS.

Expression Plasmids and shRNAs. Mammalian COMPASS expression constructs fused with an N-terminal HaloTag (pFENHK-Halo-MLL, pFENHK-Halo-MLL2 (KMT2B), pFENHK-Halo-SETD1A and pFENHK-Halo-MLL4 (KMT2D) plasmids) were obtained from Promega. Halo-MLL truncates were amplified by PCR with pFENHK-Halo-MLL plasmid and subcloned into the pFENHK plasmid. pCDH-CMV-MLL(1-1250)-EF1-GFP was constructed by insertion of MLL cDNA (1-1250aa) into pCDH-CMV-MCS-EF1-GreenPuro vector (SBI, Cat#: D513B-1). Myc-tagged UBE2O full-length plasmid was provided by El Bachir Affar (University of Montreal). pcDNA5-Flag-UBE2O truncate (552-1292aa) was cloned from UBE2O cDNA (CCSB Human ORFeome UBE2O Clone Without Stop Codon Accession: BC051868) (Dharmacon Inc., Clone ID: 11793) into the pcDNA5-Flag plasmid. shRNAs for human TOLLIP (TRCN0000063693 and TRCN0000356024), IL1RAP (TRCN0000058540 and TRCN0000372626), IL1R1 (TRCN0000059260 and TRCN0000360115, MYD88 (TRCN0000008025 and TRCN0000011223) were used to knockdown the IL-1 pathway components. IRAK4 was depleted with the shRNAs: TRCN0000002064 and TRCN0000435677. LGALS1 (TRCN0000057423 and TRCN0000057424) and LMO2 (TRCN0000017128 and TRCN0000017130) were depleted with shRNAs in MM6 cells. UBE2O was depleted with shRNAs: TRCN0000004587 and TRCN0000272907. Wild-type MLL was depleted with a shRNA targeting a C-terminal region of MLL (GCCAAGCACTGTCGAAATTAC).

Murine MLL-AF9 Leukemia Model. To generate the MLL-AF9 leukemic mice, bone marrow transplantation with MigR1-MLL-AF9 was performed as previously described (Volk et al., 2014). C-Kit+ HSPCs isolated from the bone marrow of female C57BL/6 mice (8-10 weeks old) were spinoculated with MigR1-MLL-AF9 and selected with G418 for one week. Primary recipient female C57BL/6 mice (Age range from 8-10 weeks) were irradiated (900 cGy) and transplanted by tail vein intravenous injection with 1×106 MLL-AF9 transduced cells along with 2×105 wild-type support cells. The mice were monitored for signs of acute leukemia for 2-3 months and euthanized when leukemia was evident (weight loss below 16.75 g, reduced mobility, malaise, palpable spleen, and hunched back). Spleens were isolated from leukemic mice and the homogenate was grown in suspension culture (RPMI-1640 supplemented with penicillin/streptomycin, 10% FBS, 100 ng/mL SCF, 50 ng/mL IL6, and 20 ng/mL IL3) for one week. 1×104 of the resulting leukemia cells were transplanted into sub-lethally irradiated (450 cGy) female C57BL/6 mice (8-10 weeks) via tail vein injection. Animal studies were approved by the Loyola University Chicago and Northwestern University Institutional Animal Care and Use Committees.

Method Details

HaloTag Purification and MudPIT Analysis. Plasmids encoding Halo-tagged proteins were transiently transfected into HEK293 cells. 2 days later, HEK293 cells were harvested and lysed with mammalian lysis buffer (Promega). For IRAK1/4 inhibitor treatment, 10 mM IRAK1/4 inhibitor was added 24 hr before harvest. Halo-tagged proteins were purified with HaloLink resin in the presence of Benzonase (Sigma) and eluted with TEV protease. The eluates were precipitated with TCA. After washing with acetone, the protein mixtures were digested with endoproteinase Lys-C and trypsin (Roche) and analyzed by MudPIT as previously described (Liang et al., 2015a). Original mass spectrometry data can be accessed from the Stowers Original Data Repository at http://www.stowers.org/research/publications/libpb-1090.

Generation of Halo-MLLDim HEK293 Cells. To generate Halo-tagged MLLDim cells, HEK293 cells were transfected with pFENHK-MLL plasmid with Polyethylenimine. 2 days later, the transfected cells were selected with 400 ng/ml G418 for 3 weeks and stained with HaloTag R110Direct ligand (Promega). Cells were then sorted according to the Halo-tag signals with a MoFlo sorter (Beckman Coulter) as MLLNegative, MLLDim, MLLMid, and MLLHigh. The sorted cells were grown in DMEM with 10% FBS and selected with 400 ng/ml G418. 2 weeks later, the cells were resorted according to HaloTag signals. The MLLDim were further sorted two more times.

IRAK4 Kinase Assay. HEK293 cells were transient transfected with either vector or pcDNA5-Flag-UBE2O (552-1292aa). 2 days later, Flag-UBE2O was purified from these HEK293 cells with ANTI-FLAG M2 affinity gel and eluted with FLAG peptides. Eluates from Flag-UBE2O and vector control purifications were heat-inactivated and used as substrates in radioactive kinase assays. The phosphorylation of UBE2O were measured in the presence of 100 ng His-tagged human IRAK4 (Sino Biological), 2 mCi g-32P ATP in 20 ml kinase buffer (20 mM HEPES [pH 7.9], 8 mM MgCl2, 0.5% glycerol, 0.1% Triton X-100, 1 mM DTT). After incubation at 37_C for 6 hr, reactions were stopped by adding 5 3 SDS loading buffer, and the phosphorylated proteins were visualized by SDS-PAGE and autoradiography.

Genome-wide shRNA Library Screening. A pooled TRC lentiviral library (Mi et al., 2013), which contains TRC1 81041 shRNAs and TRC1.5 17563 shRNAs, was used for lentiviral packaging with packaging vectors pD8.9 and pCMV-VSV-G. Lentiviral particles were harvested after 4 days and used to transduce MLLDim HEK293 cells. The lentiviral particles were titered to transduce 30%-50% of the MLLDim cells. The infected cells were further selected with 2.0 ng/ml puromycin for 1-2 weeks and stained with HaloTag R110 direct ligand (Promega). Flow cytometry sorting with MoFlo was performed to sort for cells with increased Halo-MLL protein levels (Based on the HaloTag signal intensity).

To deconvolve the shRNA composition, the sorted cells were lysed with DirectPCR Lysis Reagent (Viagen Biotech) and shRNA sequences were PCR amplified as a single mixture using vector-backbone directed universal primers from extracted genomic DNA. 4 independent cell sortings were performed representing 4 different biological replicates. The first 3 cell sortings were also amplified with a different set of primers to represent technical replicates. PCR products were cleaned up with QIAGEN's PCR purification kit and digested with Xho I. The 103 bp fragments that contain half-hairpin sequences of the shRNAs were gel purified and ligated with barcoded linkers. Illumina adapters were added to PCR products to generate libraries for next-generation sequencing.

The sequence reads were aligned to the TRC reference shRNA library using Bowtie (Langmead et al., 2009) and allowing for 2 mismatches (bowtie-p 2-f-v 2-best-strata-m 1). Only uniquely aligned reads were counted and ambiguous reads were excluded. The abundance of each shRNA in the sorted cells was based on the number of aligned reads. A shRNA was a "hit" in a sort if its abundance was ranked in the top 2× sorted cell number (e.g., if 400 cells were sorted, a shRNA needed to be among the 800 most abundant shRNAs). Since each gene in the shRNA library has multiple independent shRNAs, different shRNAs targeting the same gene were considered in calculating the overall enrichment of a gene. Enriched genes had shRNA hits in at least 3 of the 7 sorts to ensure that a hit occurred in at least two biological replicates.

Chromatin Immunoprecipitation Sequencing. 53107 cells were used per ChIP assay according to a published protocol (Liang et al., 2015b). Briefly, cells were crosslinked with 1% paraformaldehyde for 15 min and were quenched with glycine for 5 min at room temperature. Fixed chromatin was sonicated with a Covaris Focused-ultrasonicator and immune-precipitated with the indicated antibody. Libraries were prepared with the highthrough-put Library preparation kit standard PCR amp module (KAPA Biosystems) for next-generation sequencing. ChIP-seq reads were aligned to the mouse (UCSC mm9) or human genome (UCSC hg19). Alignments were processed with Bowtie version 1.1.2, allowing only uniquely mapping reads with up to two mismatches within the 50 bp read. The resulting reads were extended to 150 bases toward the interior of the sequenced fragment and normalized to total reads aligned (reads per million, rpm). For MLL ChIP-seq in 293 cells in FIGS. 3G, 3H, 10E, and 10F, peak detection was performed with MACS (model-based analysis of ChIP-Seq) version 1.4.2 (Zhang et al., 2008) using default parameters. D2M7U and NT86 peaks that overlapped between the IRAK1/4 inhibitor treated and non-treated cells were combined and collapsed to give 6,250 MLL-occupied regions. The average coverage (calculated using rpm tracks described above) across the entire region is shown in the boxplots where p values were calculated with the Wilcoxon signed-rank test. Heatmaps depict log 2 fold change of coverage profiles in a 6 kb window around the merged peak center in 25 bp binned averages and sorted by total coverage in this window.

For FIGS. 6B-6E, heatmaps and metagene plots of the genes with decreased AFF1-CT read coverage around the TSS (±3 kb) after both IRAK inhibitor treatment were plotted with ngs.plot 2.47 and ranked by read intensity. The AFF4 read coverage at these sites was plotted with the same order. In FIGS. 13A and 13B, all genes with MLL occupancy (12,300 genes) were plotted in the heatmaps ranked by read intensity. The AFF1-CT and AFF4 signals were plotted with the same order. Metagene analysis of MLL, AFF1-CT and AFF4 were calculated based on all of the genes.

Total RNA Sequencing. After IRAK inhibitors treatment for 2 days, REH, SEM and MM6 cells were collected and lysed with Trizol reagent. Total RNA was extracted from Trizol according to the manufacturer's instructions. The RNA was treated with DNase I (NEB) and cleaned with the QIAGEN RNeasy mini kit. 500 ng RNA was used for library preparation with TruSeq Stranded Total RNA with Ribo-Zero Gold kit (Illumina, RS-123-2201). The sequenced reads were aligned to the human genome (UCSC hgl9) with TopHat 2.1.0 using gene annotations from Ensembl 72. Differential gene expression was performed with EdgeR (Empirical analysis of digital gene expression data in R) version 3.08 (Robinson et al., 2010). Adjusted p values were computed using the Benjamini-Hochburg method. Protein coding genes, long non-coding RNA and pseudogenes with adjusted p values less than 0.01 were used for the downstream analysis with Metascape. P values for Venn diagrams were performed with the hypergeometric test.

In vitro MLL-AF9 Assays. Primary murine MLL-AF9 cells were seeded in M3434 methylcellulose (StemCell Technologies, Inc.) at 1×103/10 mm per well with indicated doses of IRAK1/4, IRAK4 inhibitor, or vehicle and incubated at 37 degrees. Colonies were enumerated after 7 days, and defined clusters with >100 cells were counted as colonies. For the liquid culture assay, primary MLL-AF9 cells were cultured in media (RPMI-1640 supplemented with penicillin/streptomycin, 10% FBS, 100 ng/mL SCF, 50 ng/mL IL6, and 20 ng/mL IL3), and stained with trypan blue. The viable cells were counted by a Vi-CELL XR cell counter (Beckman Coulter).

Animal Treatment. 10 or 19 days after transplantation, mice were randomized and treated with 8 mg/kg IRAK1/4 inhibitor or 75 mg/kg IRAK4 inhibitor, or vehicle (10% DMSO and 90% PBS) every other day for 10 days. Mice were monitored for leukemia development and leukemia was verified after the mice were sacrificed upon signs of illness (weight loss below 16.75 g, partial paralysis, malaise, palpable spleen, and hunched back).

Quantification and Statistical Analyses. Data are presented as Mean±SD. The sample sizes (n) indicate the number of replicates or number of mice in each experiment and are provided in the corresponding figure legends. The peak or gene size (N) in the heatmaps indicates the number of peaks or genes included. For FIGS. 5E, 5F, 8G, 9F, and S14, One-Way ANOVA tests were performed with Prism 6 (GraphPad Software, La Jolla, Calif.) to determine the statistical significance. P value <0.005 () was considered as highly significantly different, p value <0.05 was considered as significantly different, n.s, not significantly different, p R 0.05. For FIGS. 3H, 6C, 6E, 10F, and 12C, the statistical significance was determined by the Wilcoxon signed-rank test using R 3.2.1 package with the p values provided in each figure. For FIGS. 7B and 7C, the Kaplan-Meier survival curves were plotted with GraphPad Prism 6 and the p values were calculated using the log rank test. P values for Venn diagrams in FIG. 4**C were calculated with the hypergeometric test in R 3.2.1. For the western blot results, representative figures of at least three biological replicates were shown. After background subtraction, the densitometric analysis of MLL bands were performed with ImageJ and normalized to the loading control Tubulin. Fold changes of MLL N320 protein were calculated based on the negative controls as indicated in the figure legends.

Data and Software Availability. The accession number for the raw and processed NGS data reported in this paper is GEO: GSE89485. The accession numbers for the proteomics data reported in this paper are MSV: 000080298 and PXD: 005233.

REFERENCES

Armstrong, S. A., Staunton, J. E., Silverman, L. B., Pieters, R., den Boer, M. L., Minden, M. D., Sallan, S. E., Lander, E. S., Golub, T. R., and Korsmeyer, S. J. (2002). MLL translocations specify a distinct gene expression profile that distinguishes a unique leukemia. Nat. Genet. 30, 41-47.

Borkin, D., He, S., Miao, H., Kempinska, K., Pollock, J., Chase, J., Purohit, T., Malik, B., Zhao, T., Wang, J., et al. (2015). Pharmacologic inhibition of the Menin-MLL interaction blocks progression of MLL leukemia in vivo. Cancer Cell 27, 589-602.

Cao, F., Townsend, E. C., Karatas, H., Xu, J., Li, L., Lee, S., Liu, L., Chen, Y., Ouillette, P., Zhu, J., et al. (2014). Targeting MLL1 H3K4 methyltransferase activity in mixed-lineage leukemia. Mol. Cell 53, 247-261.

Dawson, M. A., Prinjha, R. K., Dittmann, A., Giotopoulos, G., Bantscheff, M., Chan, W. I., Robson, S. C., Chung, C. W., Hopf, C., Savitski, M. M., et al. (2011). Inhibition of BET recruitment to chromatin as an effective treatment for MLL-fusion leukaemia. Nature 478, 529-533.

Fong, C. Y., Gilan, O., Lam, E. Y., Rubin, A. F., Ftouni, S., Tyler, D., Stanley, K., Sinha, D., Yeh, P., Morison, J., et al. (2015). BET inhibitor resistance emerges from leukaemia stem cells. Nature 525, 538-542.

Gan, T., Jude, C. D., Zaffuto, K., and Ernst, P. (2010). Developmentally induced Mll1 loss reveals defects in postnatal haematopoiesis. Leukemia 24, 1732-1741.

Guenther, M. G., Lawton, L. N., Rozovskaia, T., Frampton, G. M., Levine, S. S., Volkert, T. L., Croce, C. M., Nakamura, T., Canaani, E., and Young, R. A. (2008). Aberrant chromatin at genes encoding stem cell regulators in human mixed-lineage leukemia. Genes Dev. 22, 3403-3408.

Hanson, R. D., Hess, J. L., Yu, B. D., Ernst, P., van Lohuizen, M., Berns, A., van der Lugt, N. M., Shashikant, C. S., Ruddle, F. H., Seto, M., and Korsmeyer, S. J. (1999). Mammalian Trithorax and polycomb-group homologues are antagonistic regulators of homeotic development. Proc. Natl. Acad. Sci. USA 96, 14372-14377.

Jones, W. D., Dafou, D., McEntagart, M., Woollard, W. J., Elmslie, F. V., Holder-Espinasse, M., Irving, M., Saggar, A. K., Smithson, S., Trembath, R. C., et al. (2012). De novo mutations in MLL cause Wiedemann-Steiner syndrome. Am. J. Hum. Genet. 91, 358-364.

Jude, C. D., Climer, L., Xu, D., Artinger, E., Fisher, J. K., and Ernst, P. (2007). Unique and independent roles for MLL in adult hematopoietic stem cells and progenitors. Cell Stem Cell 1, 324-337.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol. 14, R36.

Kuo, H. P., Wang, Z., Lee, D. F., Iwasaki, M., Duque-Afonso, J., Wong, S. H., Lin, C. H., Figueroa, M. E., Su, J., Lemischka, I R., and Cleary, M. L. (2013). Epigenetic roles of MLL oncoproteins are dependent on NF-kB. Cancer Cell 24, 423-437.

Langmead, B., Trapnell, C., Pop, M., and Salzberg, S. L. (2009). Ultrafast and memory-efficient alignment of short DNA sequences to the human genome. Genome Biol. 10, R25.

Li, B. E., and Ernst, P. (2014). Two decades of leukemia oncoprotein epistasis: the MLL1 paradigm for epigenetic deregulation in leukemia. Exp. Hematol. 42, 995-1012.

Li, Z., Younger, K., Gartenhaus, R., Joseph, A. M., Hu, F., Baer, M. R., Brown, P., and Davila, E. (2015). Inhibition of IRAK1/4 sensitizes T cell acute lymphoblastic leukemia to chemotherapies. J. Clin. Invest. 125, 1081-1097.

Liang, K., Gao, X., Gilmore, J. M., Florens, L., Washburn, M. P., Smith, E., and Shilatifard, A. (2015a). Characterization of human cyclin-dependent kinase 12 (CDK12) and CDK13 complexes in C-terminal domain phosphorylation, gene transcription, and RNA processing. Mol. Cell. Biol. 35, 928-938.

Liang, K., Woodfin, A. R., Slaughter, B. D., Unruh, J. R., Box, A. C., Rickels, R. A., Gao, X., Haug, J. S., Jaspersen, S. L., and Shilatifard, A. (2015b). Mitotic transcriptional activation: clearance of actively engaged Pol II via transcriptional elongation control in mitosis. Mol. Cell 60, 435-445.

Lin, C., Smith, E. R., Takahashi, H., Lai, K. C., Martin-Brown, S., Florens, L., Washburn, M. P., Conaway, J. W., Conaway, R. C., and Shilatifard, A. (2010). AFF4, a component of the ELL/P-TEFb elongation complex and a shared subunit of MLL chimeras, can link transcription elongation to leukemia. Mol. Cell 37, 429-437.

Liu, Y., Cheng, H., Gao, S., Lu, X., He, F., Hu, L., Hou, D., Zou, Z., Li, Y., Zhang, H., et al. (2014). Reprogramming of MLL-AF9 leukemia cells into pluripotent stem cells. Leukemia 28, 1071-1080.

Lu, T., Jackson, M. W., Singhi, A. D., Kandel, E. S., Yang, M., Zhang, Y., Gudkov, A. V., and Stark, G. R. (2009). Validation-based insertional mutagenesis identifies lysine demethylase FBXL11 as a negative regulator of NFkappaB. Proc. Natl. Acad. Sci. USA 106, 16339-16344.

Mashtalir, N., Daou, S., Barbour, H., Sen, N. N., Gagnon, J., Hammond-Martel, I., Dar, H. H., Therrien, M., and Affar, B. (2014). Autodeubiquitination protects the tumor suppressor BAP1 from cytoplasmic sequestration mediated by the atypical ubiquitin ligase UBE2O. Mol. Cell 54, 392-406.

McMahon, K. A., Hiew, S. Y., Hadjur, S., Veiga-Fernandes, H., Menzel, U., Price, A. J., Kioussis, D., Williams, O., and Brady, H. J. (2007). Mll has a critical role in fetal and adult hematopoietic stem cell self-renewal. Cell Stem Cell 1, 338-345.

Meyer, C., Hofmann, J., Burmeister, T., Groger, D., Park, T. S., Emerenciano, M., Pombo de Oliveira, M., Renneville, A., Villarese, P., Macintyre, E., et al. (2013). The MLL recombinome of acute leukemias in 2013. Leukemia 27, 2165-2176.

Mi, H., Muruganujan, A., Casagrande, J. T., and Thomas, P. D. (2013). Largescale gene function analysis with the PANTHER classification system. Nat. Protoc. 8, 1551-1566.

Miller, T., Krogan, N. J., Dover, J., Erdjument-Bromage, H., Tempst, P., Johnston, M., Greenblatt, J. F., and Shilatifard, A. (2001). COMPASS: a complex of proteins associated with a trithorax-related SET domain protein. Proc. Natl. Acad. Sci. USA 98, 12902-12907.

Milne, T. A., Kim, J., Wang, G. G., Stadler, S. C., Basrur, V., Whitcomb, S. J., Wang, Z., Ruthenburg, A. J., Elenitoba-Johnson, K. S., Roeder, R. G., and Allis, C. D. (2010). Multiple interactions recruit MLL1 and MLL1 fusion proteins to the HOXA9 locus in leukemogenesis. Mol. Cell 38, 853-863.

Mishra, B. P., Zaffuto, K. M., Artinger, E. L., Org, T., Mikkola, H. K., Cheng, C., Djabali, M., and Ernst, P. (2014). The histone methyltransferase activity of MLL1 is dispensable for hematopoiesis and leukemogenesis. Cell Rep. 7, 1239-1247. Mohan, M., Herz, H. M., Takahashi, Y. H., Lin, C., Lai, K. C., Zhang, Y., Washburn, M. P., Florens, L., and Shilatifard, A. (2010a). Linking H3K79 trimethylation to Wnt signaling through a novel Dotl-containing complex (DotCom). Genes Dev. 24, 574-589.

Mohan, M., Lin, C., Guest, E., and Shilatifard, A. (2010b). Licensed to elongate: a molecular mechanism for MLL-based leukaemogenesis. Nat. Rev. Cancer 10, 721-728.

Nguyen, A. T., Taranova, O., He, J., and Zhang, Y. (2011). DOT1L, the H3K79 methyltransferase, is required for MLL-AF9-mediated leukemogenesis. Blood 117, 6912-6922.

Okuda, H., Kawaguchi, M., Kanai, A., Matsui, H., Kawamura, T., Inaba, T., Kitabayashi, I., and Yokoyama, A. (2014). MLL fusion proteins link transcriptional coactivators to previously active CpG-rich promoters. Nucleic Acids Res. 42, 4241-4256.

Pigneux, A., Labopin, M., Maertens, J., Cordonnier, C., Volin, L., Socie', G., Blaise, D., Craddock, C., Milpied, N., Bacher, U., et al.; Acute Leukemia Working Party EBMT (2015). Outcome of allogeneic hematopoietic stem-cell transplantation for adult patients with AML and 11q23/MLL rearrangement (MLL-r AML). Leukemia 29, 2375-2381.

Powers, J. P., Li, S., Jaen, J. C., Liu, J., Walker, N. P., Wang, Z., and Wesche, H. (2006). Discovery and initial SAR of inhibitors of interleukin-1 receptor-associated kinase-4. Bioorg. Med. Chem. Lett. 16, 2842-2845. Rathert, P., Roth, M., Neumann, T., Muerdter, F., Roe, J. S., Muhar, M., Deswal, S., Cemy-Reiterer, S., Peter, B., Jude, J., et al. (2015). Transcriptional plasticity promotes primary and acquired resistance to BET inhibition. Nature 525, 543-547.

Rhyasen, G. W., Bolanos, L., Fang, J., Jerez, A., Wunderlich, M., Rigolino, C., Mathews, L., Ferrer, M., Southall, N., Guha, R., et al. (2013). Targeting IRAK1 as a therapeutic approach for myelodysplastic syndrome. Cancer Cell 24, 90-104.

Robinson, M. D., McCarthy, D. J., and Smyth, G. K. (2010). edgeR: a Bioconductor package for differential expression analysis of digital gene expression data. Bioinformatics 26, 139-140.

Shen, L., Shao, N., Liu, X., and Nestler, E. (2014). ngs.plot: Quick mining and visualization of next-generation sequencing data by integrating genomic databases. BMC Genomics 15, 284.

Shilatifard, A. (2012). The COMPASS family of histone H3K4 methylases: mechanisms of regulation in development and disease pathogenesis. Annu. Rev. Biochem. 81, 65-95.

Singer, A. (2015). Epizyme announces second quarter 2015 financial results and provides corporate update. https://www.sec.gov/Archives/edgar/data/1571498/000119312515279839/d23584dex991. htm.

Smith, E., Lin, C., and Shilatifard, A. (2011). The super elongation complex (SEC) and MLL in development and disease. Genes Dev. 25, 661-672.

Thiel, A. T., Blessington, P., Zou, T., Feather, D., Wu, X., Yan, J., Zhang, H., Liu, Z., Ernst, P., Koretzky, G. A., and Hua, X. (2010). MLL-AF9-induced leukemogenesis requires coexpression of the wild-type Mll allele. Cancer Cell 17, 148-159.

Tomizawa, D., Koh, K., Sato, T., Kinukawa, N., Morimoto, A., Isoyama, K., Kosaka, Y., Oda, T., Oda, M., Hayashi, Y., et al. (2007). Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group. Leukemia 21, 2258-2263.

Tripathi, S., Pohl, M. O., Zhou, Y., Rodriguez-Frandsen, A., Wang, G., Stein, D. A., Moulton, H. M., DeJesus, P., Che, J., Mulder, L. C., et al. (2015). Metaand orthogonal integration of influenza "OMICs" data defines a role for UBR4 in virus budding. Cell Host Microbe 18, 723-735.

Tumey, L. N., Boschelli, D. H., Bhagirath, N., Shim, J., Murphy, E. A., Goodwin, D., Bennett, E. M., Wang, M., Lin, L. L., Press, B., et al. (2014). Identification and optimization of indolo[2,3-c]quinoline inhibitors of IRAK4. Bioorg. Med. Chem. Lett. 24, 2066-2072.

Volk, A., Li, J., Xin, J., You, D., Zhang, J., Liu, X., Xiao, Y., Breslin, P., Li, Z., Wei, W., et al. (2014). Co-inhibition of NF-kB and JNK is synergistic in TNF-expressing human AML. J. Exp. Med. 211, 1093-1108.

Wang, P., Lin, C., Smith, E. R., Guo, H., Sanderson, B. W., Wu, M., Gogol, M., Alexander, T., Seidel, C., Wiedemann, L. M., et al. (2009). Global analysis of H3K4 methylation defines MLL family member targets and points to a role for MLL1-mediated H3K4 methylation in the regulation of transcriptional initiation by RNA polymerase II. Mol. Cell. Biol. 29, 6074-6085.

Wang, Q. F., Wu, G., Mi, S., He, F., Wu, J., Dong, J., Luo, R. T., Mattison, R., Kaberlein, J. J., Prabhakar, S., et al. (2011). MLL fusion proteins preferentially regulate a subset of wild-type MLL target genes in the leukemic genome. Blood 117, 6895-6905.

Whitman, S. P., Liu, S., Vukosavljevic, T., Rush, L. J., Yu, L., Liu, C., Klisovic, M. I., Maharry, K., Guimond, M., Strout, M. P., et al. (2005). The MLL partial tandem duplication: evidence for recessive gain-of-function in acute myeloid leukemia identifies a novel patient subgroup for molecular-targeted therapy. Blood 106, 345-352.

Yokoyama, A., Lin, M., Naresh, A., Kitabayashi, I., and Cleary, M. L. (2010). A higher-order complex containing AF4 and ENL family proteins with P-TEFb facilitates oncogenic and physiologic MLL-dependent transcription. Cancer Cell 17, 198-212.

Yokoyama, A., Ficara, F., Murphy, M. J., Meisel, C., Naresh, A., Kitabayashi, I., and Cleary, M. L. (2011). Proteolytically cleaved MLL subunits are susceptible to distinct degradation pathways. J. Cell Sci. 124, 2208-2219.

Yu, B. D., Hess, J. L., Homing, S. E., Brown, G. A., and Korsmeyer, S. J. (1995). Altered Hox expression and segmental identity in Mll-mutant mice. Nature 378, 505-508.

Zhang, Y., Liu, T., Meyer, C. A., Eeckhoute, J., Johnson, D. S., Bernstein, B. E., Nusbaum, C., Myers, R. M., Brown, M., Li, W., and Liu, X. S. (2008). Model based analysis of ChIP-Seq (MACS). Genome Biol. 9, R137.

Example 2—Compound Synthesis

The following compounds were synthesized as potential inhibitors of IRAK4.

Scheme 1. Synthesis of Series I compounds 9a-d.

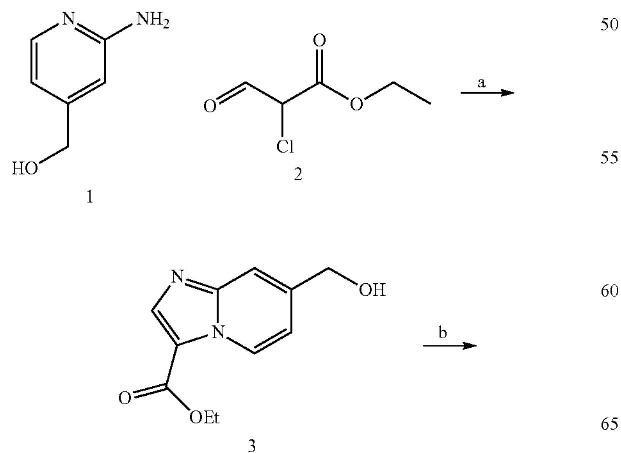

-continued

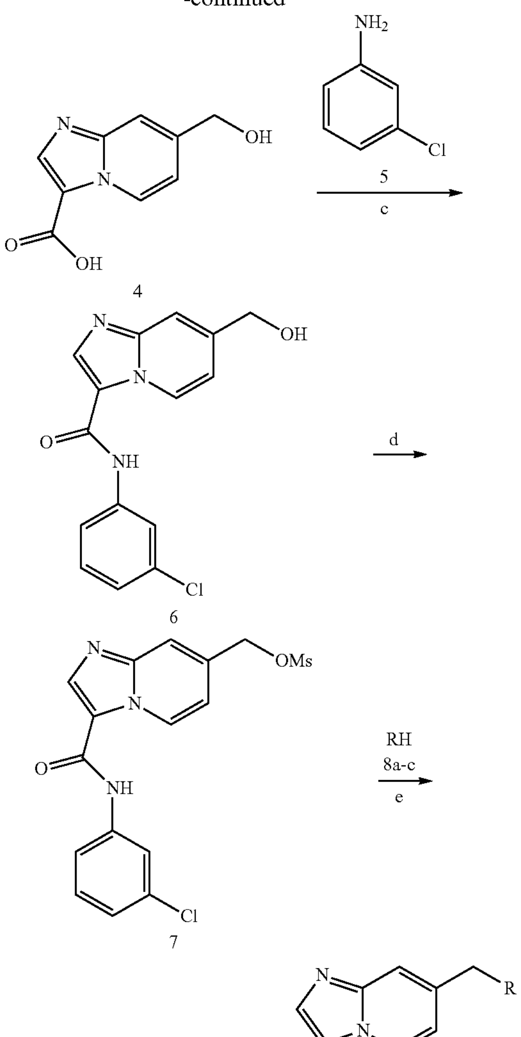

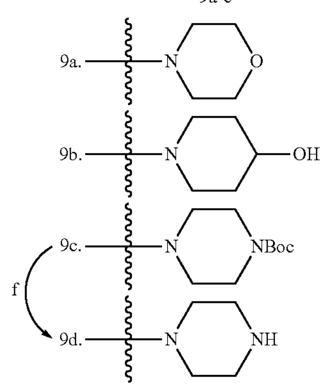

Reagent and conditions: (a) tBuOH, 75° C., 47%; (b) NaOH, MeOH; (c) HBTU, DIEPA, DMF, 17% in two steps;

(d) MsCl, DIEPA, $CHCl_3$, AcCN; (e) DMF, 26%-56% in two steps; (f) HCl, THF, 91%.
Scheme 2. Synthesis is Series II compounds 15 and 16.
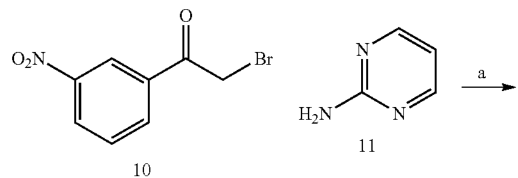
-continued
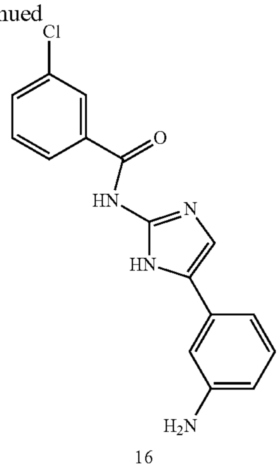
Reagent and conditions: (a) AcCN, MW, 150° C., 25 min; (b) $NH_2NH_2$, MW, 120° C., 20 min, 68% in two steps; (c) DIEPA, DCM, reflux, 26%; (d) Pd/C, $NH_2NH_2$, MeOH, 87%.
Scheme 3. Synthesis is Series II compounds 21.

-continued
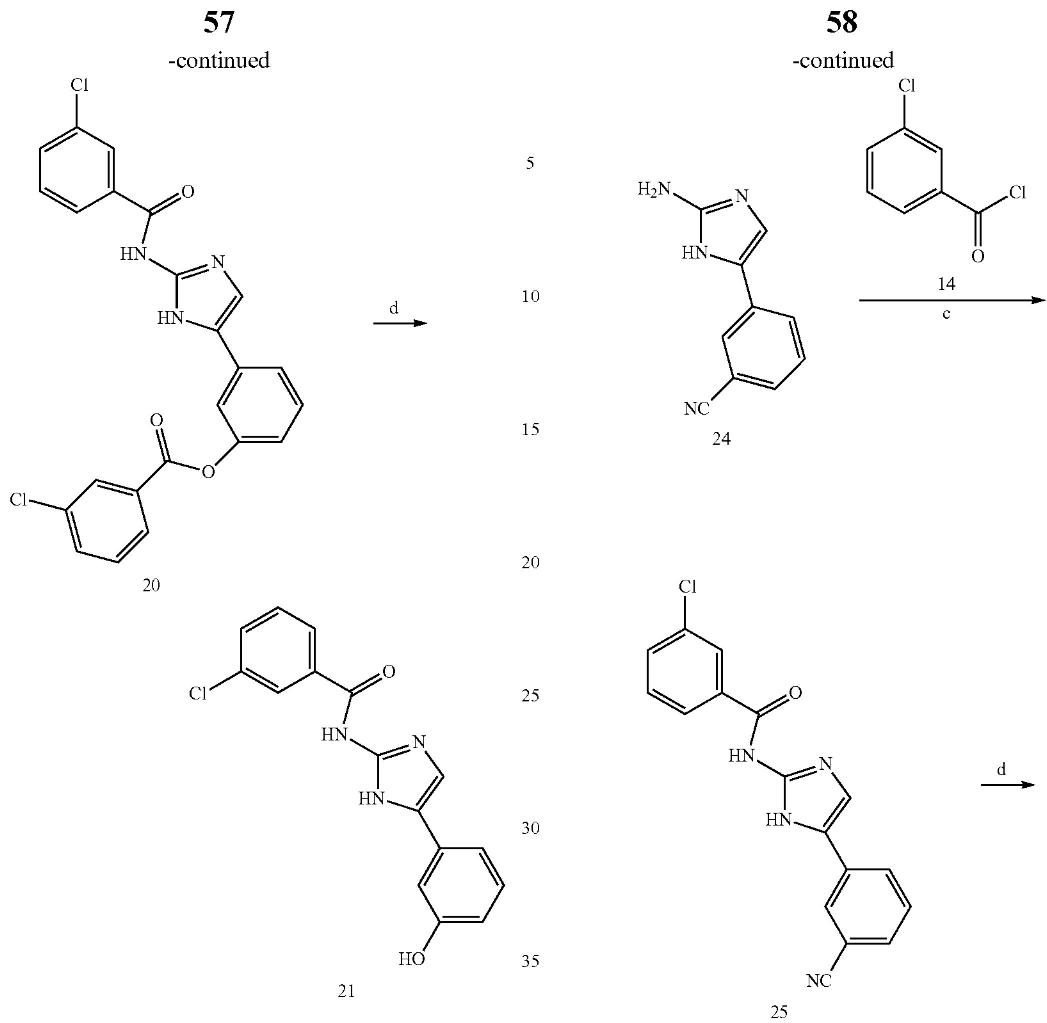
Reagent and conditions: (a) AcCN, MW, 150° C., 25 min; (b) $NH_2NH_2$, MW, 120° C., 20 min, 28% in two steps; (c) DIEPA, DCM, reflux; (d) Pd/C, $NH_2NH_2$, MeOH, 58% in two steps.
Scheme 4. Synthesis of Series II compounds 25 and 26.
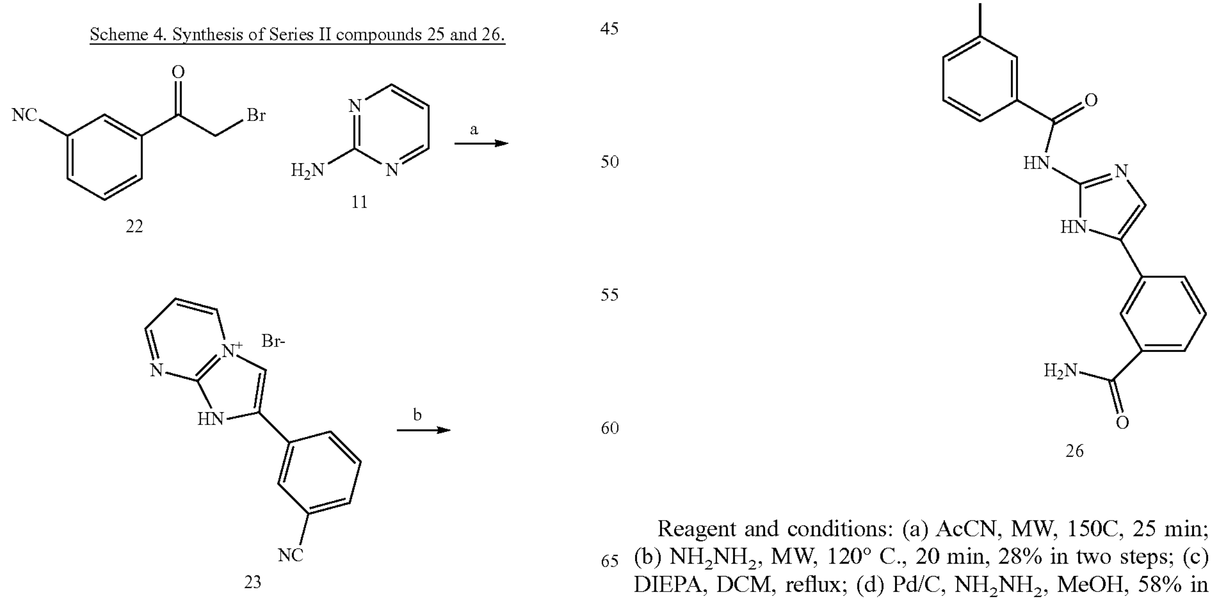
Reagent and conditions: (a) AcCN, MW, 150C, 25 min; (b) $NH_2NH_2$, MW, 120° C., 20 min, 28% in two steps; (c) DIEPA, DCM, reflux; (d) Pd/C, $NH_2NH_2$, MeOH, 58% in two steps.

Scheme 5. Synthesis of Series II compounds 31a-

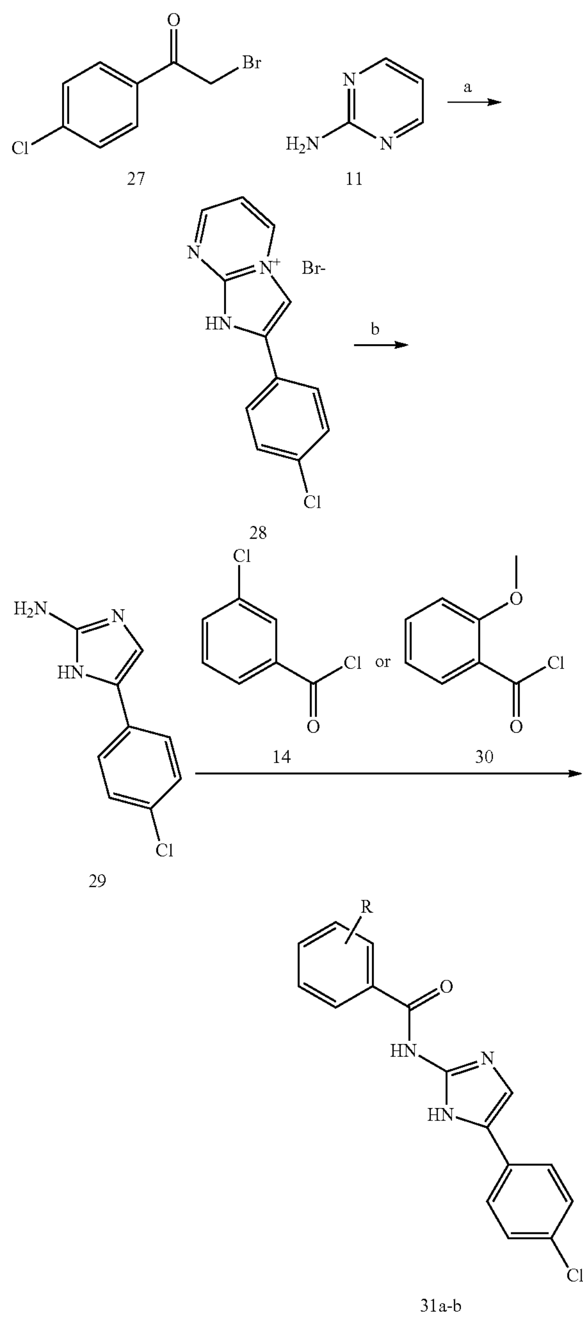

Reagent and conditions: (a) AcCN, MW, 150° C., 25 min; (b) $NH_2NH_2$, MW, 120° C., 20 min, 63% in two steps; (c) DIEPA, DCM, reflux.

Experimental Section:

Ethyl 7-(hydroxymethyl)imidazo[1,2-a]pyridine-3-carboxylate (3). A mixture of (2-aminopyridin-4-yl)methanol (1, 149 mg, 1.20 mmol) and ethyl 2-chloro-3-oxopropanoate (2, 144 mg, 0.956 mmol), in t-butanol (3 ml), was stirred at 75° C. under $N_2$ for 4 h. After cooling down to room temperature, solvent was evaporated, and the residue was further purified with flash silica gel column, with EA/Hex (gradient up to 99:1), to provide the product as white solid (98 mg, 47%). $^1$H NMR (500 MHz, Chloroform-d) δ 9.04 (dd, J=7.0, 0.9 Hz, 1H), 8.08 (s, 1H), 7.63 (t, J=1.4 Hz, 1H), 6.91 (dd, J=7.1, 1.7 Hz, 1H), 4.71 (d, J=1.3 Hz, 2H), 4.32 (q, J=7.1 Hz, 2H), 1.34 (t, J=7.2 Hz, 3H); $^{13}$C NMR (126 MHz, Chloroform-d) δ 160.43, 148.28, 143.42, 140.81, 127.06, 115.67, 113.44, 113.34, 62.91, 60.49, 14.40; ESIMS m/z 221.5 [MH]+.

N-(3-Chlorophenyl)-7-(hydroxymethyl)imidazo[1,2-a]pyridine-3-carboxamide (6). A solution of ethyl 7-(hydroxymethyl)imidazo[1,2-a]pyridine-3-carboxylate (3, 201 mg, 0.913 mmol) in MeOH (5 ml) was stirred at room temperature. 2 M NaOH aqueous solution (4.5 mL) was added, and the mixture was carefully acidified with 6 M HCl to pH=5. Remove all solvent, residues combined with HBTU (348 mg, 0.918 mmol) and DIPEA (360 mg, 2.79 mmol), dissolved with dry DMF (4 mL), and stirred under $N_2$ for 15 min. Then, a solution of 3-chloroaniline (190 mg, 1.489 mmol) in dry DMF (2 mL) was added. The mixture was stirred at room temperature overnight. The mixture was poured into water (25 mL), extracted with ethyl acetate (20 mL×3), the organic layers were combined, washed with water (20 mL) and brine (20 mL) sequentially, dried over $Na_2SO_4$. Remove solvent, residues further purified by flash silica gel column, with MeOH/DCM (gradient up to 15:85) to provide the product as white solid (47 mg, 17%). $^1$H NMR (500 MHz, Methanol-$d_4$) δ 9.49 (d, J=7.1 Hz, 1H), 8.46 (s, 1H), 7.91 (t, J=2.1 Hz, 1H), 7.70 (s, 1H), 7.61 (dd, J=8.3, 2.0 Hz, 1H), 7.34 (t, J=8.1 Hz, 1H), 7.14 (ddd, J=8.7, 6.6, 1.8 Hz, 2H), 4.76 (s, 2H); $^{13}$C NMR (126 MHz, Methanol-$d_4$) δ 159.18, 143.84, 139.87, 136.63, 133.98, 129.67, 127.52, 123.49, 120.08, 118.31, 113.24, 112.25, 62.19. ESIMS m/z 302.1 [MH]+.

N-(3-Chlorophenyl)-7-(morpholinomethyl)imidazo[1,2-a]pyridine-3-carboxamide (9a, NUCC-200515). A solution of N-(3-chlorophenyl)-7-(hydroxymethyl)imidazo[1,2-a]pyridine-3-carboxamide (6, 30 mg, 0.099 mmol) and N,N-diisopropylethylamine (0.078 ml, 0.449 mmol) in $CHCl_3$ (4 ml) and acetonitrile (0.5 ml) was stirred at 0° C. A solution of methanesulfonyl chloride (0.040 ml, 0.511 mmol) in $CHCl_3$ (1 mL) was added. The resulting mixture was stirred at 0° C. for 30 min, warmed to room temperature for 45 min. Solvent was removed, residues dissolved in dry DMF (2 mL), and a solution of morpholine (8a, 0.091 ml, 1.04 mmol) in dry DMF (1 mL) was added. The mixture was heated to 60° C. stirred under $N_2$ for 2 h. The mixture was diluted with water (20 mL), extracted with ethyl acetate (20 mL×3). The organic layers were combined, washed with water (20 mL) and brine (20 mL) sequentially, dried over $Na_2SO_4$. Remove solvent, residues further purified by flash silica gel column, with MeOH/DCM (gradient up to 15%), to afford the product as white solid (20.7 mg, 56%). $^1$H NMR (500 MHz, Chloroform-d and Methanol-$d_4$) δ 9.46 (d, J=7.1 Hz, 1H), 8.42 (s, 1H), 7.84 (t, J=2.0 Hz, 1H), 7.63 (s, 1H), 7.59-7.52 (m, 1H), 7.29 (t, J=8.1 Hz, 1H), 7.18 (dd, J=7.2, 1.5 Hz, 1H), 7.10 (ddd, J=8.1, 2.1, 0.9 Hz, 1H), 3.74 (t, J=4.6 Hz, 4H), 3.63 (s, 2H), 2.52 (dd, J=5.7, 3.6 Hz, 4H); $^{13}$C NMR (126 MHz, Chloroform-d and Methanol-$d_4$) δ 159.28, 139.59, 139.48, 136.91, 134.19, 129.71, 127.72, 123.82, 120.48, 118.53, 115.76, 115.52, 66.67, 61.84, 53.36. ESIMS m/z 371.2 [MH]+.

N-(3-Chlorophenyl)-7-((4-hydroxypiperidin-1-yl)methyl)imidazo[1,2-a]pyridine-3-carboxamide (9b, NUCC-200550). A solution of N-(3-chlorophenyl)-7-(hydroxymethyl)imidazo[1,2-a]pyridine-3-carboxamide (6, 17 mg, 0.056 mmol) and N,N-diisopropylethylamine (39 mg, 0.302 mmol) in $CHCl_3$ (2 ml) and acetonitrile (0.25 ml) was stirred at 0° C. A solution of methanesulfonyl chloride (26 mg, 0.227 mmol) in $CHCl_3$ (0.5 mL) was added. The resulting mixture was stirred at 0° C. for 30 min, warmed to room temperature for 45 min. Solvent was removed, residues combined with piperidin-4-ol (8b, 51.2 mg, 0.506 mmol), dissolved in dry DMF (2 mL). The mixture was heated to 60° C. stirred under $N_2$ for 2 h. Remove solvent in vacuo, residues further purified flash silica gel column, with MeOH/DCM (gradient up to 20:80), to afford the product as white solid (10.5 mg, 48%). $^1$H NMR (500 MHz, Methanol-d4) δ 9.48 (d, J=7.1 Hz, 1H), 8.41 (s, 1H), 7.85 (t, J=2.1 Hz, 1H), 7.66-7.52 (m, 2H), 7.31 (t, J=8.1 Hz, 1H), 7.18 (dd, J=7.2, 1.7 Hz, 1H), 7.12 (dd, J=7.9, 2.0 Hz, 1H), 3.75-3.52 (m, 2H), 3.39 (m, 1H), 3.06 (dt, J=13.1, 4.2 Hz, 2H), 2.83 (dt, J=11.8, 4.8 Hz, 2H), 2.60 (ddd, J=13.3, 10.8, 2.9 Hz, 2H), 2.33-2.14 (m, 2H); $^{13}$C NMR (126 MHz, Chloroform-d and Methanol-$d_4$) δ 159.34, 147.89, 139.92, 139.52, 136.93, 134.28, 129.75, 127.68, 123.94, 120.61, 118.61, 118.42, 115.86, 115.66, 67.28, 61.66, 43.72, 34.84. ESIMS m/z 385.5 [MH]+.

tert-Butyl 4-((3-((3-chlorophenyl)carbamoyl)imidazo[1,2-a]pyridin-7-yl)methyl)piperazine-1-carboxylate (9c, NUCC-200552. A solution of N-(3-chlorophenyl)-7-(hydroxymethyl)imidazo[1,2-a]pyridine-3-carboxamide (6, 17 mg, 0.056 mmol) and N,N-diisopropylethylamine (26 mg, 0.227 mmol) in $CHCl_3$ (0.5 ml) and acetonitrile (0.25 ml) was stirred at 0° C. A solution of methanesulfonyl chloride (26 mg, 0.227 mmol) in $CHCl_3$ (0.5 mL) was added. The resulting mixture was stirred at 0° C. for 30 min, warmed to room temperature for 45 min. Solvent was removed, residues combined with tert-butyl piperazine-1-carboxylate (8c, 63.6 mg, 0.341 mmol) dissolved in dry DMF (2 mL). The mixture was heated to 60° C. stirred under $N_2$ for 2 h. Remove solvent in vacuo, residues further purified by preparative HPLC, with AcCN/$H_2O$, to afford the product as white solid (6.9 mg, 26%). $^1$H NMR (500 MHz, Chloroform-d nd Methanol-d4) δ 9.49 (d, J=7.1 Hz, 1H), 8.45 (s, 1H), 7.90 (t, J=2.1 Hz, 1H), 7.67 (s, 1H), 7.64-7.54 (m, 1H), 7.33 (t, J=8.1 Hz, 1H), 7.23 (dd, J=7.2, 1.8 Hz, 1H), 7.18-7.07 (m, 1H), 3.72 (s, 2H), 3.48 (t, J=4.9 Hz, 4H), 2.52 (t, J=5.0 Hz, 4H), 1.45 (s, 9H). ESIMS m/z 470.5 [MH]+.

N-(3-Chlorophenyl)-7-(piperazin-1-ylmethyl)imidazo[1,2-a]pyridine-3-carboxamide (9d, NUCC-200551). A solution of tert-butyl 4-((3-((3-chlorophenyl)carbamoyl)imidazo[1,2-a]pyridin-7-yl)methyl)piperazine-1-carboxylate (9c, 5.8 mg, 0.012 mmol) and TFA (100 mg, 0.307 mmol) in DCM (1.5 mL) was stirred at room temperature overnight. Solvent was removed, and residues was washed with ether to afford product as white yellow solid as TFA salt (6.7 mg, 91%). $^1$H NMR (500 MHz, Methanol-d4) δ 9.74 (d, J=7.2 Hz, 1H), 8.70 (s, 1H), 8.04 (s, 1H), 7.95 (t, J=2.1 Hz, 1H), 7.71-7.57 (m, 1H), 7.43 (d, J=7.2 Hz, 1H), 7.38 (t, J=8.1 Hz, 1H), 7.18 (ddd, J=7.9, 2.1, 0.9 Hz, 1H), 4.51 (s, 2H), 3.73 (s, 4H). ESIMS m/z 370.5 [MH]+.

5-(3-Nitrophenyl)-1H-imidazol-2-amine (13). A solution of 2-bromo-1-(3-nitrophenyl)ethanone (10, 651 mg, 2.67 mmol) and pyrimidin-2-amine (11, 261 mg, 2.74 mmol) in acetonitrile (3 mL) was heated to 150° C. in a microwave reactor for 25 min. After cooling down to room temperature, hydrazine monohydrate (0.5 mL, 9.66 mmol) was added and the resulting mixture was heated to 120° C. in a microwave reactor for 20 min. The solid was removed by filtration, washed with acetonitrile. The filtrate was concentrated and further purified by flash silica gel column, with MeOH/DCM (gradient up to 15:85), to afford the product as dark brown oil (370 mg, 68%). $^1$H NMR (500 MHz, Chloroform-d and Methanol-d4) δ 8.36 (t, J=2.0 Hz, 1H), 8.04-7.90 (m, 1H), 7.86 (dt, J=7.9, 1.3 Hz, 1H), 7.45 (t, J=8.0 Hz, 1H), 6.98 (s, 1H); $^{13}$C NMR (126 MHz, Chloroform-d and Methanol-d4) δ 150.65, 148.58, 135.47, 129.58, 129.39, 120.20, 118.27. ESIMS m/z 205.1 [MH]+.

3-Chloro-N-(5-(3-nitrophenyl)-1H-imidazol-2-yl)benzamide (15). A solution of 5-(3-nitrophenyl)-1H-imidazol-2-amine (13, 102 mg, 0.500 mmol) and DIEPA (293 mg, 2.267 mmol) in DCM (10 mL) was stirred at room temperature, then a solution of 3-chlorobenzoyl chloride (14, 320 mg, 1.828 mmol) in DCM (10 mL) was added. The mixture was heated to reflux for 72 h. The solvent was evaporated, residues further purified by flash silica gel column, with EA/hex (gradient up to 60:40) to afford the product as yellow solid (45 mg, 26%). $^1$H NMR (500 MHz, Chloroform-d and Methanol-d4) δ 8.50 (s, 1H), 8.07 (dd, J=8.2, 2.3 Hz, 1H), 8.04-7.95 (m, 2H), 7.91-7.84 (m, 1H), 7.60-7.52 (m, 2H), 7.46 (t, J=7.9 Hz, 1H), 7.29 (s, 1H). ESIMS m/z 343.4 [MH]+.

N-(5-(3-aminophenyl)-1H-imidazol-2-yl)-3-chlorobenzamide (16, NUCC-200554). A solution of 3-chloro-N-(5-(3-nitrophenyl)-1H-imidazol-2-yl)benzamide (15, 6.3 mg, 0.018 mmol) and hydrazine monohydrate (57 mg, 1.07 mmol) in methanol was stirred at room temperature, 10% Pd/C (3.0 mg) was added. The mixture was heated to 80° C. for 10 min. The solid was removed by filtration. The filtrate was concentrated, and further purified by prep HLPC, with AcCN/$H_2O$, to afford the product as white solid (5.0 mg, 87%). $^1$H NMR (500 MHz, Chloroform-d and Methanol-d4) δ 8.04 (s, 1H), 7.94 (d, J=7.7 Hz, 1H), 7.57 (dd, J=8.0, 1.9 Hz, 1H), 7.48 (t, J=7.9 Hz, 1H), 7.20-7.08 (m, 2H), 7.03 (t, J=5.7 Hz, 2H), 6.66 (dd, J=7.9, 2.1 Hz, 1H); $^{13}$C NMR (126 MHz, Chloroform-d and Methanol-d4) δ 147.33, 134.43, 131.81, 129.78, 129.34, 127.92, 125.95, 114.76, 114.37, 111.38. ESIMS m/z 313.4 [MH]+.

3-(2-Amino-1H-imidazol-4-yl)phenol (19). A solution of 2-bromo-1-(3-hydroxyphenyl)ethan-1-one (17, 126 mg, 0.562 mmol) and pyrimidin-2-amine (11, 58 mg, 0.591 mmol) in acetonitrile (1 mL) was heated to 150° C. in a microwave reactor for 25 min. After cooling down to room temperature, hydrazine monohydrate (0.2 mL, 3.8 mmol) was added and the resulting mixture was heated to 120° C. in a microwave reactor for 20 min. The mixture was concentrated and further purified by preparative HPLC, with AcCN/$H_2O$, to provide the product as pale yellow oil (28 mg, 28%). $^1$H NMR (500 MHz, Methanol-d4) δ 7.13 (t, J=7.9 Hz, 1H), 7.04 (d, J=7.7 Hz, 1H), 7.01 (t, J=2.0 Hz, 1H), 6.84 (s, 1H), 6.62 (dd, J=8.1, 2.4 Hz, 1H); $^{13}$C NMR (126 MHz, Methanol-d4) δ 157.30, 150.32, 134.39, 129.15, 114.97, 112.64, 110.33. ESIMS m/z 176.3 [MH]+.

N-(5-(3-hydroxyphenyl)-1H-imidazol-2-yl)benzamide (21, NUCC-200618). A solution of 3-(2-amino-1H-imidazol-4-yl)phenol (19, 28 mg, 0.16 mmol) and DIEPA (147 mg, 1.14 mmol) in DCM (10 mL) was stirred at room temperature, then a solution of 3-chlorobenzoyl chloride (14, 142 mg, 0.787 mmol) in DCM (10 mL) was added. The mixture was heated to reflux overnight. Solvent was evaporated, residues combined with 10% Pd/C (37 mg) and hydrazine monohydrate (389 mg, 7.28 mmol), dissolved with methanol (10 mL). The resulting mixture was heated to 80° C. for 30 min. The solid was remove by filtration, the filtrate was concentrated and purified by flash silica gel column, with ethylacetate/hexanes (gradient up to 99:1), to afford the product as white solid (26 mg, 58%). $^1$H NMR (500 MHz, Chloroform-d and Methanol-d4) δ 7.94-7.87 (m, 2H), 7.52 (dd, J=8.5, 6.5 Hz, 1H), 7.47-7.41 (m, 2H), 7.14 (t, J=7.9 Hz, 1H), 7.07-7.03 (m, 1H), 7.02 (d, J=2.8 Hz, 2H), 6.66 (dd, J=8.0, 2.5 Hz, 1H); $^{13}$C NMR (126 MHz, Chloroform-d and Methanol-d4) δ 167.21, 157.18, 132.87, 132.53, 129.81, 128.65, 127.59, 116.01, 114.09, 111.32. ESIMS m/z 280.4 [MH]+.

3-(2-Amino-1H-imidazol-4-yl)benzonitrile (24). A solution of 3-(2-bromoacetyl)benzonitrile (22, 462 mg, 2.06 mmol) and pyrimidin-2-amine (11, 197 mg, 2.07 mmol) in acetonitrile (2 mL) was heated to 150° C. in a microwave reactor for 25 min. After cooling down to room temperature, hydrazine monohydrate (0.4 mL, 7.73 mmol) was added and the resulting mixture was heated to 120° C. in a microwave reactor for 20 min. The solid was removed by filtration, washed with acetonitrile. The filtrate was concentrated and further purified by preparative HPLC, with AcCN/$H_2O$, to provide the product as yellow oil (69 mg, 18%). $^1H$ NMR (500 MHz, Methanol-d4) δ 7.90 (s, 1H), 7.84 (dt, J=4.7, 2.3 Hz, 1H), 7.45 (d, J=5.9 Hz, 2H), 7.06 (s, 1H); $^{13}C$ NMR (126 MHz, Methanol-d4) δ 151.03, 135.26, 132.70, 129.22, 128.65, 127.83, 126.76, 118.58, 112.13, 111.43. ESIMS m/z 185.2 [MH]+.

3-Chloro-N-(5-(3-cyanophenyl)-1H-imidazol-2-yl)benzamide (25, NUCC-200617). A solution of 3-(2-amino-1H-imidazol-4-yl)benzonitrile (24, 69 mg, 0.38 mmol) and DIEPA (182 mg, 1.41 mmol) in DCM (10 mL) was stirred at room temperature, then a solution of 3-chlorobenzoyl chloride (14, 175 mg, 0.97 mmol) in DCM (5 mL) was added. The mixture was heated to reflux overnight. The solvent was evaporated, residues further purified by flash silica gel column, with EA/hex (gradient up to 99:1) to afford the product as yellow solid (23 mg, 19%). $^1H$ NMR (500 MHz, Chloroform-d and Methanol-d4) δ 7.96-7.88 (m, 2H), 7.85 (d, J=7.7 Hz, 1H), 7.81 (dt, J=7.9, 1.3 Hz, 1H), 7.50 (dt, J=8.3, 1.3 Hz, 1H), 7.48-7.37 (m, 3H), 7.18 (s, 1H). ESIMS m/z 323.3 [MH]+.

N-(5-(3-carbamoylphenyl)-1H-imidazol-2-yl)-3-chlorobenzamide (26, NUCC-200619). A suspension of 3-chloro-N-(5-(3-cyanophenyl)-1H-imidazol-2-yl)benzamide (25, 9.0 mg, 0.028 mmol) and potassium carbonate (90 mg, 0.651 mmol) in DMSO was stirred at room temperature under $N_2$. Hydrogen peroxide (0.090 ml, 0.882 mmol) and magnesium oxide (12 mg, 0.298 mmol) was added sequentially. The resulting mixture was stirred at room temperature for 4 h, and poured into water (5 mL), and extracted with ethyl acetate (8 mL×5). The organic layers were combined, washed with water (10 mL) and brine (10 mL) sequentially, dried over $Na_2SO_4$. Remove solvent, the solid was triturated with ether (10 mL), to afford the product as pale yellow solid (5.1 mg, 54%). ESIMS m/z 341.3 [MH]+. $^1H$ NMR (500 MHz, Methanol-d4) δ 8.54 (s, 1H), 8.23 (s, 1H), 8.15 (d, J=7.8 Hz, 1H), 8.02 (s, 1H), 7.90 (d, J=8.0 Hz, 1H), 7.79 (d, J=7.6 Hz, 1H), 7.63 (t, J=7.9 Hz, 1H), 7.58 (d, J=7.5 Hz, 1H), 7.47 (t, J=7.9 Hz, 1H).

5-(4-Chlorophenyl)-1H-imidazol-2-amine (29). A solution of 2-bromo-1-(4-chlorophenyl)ethanone (27, 526 mg, 2.25 mmol) and pyrimidin-2-amine (11, 225 mg, 2.37 mmol) in acetonitrile (3 mL) was heated to 150° C. in a microwave reactor for 25 min. After cooling down to room temperature, hydrazine monohydrate (0.4 mL, 7.73 mmol) was added and the resulting mixture was heated to 120° C. in a microwave reactor for 20 min. The solid was removed by filtration, washed with acetonitrile. The filtrate was concentrated and further purified by flash silica gel column, with MeOH/DCM (gradient up to 15:85), to afford the product as dark brown oil (273 mg, 63%). $^1H$ NMR (500 MHz, Methanol-d4) δ 7.64-7.44 (m, 2H), 7.27 (d, J=8.4 Hz, 2H), 6.91 (s, 1H); $^{13}C$ NMR (126 MHz, Methanol-d4) δ 151.15, 149.10, 130.73, 129.34, 126.61, 123.39. ESIMS m/z 194.0 [MH]+.

3-Chloro-N-(5-(4-chlorophenyl)-1H-imidazol-2-yl)benzamide (31a). A solution of 5-(4-chlorophenyl)-1H-imidazol-2-amine (29, 34 mg, 0.176 mmol) and DIEPA (104 mg, 0.80 mmol) in DCM (4 mL) was stirred at room temperature, then a solution of 3-chlorobenzoyl chloride (14, 66 mg, 0.37 mmol) in DCM (1 mL) was added. The mixture was heated to reflux overnight. The solvent was evaporated, residues further purified by flash silica gel column, with EA/hex (gradient up to 50:50) to afford the product as white yellow solid (25 mg, 43%). $^1H$ NMR (500 MHz, Methanol-d4) δ 7.96 (t, J=1.9 Hz, 1H), 7.84 (dt, J=7.5, 1.5 Hz, 1H), 7.58-7.49 (m, 3H), 7.42 (t, J=7.9 Hz, 1H), 7.31 (d, J=8.7 Hz, 2H), 7.08 (s, 1H); $^{13}C$ NMR (126 MHz, Chloroform-d and Methanol-d4) δ 161.79, 138.64, 130.84, 130.65, 128.62, 128.50, 126.01, 124.83, 123.98, 121.89, 121.81. ESIMS m/z 332.0 [MH]+.

N-(5-(4-Chlorophenyl)-1H-imidazol-2-yl)-2-methoxybenzamide (31b). A solution of 5-(4-chlorophenyl)-1H-imidazol-2-amine (29, 37.3 mg, 0.156 mmol) and DIEPA (99 mg, 0.77 mmol) in DCM (6 mL) was stirred at room temperature, then a solution of 2-methoxybenzoyl chloride (30, 44 mg, 0.26 mmol) in DCM (2 mL) was added. The mixture was heated to reflux overnight. The solvent was evaporated, residues further purified by flash silica gel column, with EA/hex (gradient up to 60:40) to afford the product as white yellow solid (40.1 mg, 79%). $^1H$ NMR (500 MHz, Chloroform-d) δ 7.54-7.44 (m, 3H), 7.38 (dd, J=7.5, 1.8 Hz, 1H), 7.27-7.17 (m, 2H), 7.05 (td, J=7.5, 0.9 Hz, 1H), 7.00 (d, J=8.4 Hz, 1H), 6.58 (s, 1H); $^{13}C$ NMR (126 MHz, Chloroform-d) δ 168.01, 156.34, 150.93, 137.29, 133.13, 133.01, 131.27, 128.77, 128.68, 126.33, 123.22, 120.85, 111.68, 107.64, 55.84. ESIMS m/z 328.1 [MH]+.

Example 3—Compound Testing

The newly synthesized compounds were tested in an IRAK4 kinase inhibition assay as follows. In a 10 μl reaction, 10 ng Human IRAK4, 12.5 μM ATP, 500 ng dephosphorylated MBP (EMD Millipore), and different IRAK inhibitors were used in 1× kinase buffer (60 mM HEPES-NaOH, pH 7.5, 3 mM MgCl2, 3 mM MnCl2, 1.2 mM DTT, 0.1% BSA) at room temperature for 45 minutes. The ADP formed from the kinase reaction was measured by the ADP-Glo™ Kinase Assay (Cat.#V9101) and the luminescence was measured with a Tecan Infinite M1000 plate reader. As indicated in FIG. 15, Compound NUCC0200554 (Compound 16 of Example 2) and Compound NUCC0200618 (Compound 21 of Example 2) were observed to inhibit IRAK4 kinase activity.

The newly synthesized compound NUCC0200554 (Compound 16 of Example 2) and compound NUCC0200618 (Compound 21 of Example 2) were further tested in MLL stabilization assay, in an IRAK4 kinase activity as described above, and in a SEM cell proliferation assay as follows. SEM (ACC-546) leukemia cells were maintained in Iscove's Modified Dulbecco's Medium (IMDM) with 10% FBS. Viable SEM cells were seeded at 0.2 million/ml, and treated with different concentrations of inhibitors at the indicated concentrations for three days. Viable cells were monitored by trypan blue exclusion staining and counted using a Vi-CELL XR cell counter. Data are represented as Mean±SD (n=3). The results provided in FIG. 16 demonstrate that the tested compounds stabilize MLL, inhibit IRAK4 kinase, and inhibit SEM cell proliferation at increasing concentration.

The gene expression profiles of SEM cells treated with newly synthesized compound NUCC0200554 (Compound 16 of Example 2) and compound NUCC0200618 (Compound 21 of Example 2) as follows. After inhibitor treatment for 3 days, SEM cells were collected and lysed with Trizol reagent. Total RNA was extracted from Trizol according to the manufacturer's instructions. The RNA was treated with DNase I (NEB) and cleaned with the Qiagen RNeasy mini kit. 500 ng RNA was used for library preparation with TruSeq Stranded Total RNA with Ribo-Zero Gold kit (Illumina, RS-123-2201). The sequenced reads were aligned to the human genome (UCSC hgl9) with TopHat 2.1.0 using gene annotations from Ensembl 72. Differential gene expression was performed with Deseq2. The results are provided in FIG. 17.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a cancer characterized by a rearrangement in the mixed lineage leukemia gene (MLL-r) in a subject in need thereof, wherein the cancer is MLL-r leukemia, the method comprising administering a therapeutic amount of a therapeutic agent that inhibits the biological activity of interleukin-1 receptor-associated kinase 4 (IRAK4), wherein the therapeutic agent comprises a compound having a formula:

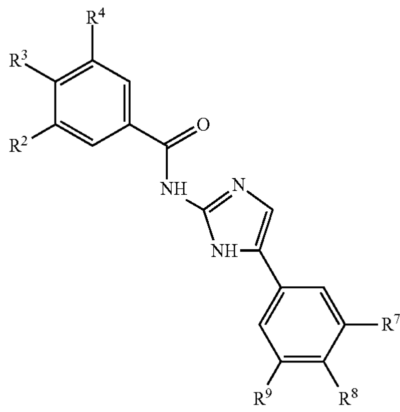

wherein $R^2$, $R^3$, and $R^4$ are the same or different and each of $R^2$, $R^3$, and $R^4$ is independently —$(CH_2)_m$R', wherein m is 0-6 and R' is selected from hydrogen, halo, amino or alk-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino; and wherein $R^7$, $R^8$, and $R^9$ are the same or different and each of $R^7$, $R^8$, and $R^9$ is independently —$(CH_2)_n$R", wherein n is 0-6 and R" is selected from hydrogen, halo, amino or alkyl-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino.

2. A compound having a formula:

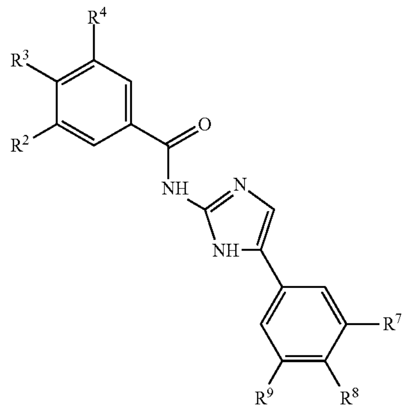

wherein $R^2$, $R^3$, and $R^4$ are the same or different and each of $R^2$, $R^3$, and $R^4$ is independently —$(CH_2)_m$R', wherein m is 0-6 and R' is selected from hydrogen, halo, amino or alkyl-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino; and wherein $R^7$, $R^8$, and $R^9$ are the same or different and each of $R^7$, $R^8$, and $R^9$ is independently —$(CH_2)_n$R", wherein n is 0-6 and R" is selected from hydrogen, halo, amino or alkyl-substituted amino, hydroxyl, cyano, nitro, alkyl which may be straight chain or branched, allyl, alkoxy which may be straight chain or branched, saturated or unsaturated cycloalkyl which optionally is substituted with alkyl, halo, hydroxyl, or amino, and saturated or unsaturated heterocycloalkyl which optionally is substituted with alkyl, halo, hydroxyl, or amino.

3. The compound of claim 2, wherein at least one of $R^2$, $R^3$, $R^4$, $R^7$, $R^8$, and $R^9$ is not hydrogen.

4. The compound of claim 2, wherein at least one of $R^2$, $R^3$, and $R^4$ is halo or alkyoxy and at least one of $R^7$, $R^8$, and $R^9$ is amino, alkyl-substituted amino, dialkyl-substituted amino, amido, cyano, nitro, hydroxyl, or halo.

5. The compound of claim 2, wherein the compound has a formula selected from:
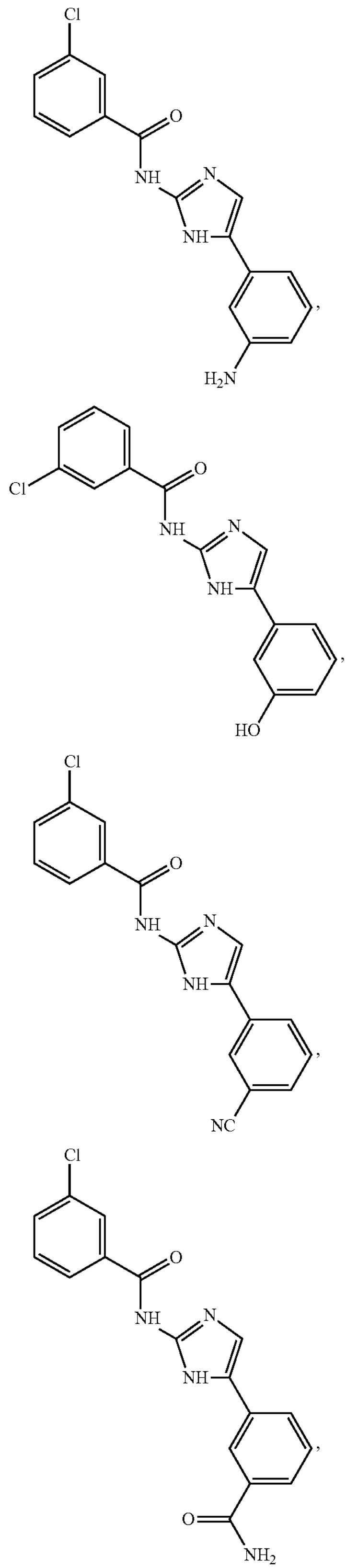 [SMILES: Nc1cccc(-c2cnc(NC(=O)c3cccc(Cl)c3)[nH]2)c1 ; O=C(Nc1ncc(-c2cccc(O)c2)[nH]1)c1cccc(Cl)c1 ; N#Cc1cccc(-c2cnc(NC(=O)c3cccc(Cl)c3)[nH]2)c1 ; NC(=O)c1cccc(-c2cnc(NC(=O)c3cccc(Cl)c3)[nH]2)c1]
-continued
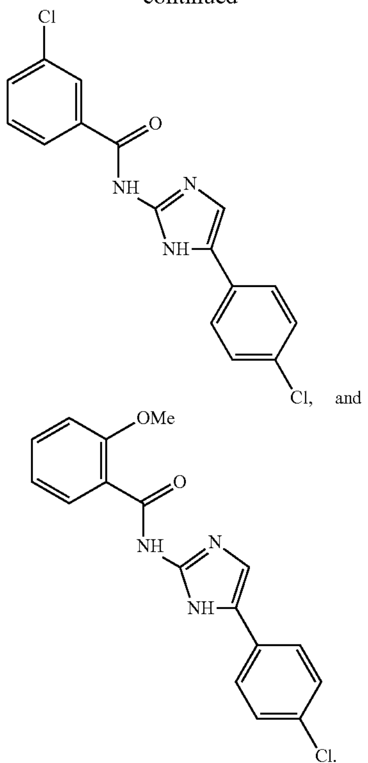
6. The compound of claim 2, wherein the compound has a formula selected from:
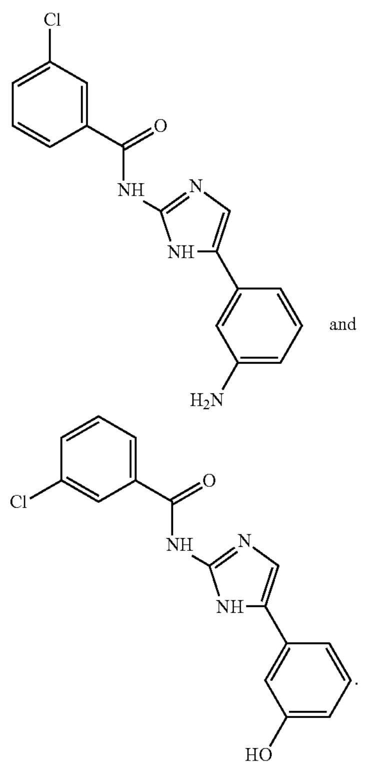
7. A pharmaceutical composition comprising the compound of claim 2 and a pharmaceutically acceptable carrier.

8. A pharmaceutical composition comprising the compound of claim 3 and a pharmaceutically acceptable carrier.

9. A pharmaceutical composition comprising the compound of claim 4 and a pharmaceutically acceptable carrier.

10. A pharmaceutical composition comprising the compound of claim 5 and a pharmaceutically acceptable carrier.

11. A pharmaceutical composition comprising the compound of claim 6 and a pharmaceutically acceptable carrier.

12. A method for treating MLL-r leukemia in a subject in need thereof, the method comprising administering to the subject the pharmaceutical composition of claim 7.

13. A method for treating MLL-r leukemia in a subject in need thereof, the method comprising administering to the subject the pharmaceutical composition of claim 8.

14. A method for treating MLL-r leukemia in a subject in need thereof, the method comprising administering to the subject the pharmaceutical composition of claim 9.

15. A method for treating MLL-r leukemia in a subject in need thereof, the method comprising administering to the subject the pharmaceutical composition of claim 10.

16. A method for treating MLL-r leukemia in a subject in need thereof, the method comprising administering to the subject the pharmaceutical composition of claim 11.

* * * * *